US009650350B2

(12) United States Patent
Matsuno et al.

(10) Patent No.: US 9,650,350 B2
(45) Date of Patent: *May 16, 2017

(54) POLYLACTIC ACID COMPOSITION

(75) Inventors: Yuichi Matsuno, Chiyoda-ku (JP);
Masaki Mitsunaga, Chiyoda-ku (JP);
Jitsuo Oda, Chiyoda-ku (JP);
Masatsugu Furuki, Chiyoda-ku (JP);
Shinichiro Shoji, Iwakuni-shi (JP);
Takuro Kitamura, Chiyoda-ku (JP);
Yoshitaka Shibata, Chiyoda-ku (JP)

(73) Assignee: TEIJIN LIMITED, Osaka (JP)

( * ) Notice: Subject to any disclaimer, the term of this patent is extended or adjusted under 35 U.S.C. 154(b) by 900 days.

This patent is subject to a terminal disclaimer.

(21) Appl. No.: 13/522,777

(22) PCT Filed: Jan. 17, 2011

(86) PCT No.: PCT/JP2011/051145
§ 371 (c)(1),
(2), (4) Date: Jul. 18, 2012

(87) PCT Pub. No.: WO2011/087155
PCT Pub. Date: Jul. 21, 2011

(65) Prior Publication Data
US 2012/0289625 A1    Nov. 15, 2012

(30) Foreign Application Priority Data

Jan. 18, 2010 (JP) ................. 2010-008165
Feb. 9, 2010 (JP) ................. 2010-026537
Jun. 3, 2010 (JP) ................. 2010-127777
Jun. 9, 2010 (JP) ................. 2010-132003
Jun. 9, 2010 (JP) ................. 2010-132004
Jun. 10, 2010 (JP) ................. 2010-132928

(51) Int. Cl.
C07D 273/02 (2006.01)
C07D 273/08 (2006.01)
C07D 498/04 (2006.01)
C07D 498/10 (2006.01)
C07D 498/14 (2006.01)
C08K 5/29 (2006.01)
C08K 5/3442 (2006.01)
C08K 5/35 (2006.01)
C08L 67/04 (2006.01)
C08L 101/16 (2006.01)

(52) U.S. Cl.
CPC ......... *C07D 273/08* (2013.01); *C07D 498/04* (2013.01); *C07D 498/10* (2013.01); *C07D 498/14* (2013.01); *C08K 5/29* (2013.01); *C08L 101/16* (2013.01)

(58) Field of Classification Search
USPC ........ 523/451, 453, 456; 524/133, 140, 323, 524/392
See application file for complete search history.

(56) References Cited

U.S. PATENT DOCUMENTS

| | | | |
|---|---|---|---|
| 8,030,382 B2 * | 10/2011 | Endo et al. .................. | 524/141 |
| 8,178,628 B2 * | 5/2012 | Tanaka et al. ............... | 525/415 |
| 2005/0032947 A1 | 2/2005 | Takahashi et al. | |
| 2008/0161554 A1 * | 7/2008 | Dai et al. .................... | 540/454 |
| 2009/0318628 A1 | 12/2009 | Tanaka et al. | |
| 2011/0160364 A1 * | 6/2011 | Toyohara et al. ........... | 524/117 |
| 2011/0224385 A1 | 9/2011 | Shoji et al. | |
| 2011/0237755 A1 | 9/2011 | Shoji et al. | |
| 2014/0066555 A1 | 3/2014 | Matsuno et al. | |

FOREIGN PATENT DOCUMENTS

| | | | |
|---|---|---|---|
| DE | 10004328 A1 * | 8/2001 | .......... C07D 257/12 |
| EP | 2 116 576 A1 | 11/2009 | |
| JP | 2002-30208 A | 1/2002 | |
| JP | 2005-53870 A | 3/2005 | |
| JP | 2006-328284 A | 12/2006 | |
| JP | 2008-050579 A | 3/2008 | |
| JP | 2008-248028 A | 10/2008 | |
| JP | 2011/051145 | 3/2011 | |
| WO | 2008/010355 A1 | 1/2008 | |

(Continued)

OTHER PUBLICATIONS

Molina et al., "A New Efficient Preparation of Cyclic Carbodiimides from Bis(iminophosphorones) and System Boc2O(DMAP)," Org. Chem. 1994, 59, pp. 7306-7315.*
Lukyanenko et al., "Macroheterocycles; XXVIII. Coronands with Carbodiimide groups and Their Chemical Transformations," Sythesis (1986), 11, pp. 928-930.*
Molina et al., "A New and Efficient Preparation of Cyclic Carbodiimides from Bis(iminophosphoranes) and the System Boc20/Dmap," J. Org. Chem. (1994), vol. 59, pp. 7306-7315.*
Glinka et al., "A New Method of Synthesizing 8-10 membered Heterocyclic Systems Condensed with Two Aromatic Rings," Polish Journal of Chemistry, (1984), vol. 58, Issue 1-2-3, pp. 259-262.*

(Continued)

*Primary Examiner* — Randy Gulakowski
*Assistant Examiner* — Ha S Nguyen
(74) *Attorney, Agent, or Firm* — Sughrue Mion, PLLC

(57) ABSTRACT

A resin composition which comprises polylactic acid, does not release an isocyanate group at the time of production and has excellent hydrolysis resistance and a low environmental burden.
The resin composition comprises:
(A) 100 parts by weight of a resin component (component A) containing polylactic acid (component A-α);
(B) 0.001 to 10 parts by weight of a compound (component B) having one carbodiimide group and a cyclic structure in which first nitrogen and second nitrogen are bonded to each other via a bonding group, the cyclic structure consisting of 8 to 50 atoms; and
(C) 0.001 to 2 parts by weight of at least one antioxidant (component C) selected from the group consisting of a hindered phenol-based compound, a phosphite-based compound, a phosphonite-based compound and a thioether-based compound.

20 Claims, No Drawings

(56) References Cited

FOREIGN PATENT DOCUMENTS

| WO | 2008/013316 A1 | 1/2008 |
| WO | WO 2008010355 A1 * | 1/2008 |
| WO | WO 2008013316 A1 * | 1/2008 |
| WO | WO 2008102919 A1 * | 8/2008 |
| WO | 2010/053167 A1 | 5/2010 |
| WO | 2010/071212 A1 | 6/2010 |

OTHER PUBLICATIONS

Communication dated Sep. 5, 2014 from the European Patent Office in counterpart application No. 11733019.1- 1306.
Tetrahedron Letters, vol. 34, No. 32, 5155-5158, 1993, Medium- and Large-Membered Rings from Bis(iminophosphoranes): An Efficient Preparation of Cyclic Carbodiimides, Pedro Molina et al.
Journal of Organic Chemistry, vol. 61, No. 13, 4289-4299, 1996, New Models for the Study of the Racemization Mechanism of Carbodiimides; Synthesis and structure (X-ray Crystallography and 1H NMR) of Cyclic Carbodiimides, Pedro Molina et al.
Journal of Organic Chemistry, vol. 43, No. 8, 1544-1546, 1978, Macrocyclic Ureas as Masked Isocyanates, Henri Ulrich et al.
Journal of Organic Chemistry, vol. 48, No. 10, 1694-1700, 1983, Synthesis and Reactions of Cyclic Carbodiimides, R. Richter et al.
Journal of Organic Chemistry, vol. 59, No. 24, 7306-7315, 1994, A New and Efficient Preparation of Cyclic Carbodiimides from Bis(iminophosphoranes) and the System Boc2O/DMP, Pedro Molina et al.
International Preliminary Report on Patentability and Written Opinion for PCT/JP2011/051145 issued Aug. 7, 2012.
International Search Report of PCT/JP2011/051145 dated Mar. 1, 2011.

* cited by examiner

POLYLACTIC ACID COMPOSITION

TECHNICAL FIELD

The present invention relates to a resin composition which comprises polylactic acid and has excellent hydrolysis resistance.

BACKGROUND ART

Due to concerns about the depletion of oil resources and the increasing amount of carbon dioxide in the air causing global warming, a great deal of attention is now paid to biomass resources whose raw materials do not depend on oil and which materialize "carbon neutral" without increasing the amount of carbon dioxide when they are burnt. Even in the field of polymers, the development of biomass plastics produced from the biomass resources is actively under way. Since polylactic acid out of the biomass plastics has relatively high heat resistance and mechanical properties, its application is spreading to tableware, packaging materials and miscellaneous goods. Further, the possibility of using the biomass resources as industrial materials is now under study.

However, since polylactic acid has low hydrolysis resistance, the spread of its use to industrial materials such as electric/electronic parts and auto parts in which typical engineering plastics such as polycarbonate, polybutylene terephthalate and polyethylene terephthalate are used does not proceed.

Patent Document 1 proposes that an end-sealing agent is added to polylactic acid to seal at least part of the terminal carboxyl group of polylactic acid so as to suppress a reduction in strength by a hot water treatment. However, to use the polylactic acid as an industrial material, the level of its hydrolysis resistance is unsatisfactory.

Patent Document 2 proposes to improve the hydrolysis resistance of polylactic acid by mixing a carbodiimide compound and an antioxidant. This carbodiimide compound releases an isocyanate compound during a reaction for bonding to the end of a polyester, thereby producing a characteristic smell to worsen work environment.

Patent Document 3 discloses a macrocyclic carbodiimide compound. Since this compound is produced under high dilution, the concentration of the macrocyclic carbodiimide compound is low and it takes many days to react it with a polymer. Therefore, its utility as an end-sealing agent for polymers is low. Also, its efficiency as an end-sealing agent for polymers is low due to a high molecular weight for the carbodiimide group. Patent Document 3 does not take into consideration the reduction of an isocyanate gas smell produced by the end-sealing of a polymer. This macrocyclic carbodiimide compound has a long chain and is easily decomposed at a high temperature and unsuitable for use as an end-sealing agent for polymers having a high melting point, such as polyester.

(Patent Document 1) JP-A 2002-30208
(Patent Document 2) JP-A 2005-53870
(Patent Document 3) US Patent No. 2008/0161554

DISCLOSURE OF THE INVENTION

It is an object of the present invention to provide a resin composition which comprises polylactic acid and is excellent in hydrolysis resistance and heat stability and has a low environmental burden. It is another object of the present invention to provide a process for producing a resin composition in a good work environment by preventing the release of a compound having an isocyanate group when a resin composition comprising a resin component containing polylactic acid and a carbodiimide compound is to be produced.

The inventors of the present invention found that when a cyclic carbodiimide compound (component B) and an antioxidant (component C) are added to polylactic acid having a low environmental burden, a resin composition which prevents the release of a compound having an isocyanate group to provide a good work environment and has excellent hydrolysis resistance is obtained.

They also found that the cyclic carbodiimide compound (component B) has higher melt heat stability and long-term heat resistance and more rarely deteriorates by heat history than a linear carbodiimide compound which has been used up till now.

That is, the present invention is a resin composition which comprises (A) 100 parts by weight of a resin component (component A) containing polylactic acid (component A-α), (B) 0.001 to 10 parts by weight of a cyclic carbodiimide compound (component B) having one carbodiimide group and a cyclic structure represented by the following formula (5) in which first nitrogen and second nitrogen of the carbodiimide group are bonded to each other via a bonding group, the cyclic structure consisting of 8 to 50 atoms, and (C) 0.001 to 2 parts by weight of at least one antioxidant (component C) selected from the group consisting of a hindered phenol-based compound, a phosphite-based compound, a phosphonite-based compound and a thioether-based compound.

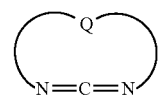

(5)

(In the above formula, Q is a divalent to tetravalent bonding group represented by the following formula (5-1), (5-2) or (5-3).)

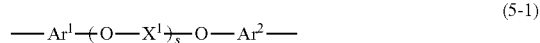

(5-1)

(5-2)

(5-3)

(In the above formulas, $Ar^1$ and $Ar^2$ are each independently a divalent to tetravalent aromatic group having 5 to 15 carbon atoms. $R^1$ and $R^2$ are each independently a divalent to tetravalent aliphatic group having 1 to 20 carbon atoms, a divalent to tetravalent alicyclic group having 3 to 20 carbon atoms, a combination thereof, or a combination of the above aliphatic group, the above alicyclic group and a divalent to tetravalent aromatic group having 5 to 15 carbon atoms. s is an integer of 0 to 10. k is an integer of 0 to 10. $X^1$ and $X^2$ are each independently a divalent to tetravalent aliphatic group having 1 to 20 carbon atoms, a divalent to tetravalent alicyclic group having 3 to 20 carbon atoms, a divalent to tetravalent aromatic group having 5 to 15 carbon atoms, or a combination thereof. $X^3$ is a divalent to tetravalent aliphatic group having 1 to 20 carbon atoms, a divalent to tetravalent alicyclic group having 3 to 20 carbon atoms, a divalent to tetravalent aromatic group having 5 to 15 carbon atoms, or a combination thereof. $Ar^1$, $Ar^2$, $R^1$, $R^2$, $X^1$, $X^2$ and $X^3$ may contain a hetero atom. When Q is a divalent bonding group, $Ar^1$, $Ar^2$, $R^1$, $R^2$, $X^1$, $X^2$ and $X^3$ are all divalent groups. When Q is a trivalent bonding group, one of $Ar^1$, $Ar^2$, $R^1$, $R^2$, $X^1$, $X^2$ and $X^3$ is a trivalent group. When Q is a tetravalent bonding group, one of $Ar^1$, $Ar^2$, $R^2$, $X^1$, $X^2$ and $X^3$ is a tetravalent group, or two of them are trivalent groups.)

The present invention includes a process for producing the above resin composition. The present invention also includes a molded article made of the resin composition.

BEST MODE FOR CARRYING OUT THE INVENTION

The components and ratio thereof of the resin composition of the present invention and a process for preparing the resin composition will be described hereinunder.

<Component A: Resin Component>

The resin component (component A) contains polylactic acid (component A-α). The resin composition (component A) may contain polylactic acid (component A-α) and a thermoplastic resin (component A-β).

That is, the resin component (component A) contains (i) polylactic acid (component A-α) or (ii) 5 to 95 wt % of polylactic acid (component A-α) and 95 to 5 wt % of at least one thermoplastic resin (component A-β) selected from the group consisting of an aromatic polyester (component A-β-1), a polyolefin (component A-β-2) and an aromatic polycarbonate (component A-β-3).

(Component A-α)

In the present invention, the resin component (component A) contains polylactic acid (component A-α). The polylactic acid (component A-α) may be poly-L-lactic acid (component A-α-1) essentially composed of an L-lactic acid unit, poly-D-lactic acid (component A-α-2) essentially composed of a D-lactic acid unit, or a mixture thereof. The poly-L-lactic acid (component A-α-1) and the poly-D-lactic acid (component A-α-2) are essentially composed of an L-lactic acid unit and a D-lactic acid unit represented by the formula (1), respectively.

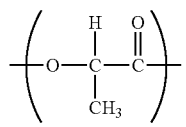
(1)

Preferably, the optical purity of the poly-L-lactic acid (component A-α-1) or the poly-D-lactic acid (component A-α-2) is 90 to 100 mol %. When the optical purity falls below this range, the crystallinity and melting point of the polylactic acid lower, thereby making it difficult to obtain high heat resistance. Therefore, the melting point of the poly-L-lactic acid or the poly-D-lactic acid is preferably 160° C. or higher, more preferably 170° C. or higher, much more preferably 175° C. or higher. From this point of view, the optical purity of lactic acid or lactide as the raw material of a polymer is preferably 96 to 100 mol %, more preferably 97.5 to 100 mol %, much more preferably 98.5 to 10 mol %, particularly preferably 99 to 100 mol %.

The comonomer unit is a D-lactic acid in the case of poly-L-lactic acid or an L-lactic acid unit in the case of poly-D-lactic acid. Units other than the lactic acid units are also included. The content of the comonomer unit is preferably 10 mol % or less, more preferably 5 mol % or less, much more preferably 2 mol % or less, most preferably 1 mol % or less.

Examples of the comonomer unit include units derived from dicarboxylic acids, polyhydric alcohols, hydroxycarboxylic acids and lactones having a functional group capable of forming at least two ester bonds, and units derived from polyesters, polyethers and polycarbonates comprising these as constituent components.

The dicarboxylic acids include succinic acid, adipic acid, azelaic acid, sebacic acid, terephthalic acid and isophthalic acid. The polyhydric alcohols include aliphatic polyhydric alcohols such as ethylene glycol, 1,3-propanediol, propylene glycol, butanediol, pentanediol, hexanediol, octanediol, glycerin, sorbitan, neopentyl glycol, diethylene glycol, triethylene glycol, polyethylene glycol, polytrimethylene glycol and polypropylene glycol. Aromatic polyhydric alcohols such as an adduct of bisphenol with ethylene oxide are also included. The hydroxycarboxylic acids include glycolic acid and hydroxybutyric acid. The lactones include glycolide, ε-caprolactone, β-propiolactone, δ-butyrolactone, β- or γ-butyrolactone, pivalolactone and δ-valerolactone.

The weight average molecular weight of each of the poly-L-lactic acid (component A-α-1) and the poly-D-lactic acid (component A-α-2) is preferably 80,000 to 300,000, more preferably 100,000 to 250,000, much more preferably 120,000 to 230,000 in order to obtain both the mechanical properties and moldability of the resin composition of the present invention.

Preferably, the poly-L-lactic acid (component A-α-1) contains 90 mol % or more of an L-lactic acid unit and the poly-D-lactic acid (component A-α-2) contains 90 mol % or more of a D-lactic acid unit.

The poly-L-lactic acid (component A-α-1) and the poly-D-lactic acid (component A-α-2) can be manufactured by a conventionally known process. Examples of the process include the melt ring-opening polymerization of L-lactide or D-lactide, the solid-phase polymerization of polylactic acid having a low molecular weight, and direct polymerization for dehydrating and condensing lactic acid. The polymerization reaction can be carried out in a conventionally known reactor. For example, vertical reactors or horizontal reactors having high-viscosity agitating elements such as helical ribbon elements can be used alone or in combination. Alternatively, batch, continuous and semi-batch processes may be used alone or in combination. In the solid-phase polymerization, it is preferred from the viewpoints of the prevention of the fusion of a pellet and production efficiency that a prepolymer should be crystallized in advance. Polymerization is carried out at a fixed temperature within a temperature range from the glass transition temperature to lower than the melting point of the prepolymer or by elevating the temperature gradually along with the proceeding of polymerization in a fixed vertical or horizontal reactor or a reactor (rotary kiln, etc.) whose vessel turns, such as a tumbler or kiln. It is also preferred that the inside pressure of the reactor should be reduced or a heated inert gas stream should be circulated to remove produced water efficiently A metal-containing catalyst is preferably used in the melt ring-opening polymerization of lactide from the viewpoints of production efficiency and the quality of a polymer. The metal-containing catalyst is preferably a catalyst containing tin, particular preferably a divalent tin compound from the viewpoints of catalytic activity and the suppression of a side reaction. Specific examples of the metal-containing catalyst include diethoxytin, dinonyloxytin, tin myristate, tin octylate and tin stearate. Out of these, tin octylate is particularly preferred as its safety is confirmed in FDA. The amount of the catalyst is preferably $0.1 \times 10^{-4}$ to $50 \times 10^{-4}$ mol, more preferably $1 \times 10^{-4}$ to $30 \times 10^{-4}$ mol, particularly preferably $2\times10^{-4}$ to $15\times10^{-4}$ mol based on 1 kg of a lactide when reactivity and the color and safety of the obtained polylactide are taken into consideration.

An alcohol may be used as a polymerization initiator. The alcohol preferably does not impede the polymerization of polylactic acid and is nonvolatile, and preferred examples thereof include decanol, dodecanol, tetradecanol, hexadecanol and octadecanol.

It is preferred that the metal-containing catalyst used at the time of polymerization should be inactivated with a conventionally known deactivator prior to its use. Although the deactivator is not particularly limited as long as it is a deactivator which is generally used as a deactivator for polymerization catalysts for polyester resin, a phosphono-fatty acid ester represented by the following formula (2) is preferred.

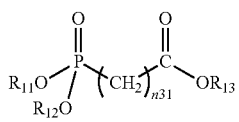

(2)

In the above formula, $R_{11}$ to $R_{13}$ are each independently an alkyl group having 1 to 20 carbon atoms or aryl group having 6 to 12 carbon atoms. Examples of the alkyl group include ethyl group, propyl group, butyl group, pentyl group and hexyl group. Examples of the aryl group include phenyl group and naphthalen-yl group. $R_{11}$ to $R_{13}$ may be the same or different. $n^{31}$ is an integer of 1 to 3.

Examples of the compound represented by the formula (2) include ethyl diethylphosphonoacetate, ethyl di-n-propylphosphonoacetate, ethyl di-n-butylphosphonoacetate, ethyl di-n-hexylphosphonoacetate, ethyl di-n-octylphosphonoacetate, ethyl di-n-decylphosphonoacetate, ethyl di-n-dodecylphosphonoacetate, ethyl di-n-octadecylphosphonoacetate, ethyl diphenylphosphonoacetate, decyl diethylphosphonoacetate, dodecyl diethylphosphonoacetate, octadecyl diethylphosphonoacetate, ethyl diethylphosphonopropionate, ethyl di-n-propylphosphonopropionate, ethyl di-n-butylphosphonopropionate, ethyl di-n-hexylphosphonopropionate, ethyl di-n-octylphosphonopropionate, ethyl di-n-decylphosphonopropionate, ethyl di-n-dodecylphosphonopropionate, ethyl di-n-octadecylphosphonopropionate, ethyl diphenylphosphonopropionate, decyl diethylphosphonopropionate, dodecyl diethylphosphonopropionate, octadecyl diethylphosphonopropionate, ethyl diethylphosphonobutyrate, ethyl di-n-propylphosphonobutyrate, ethyl di-n-butylphosphonobutyrate, ethyl di-n-hexylphosphonobutyrate, ethyl di-n-octylphosphonobutyrate, ethyl di-n-decylphosphonobutyrate, ethyl di-n-dodecylphosphonobutyrate, ethyl di-n-octadecylphosphonobutyrate, ethyl diphenylphosphonobutyrate, decyl diethylphosphonobutyrate, dodecyl diethylphosphonobutyrate and octadecyl diethylphosphonobutyrate. When efficacy and handling ease are taken into consideration, ethyl diethylphosphonoacetate, ethyl di-n-propylphosphonoacetate, ethyl di-n-butylphosphonoacetate, ethyl di-n-hexylphosphonoacetate, decyl diethylphosphonoacetate and octadecyl diethylphosphonoacetate are preferred.

When the number of carbon atoms of $R_{11}$ to $R_{13}$ are 20 or less in the formula (2), the melting point of the compound becomes lower than the production temperature of the polylactic acid or the resin composition, thereby making it possible to melt mix it fully and capture the metal polymerization catalyst efficiently. The phosphono-fatty acid ester has an aliphatic hydrocarbon group between the diester phosphonate moiety and the carboxylate moiety. When $n^{31}$ is an integer of 1 to 3, the metal polymerization catalyst contained in the polylactic acid can be captured efficiently.

The content of the phosphono-fatty acid ester is preferably 0.001 to 0.5 parts by weight, more preferably 0.02 to 0.2 parts by weight based on 100 parts by weight of the polylactic acid. When the content of the phosphono-fatty acid ester is too low, the deactivation efficiency for the residual metal polymerization catalyst becomes very low and a satisfactory effect is not obtained. When the content is too high, the contamination of a mold used for molding becomes marked. The above polymerization deactivator is preferably added at the end of polymerization but may be added arbitrarily in the extrusion or molding process as required.

It is preferred that the polylactic acid (component A-α) should contain poly-L-lactic acid (component A-α-1) essentially composed of an L-lactic acid unit and poly-D-lactic acid (component A-α-2) essentially composed of a D-lactic acid unit and that the weight ratio of the component A-α-1 to the component A-α-2 be preferably in the range of 10:90 to 90:10. The (component A-α-1)/(component A-α-2) weight ratio is more preferably 40:60 to 60:40, particularly preferably 45:55 to 55:45.

Further, When a phosphate metal salt (s) represented by the formula (s) (3) and/or (4) is/are contained in a mixture of the poly-L-lactic acid (component A-α-1) and the poly-D-lactic acid (component A-α-2) in an amount of 0.01 to 2.0 parts by weight based on 100 parts by weight of the total of the poly-L-lactic acid (component A-α-1) and the poly-D-lactic acid (component A-α-2), polylactic acid highly forming a stereocomplex crystal can be obtained. When the amount of the phosphate metal salt is smaller than 0.01 part by weight, the formation of the stereocomplex crystal and the improvement of crystallinity may not be observed and when the amount is larger than 2.0 parts by weight, the decomposition of a polylactic acid component such as coloration or the production of foreign matter may occur. From this point of view, the amount of the phosphate metal salt is selected from a range of more preferably 0.02 to 1.0 part by weight, much more preferably 0.03 to 1.0 part by weight.

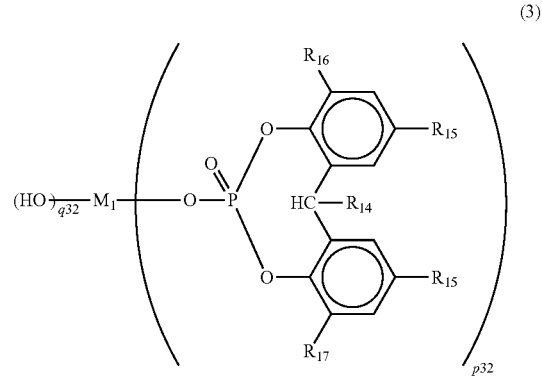

(3)

(In the above formula, $R_{14}$ is a hydrogen atom or alkyl group having 1 to 4 carbon atoms, $R_{15}$, $R_{16}$ and $R_{17}$ are each independently a hydrogen atom or alkyl group having 1 to 12 carbon atoms, $M_1$ is an alkali metal atom, alkali earth metal atom, zinc atom or aluminum atom, $P^{32}$ is 1 or 2, and $q^{32}$ is 0 when $M_1$ is an alkali metal atom, alkali earth metal atom or zinc atom and 1 or 2 when $M_1$ is an aluminum atom.)

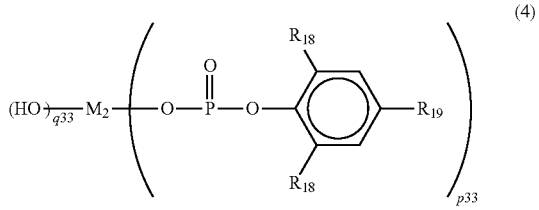

(4)

(In the above formula, $R_{18}$ and $R_{19}$ are each independently a hydrogen atom or alkyl group having 1 to 12 carbon atoms, $M_2$ is an alkali metal atom, alkali earth metal atom, zinc atom or aluminum atom, $p^{33}$ is 1 or 2, and $q^{33}$ is 0 when $M_2$ is an alkali metal atom, alkali earth metal atom or zinc atom and 1 or 2 when $M_2$ is an aluminum atom.)

The polylactic acid obtained as described above becomes a stereocomplex polylactic acid (component A-α-3) highly forming a stereocomplex crystal, and the stereocomplex crystal rate represented by the following equation using melting enthalpy derived from the polylactic acid (component A) crystal in the temperature elevation step of differential scanning calorimeter (DSC) measurement is preferably 80% or more.

Stereocomplex crystal rate=ΔHms/(ΔHms+ΔHmh)×100

[In the above equation, ΔHmh and ΔHms represent the melting enthalpy (ΔHmh) of a crystal melting point which appears at a temperature lower than 190° C. and the melting enthalpy (ΔHms) of a crystal melting point which appears at a temperature of 190° C. or higher to lower than 250° C. in the temperature elevation step of a differential scanning calorimeter (DSC), respectively.]

Δmh and ΔHms are obtained by measuring the resin composition by means of a differential scanning calorimeter (DSC) in a nitrogen atmosphere at a temperature elevation rate of 20° C./rain.

As the stereocomplex crystal rate becomes higher, moldability and heat resistance become higher, and the stereocomplex crystal rate is more preferably 85% or more, more preferably 90% or more. When the stereocomplex crystal rate is lower than 80%, the characteristic feature of a homopolylactic acid crystal derived from poly-L-lactic acid or poly-D-lactic acid appears and heat resistance becomes unsatisfactory.

The melting point of the stereocomplex polylactic acid is preferably 200° C. or higher, more preferably 205° C. or higher, much more preferably 210° C. or higher. When the melting point of the stereocomplex polylactic acid is lower than 200° C., heat resistance becomes unsatisfactory due to its low crystallinity and melting point.

The melting enthalpy of the stereocomplex polylactic acid is preferably 20 J/g or more, more preferably 30 J/g or more. When the melting enthalpy is lower than 20 J/g, crystallinity becomes low and heat resistance becomes unsatisfactory. Stated more specifically, preferably, the stereocomplex crystal rate is 80% or more, the melting point is 200° C. or higher, and the melting enthalpy is 20 J/g or more.

(Component A-β: Thermoplastic Resin)

The resin component (component A) may contain at least one thermoplastic resin (component A-β) selected from the group consisting of an aromatic polyester (component A-β-1), a polyolefin (component A-β-2) and an aromatic polycarbonate (component A-β-3).

(Component A-β-1: Aromatic Polyester)

The aromatic polyester (component A-β-1) is preferably an aromatic polyester which comprises an aromatic dicarboxylic acid in an amount of 70 mol % or more based on 100 mol % of a dicarboxylic acid component out of the dicarboxylic acid component and the diol component forming the polyester. The aromatic polyester comprises the aromatic dicarboxylic acid in an amount of more preferably 90 mol % or more, most preferably 99 mol % or more.

Examples of the dicarboxylic acid include terephthalic acid, isophthalic acid, adipic acid, 2-chloroterephthalic acid, 2,5-dichloroterephthalic acid, 2-methylterephthalic acid, 4,4-stylbenedicarboxylic acid, 4,4'-biphenyldicarboxylic acid, orthophthalic acid, 2,6-naphthalenedicarboxylic acid, 2,7-naphthalenedicarboxylic acid, bis(p-carboxyphenyl) methane, anthracenedicarboxylic acid, 4,4'-diphenylether dicarboxylic acid, 4,4'-diphenoxyethane dicarboxylic acid, 5-Na sulfoisophthalic acid and ethylene-bis-p-benzoic acid. These dicarboxylic acids may be used alone or in combination of two or more.

The aromatic polyester (component A-β-1) may comprise less than 30 mol % of an aliphatic dicarboxylic acid component besides the above aromatic dicarboxylic acid. Examples of the aliphatic dicarboxylic acid include adipic acid, sebacic acid, azelaic acid, dodecanedioic acid, 1,3-cyclohexanedicarboxylic acid and 1,4-cyclohexanedicarboxylic acid.

Examples of the diol component include ethylene glycol, diethylene glycol, 1,2-propylene glycol, 1,3-propaneidol, 2,2-dimethyl-1,3-propanediol, trans- or cis-2,2,4,4-tetramethyl-1,3-cyclobutanediol, 1,4-butanediol, neopentyl glycol, 1,5-pentanediol, 1,6-hexanediol, 1,4-cyclohexane dimethanol, 1,3-cyclohexane dimethanol, decamethylene glycol, cyclohexanediol, p-xylenediol, bisphenol A, tetrabromobisphenol A and tetrabromobisphenol A-bis(2-hydroxyethyl ether). They may be used alone or in combination of two or more. The content of a dihydric phenol in the diol component is preferably 30 mol % or less.

Examples of the aromatic polyester (component A-β-1) include polyethylene terephthalate (PET), polypropylene terephthalate, polybutylene terephthalate (PBT), polyhexylene terephthalate, polyethylene naphthalate (PEN), polybutylene naphthalate (PBN), polyethylene-1,2-bis(phenoxy) ethane-4,4'-dicarboxylate, and copolyesters such as polyethylene isophthalate/terephthalate copolymer and polybutylene terephthalate/isophthalate copolymer.

The terminal group structure of the aromatic polyester (component A-β-1) is not particularly limited, and the amounts of the hydroxyl group and the carboxyl group which are both terminal groups may be almost the same, or one of them may be larger than the other. The terminal groups may be sealed by reacting a compound having reactivity to the terminal groups.

The aromatic polyester (component A-β-1) can be produced by polymerizing a dicarboxylic acid component and a diol component under heating in the presence of a polycondensation catalyst containing titanium, germanium or antimony and discharging the by-produced water or lower alcohol to the outside of the system in accordance with a commonly used method. For example, germanium oxides, hydroxides, halides, alcoholates and phenolates may be used as germanium-based polymerization catalysts, and specific examples thereof include germanium oxide, germanium hydroxide, germanium tetrachloride and tetramethoxy germanium. A compound such as a manganese, zinc, calcium or magnesium compound which is used in a transesterification reaction which is pre-stage of conventionally known polycondensation may be used in combination. Polycondensation can be carried out by deactivating the catalyst with a compound such as a phosphoric acid or phosphorous acid compound after the end of the transesterification reaction. The method for producing the aromatic polyester may be carried out in a batch or continuous polymerization manner.

Out of the aromatic polyesters, polybutylene terephthalate and polyethylene terephthalate are particularly preferred because long-term heat resistance is easily obtained. Polybutylene terephthalate is a polymer obtained from a polycondensation reaction of terephthalic acid or a derivative thereof and 1,4-butanediol or a derivative thereof. Polyethylene terephthalate is a polymer obtained from a polycondensation reaction of terephthalic acid or a derivative thereof and ethylene glycol or a derivative thereof. As described above, polymers containing another dicarboxylic acid component and another alkylene glycol component are also included.

Although the terminal group structures of polybutylene terephthalate and polyethylene terephthalate are not particularly limited as described above, more preferably, the number of the terminal carboxyl groups is small as compared with the number of the terminal hydroxyl groups. The methods for producing these aromatic polyesters may be carried out in any one of the above manners but preferably a continuous polymerization manner. This is because quality stability is high and it is economically advantageous. Further, an organic titanium compound is preferably used as a polymerization catalyst. This is because it tends to have a small influence upon a transesterification reaction.

Preferred examples of the organic titanium compound include titanium tetrabutoxide, titanium isopropoxide, titanium oxalate, titanium acetate, titanium benzoate, titanium trimellitate, and a reaction product of tetrabutyl titanate and trimellitic anhydride. The amount of the organic titanium compound is preferably such that the amount of its titanium atom becomes 3 to 12 mg atom % based on the acid component constituting polybutylene terephthalate or polyethylene terephthalate.

Although the molecular weight of the aromatic polyester (component A-β-1) is not particularly limited, the intrinsic viscosity measured at 35° C. in o-chlorophenol as a solvent of the aromatic polyester resin is preferably 0.5 to 1.5, particularly preferably 0.6 to 1.2.

As for the ratio of the polylactic acid (component A-α) and the aromatic polyester (component A-β-1), preferably, the amount of the polylactic acid (component A-α) is 5 to 95 wt % and the amount of the aromatic polyester (component A-β-1) is 95 to 5 wt %. More preferably, the amount of the polylactic acid (component A-α) is 25 to 95 wt % and the amount of the aromatic polyester (component A-β-1) is 75 to 5 wt %. Much more preferably, the amount of the polylactic acid (component A-α) is 50 to 95 wt % and the amount of the aromatic polyester (component A-β-1) is 50 to 5 wt %. When the amount of the aromatic polyester is 95 wt % or more, the effect of reducing an environmental burden becomes small and when the amount of the aromatic polyester is 5 wt % or less, the effect of improving hydrolysis resistance and long-term heat resistance is not obtained.

(Component A-β-2: Polyolefin)

The polyolefin (component A-β-2) is a homopolymer or copolymer of an olefin such as ethylene, propylene or butene, or a copolymer of one of these olefins and a copolymerizable monomer component. More specifically, the polyolefin is at least one selected from the group consisting of polyethylene and polypropylene. Polypropylene is particularly preferred from the viewpoint of the crystallinity of the resin composition. The term "polypropylene" as used herein means a polyolefin containing at least 1 mol % of a propylene unit as a constituent unit. The above polypropylene contains at least 1 mol %, preferably at least 10 mol %, particularly preferably at least 75 mol % of the propylene unit as a constituent unit.

Other constituent units are ethylene and an α-olefin having 4 to 20 carbon atoms. Specific examples thereof include 1-butene, 1-pentene, 1-hexene, 1-octene, 1-decene, 1-dodecene, 1-tetradecene, 1-hexadecene, 1-octadecene, 1-eicosene, 3-methyl-1-butene, 3-methyl-1-pentene, 3-ethyl-1-pentene, 4-methyl-1-pentene, 4-methyl-1-hexene, 4,4-dimethyl-1-hexene, 4,4-dimethyl-1-pentene, 4-ethyl-1-hexene and 3-ethyl-1-hexene. They may be used alone or in combination of two or more.

The polyolefin (component A-β-2) preferably has a melt volume flow rate (MVR, ISO1133, 240° C., 2.16 kg) of 1 to 80 $cm^3$/10 min. When a polyolefin having a melt volume flow rate of 2 to 70 $cm^3$/10 min is used, a molded article having a good appearance is obtained advantageously, and a polyolefin having a melt volume flow rate of 3 to 60 $cm^3$/10 min is particularly preferred.

As for the ratio of the polylactic acid (component A-α) and the polyolefin (component A-β-2), preferably, the amount of the polylactic acid (component A-α) is 5 to 95 wt % and the amount of the polyolefin (component A-β-2) is 95 to 5 wt %. More preferably, the amount of the polylactic acid (component A-α) is 25 to 95 wt % and the amount of the polyolefin (component A-β-2) is 75 to 5 wt %. Much more preferably, the amount of the polylactic acid (component A-α) is 50 to 95 wt % and the amount of the polyolefin (component A-β-2) is 50 to 5 wt %. When the amount of the polyolefin (component A-β-2) is 95 wt % or more, the effect of reducing an environmental burden becomes small and when the amount of the polyolefin (component A-β-2) is 5 wt % or less, the effect of improving impact resistance and ductility is not obtained.

(Component A-β-3: Aromatic Polycarbonate)

The aromatic polycarbonate (component A-β-3) is obtained by reacting a dihydric phenol with a carbonate precursor. Examples of the reaction include interfacial polycondensation, melt transesterification, the solid-phase transesterification of a carbonate prepolymer and the ring-opening polymerization of a cyclic carbonate compound.

Typical examples of the dihydric phenol used herein include hydroquinone, resorcinol, 4,4'-biphenol, 1,1-bis(4-hydroxyphenyl)ethane, 2,2-bis(4-hydroxyphenyl)propane (commonly known as "bisphenol A"), 2,2-bis(4-hydroxy-3-methylphenyl)propane, 2,2-bis(4-hydroxyphenyl)butane, 1,1-bis(4-hydroxyphenyl)-1-phenylethane, 1,1-bis(4-hydroxyphenyl)cyclohexane, 1,1-bis(4-hydroxyphenyl)-3,3,5-trimethylcyclohexane, 2,2-bis(4-hydroxyphenyl)pentane, 4,4'-(p-phenylenediisopropylidene)diphenol, 4,4'-(m-phenylenediisopropylidene)diphenol, 1,1-bis(4-hydroxyphenyl)-4-isopropylcyclohexane, bis(4-hydroxyphenyl)oxide, bis(4-hydroxyphenyl)sulfide, bis(4-hydroxyphenyl)sulfoxide, bis(4-hydroxyphenyl)sulfone, bis(4-hydroxyphenyl)ketone, bis(4-hydroxyphenyl)ester, bis(4-hydroxy-3-methylphenyl)sulfide, 9,9-bis(4-hydroxyphenyl)fluorene and 9,9-bis(4-hydroxy-3-methylphenyl)fluorene. Out of these, bis(4-hydroxyphenyl)alkanes are preferred, and bisphenol A is particularly preferred as it is excellent in toughness and deformation properties and generally used.

In the present invention, a special polycarbonate produced by using another dihydric phenol may be used as the component A-β-3 in addition to the bisphenol A-based polycarbonates which are general-purpose polycarbonates. For example, polycarbonates (homopolymers or copolymers) obtained by using 4,4'-(m-phenylenediisopropylidene)diphenol (may be abbreviated as "BPM" hereinafter), 1,1-bis(4-hydroxyphenyl)cyclohexane, 1,1-bis(4-hydroxyphenyl)-3,3,5-trimethylcyclohexane (may be abbreviated as "Bis-TMC" hereinafter), 9,9-bis(4-hydroxyphenyl)fluorene or 9,9-bis(4-hydroxy-3-methylphenyl)fluorene (may be abbreviated as "BCF" hereinafter) as part or all of the dihydric phenol component are suitable for use in fields in which the requirements for stability to dimensional change by water absorption and form stability are very strict. These dihydric phenols except for BPA are used in an amount of preferably 5 mol % or more, particularly preferably 10 mol % or more based on the total of all the dihydric phenol components constituting the polycarbonate.

Particularly when high stiffness and excellent hydrolysis resistance are required, the component A-β-3 is particularly preferably one of the following copolycarbonates (1) to (3).

(1) A copolycarbonate which comprises 20 to 80 mol % (preferably 40 to 75 mol %, more preferably 45 to 65 mol %) of BPM and 20 to 80 mol % (preferably 25 to 60 mol %, more preferably 35 to 55 mol %) of BCF based on 100 mol % of the dihydric phenol component constituting the polycarbonate.

(2) A copolycarbonate which comprises 10 to 95 mol % (preferably 50 to 90 mol %, more preferably 60 to 85 mol %) of BPA and 5 to 90 mol % (preferably 10 to 50 mol %, more preferably 15 to 40 mol %) of BCF based on 100 mol % of the dihydric phenol component constituting the polycarbonate.

(3) A copolycarbonate which comprises 20 to 80 mol % (preferably 40 to 75 mol %, more preferably 45 to 65 mol %) of BPM and 20 to 80 mol % (preferably 25 to 60 mol %, more preferably 35 to 55 mol %) of Bis-TMC based on 100 mol % of the dihydric phenol component constituting the polycarbonate.

These special polycarbonates may be used alone or in combination of two or more. They may be mixed with a widely used bisphenol A type polycarbonate.

The production processes and characteristic properties of these special polycarbonates are detailed in, for example, JP-A 6-172508, JP-A 8-27370, JP-A 2001-55435 and JP-A 2002-117580.

Out of the above aromatic polycarbonates, polycarbonates whose water absorption coefficient and Tg (glass transition temperature) have been adjusted to the following ranges by controlling their compositions are excellent in the hydrolysis resistance of the polymer itself and rarely warp after molding. Therefore, they are particularly preferred in fields in which form stability is required.

(i) Polycarbonates having a water absorption coefficient of 0.05 to 0.15%, preferably 0.06 to 0.13% and a Tg of 120 to 180° C., or (ii) polycarbonates having a Tg of 160 to 250° C., preferably 170 to 230° C. and a water absorption coefficient of 0.10 to 0.30%, preferably 0.13 to 0.30%, more preferably 0.14 to 0.27%.

The water absorption coefficient of an aromatic polycarbonate is a value obtained by measuring the moisture percentage of a disk-like test specimen having a diameter of 45 mm and a thickness of 3.0 mm after the specimen is immersed in 23° C. water for 24 hours in accordance with ISO62-1980. Tg (glass transition temperature) is a value measured with a differential scanning calorimeter (DSC) in accordance with JIS K7121.

The carbonate precursor is a carbonyl halide, a diester carbonate or a haloformate. Examples thereof include phosgene, diphenyl carbonate and dihaloformates of a dihydric phenol.

For the manufacture of the aromatic polycarbonate from a dihydric phenol and a carbonate precursor by interfacial polymerization, a catalyst, an end-sealing agent and an antioxidant for preventing the oxidation of the dihydric phenol may be optionally used. The aromatic polycarbonate includes a branched polycarbonate obtained by copolymerizing a polyfunctional aromatic compound having 3 or more aromatic groups, a polyester carbonate obtained by copolymerizing an aromatic or aliphatic (including alicyclic) bifunctional carboxylic acid, a copolycarbonate obtained by copolymerizing a bifunctional alcohol (including an alicyclic bifunctional alcohol), and a polyester carbonate obtained by copolymerizing the bifunctional carboxylic acid and the bifunctional alcohol. It may also be a mixture of two or more of the obtained polycarbonates.

The branched polycarbonate increases the melt tension of the resin composition of the present invention so that its moldability by extrusion molding, foam molding or blow molding can be improved based on this characteristic property. As a result, a molded article having excellent dimensional accuracy is obtained by these molding methods.

Preferred examples of the polyfunctional aromatic compound having 3 or more aromatic groups used in the branched polycarbonate include trisphenols such as 4,6-dimethyl-2,4,6-tris(4-hydroxydiphenyl)heptene-2, 2,4,6-trimethyl-2,4,6-tris(4-hydroxyphenyl)heptane, 1,3,5-tris(4-hydroxyphenyl)benzene, 1,1,1-tris(4-hydroxyphenyl)ethane, 1,1,1-tris(3,5-dimethyl-4-hydroxyphenyl)ethane, 2,6-bis(2-hydroxy-5-methylbenzyl)-4-methylphenol and 4-{4-[1,1-bis(4-hydroxyphenyl)ethyl]benzene}-α,α-dimethylbenzylphenol. Other polyfunctional aromatic compounds include phloroglucin, phloroglucide, tetra(4-hydroxyphenyl)methane, bis(2,4-dihydroxyphenyl)ketone, 1,4-bis(4,4-dihydroxytriphenylmethyl)benzene, trimellitic acid, pyromellitic acid, benzophenone tetracarboxylic acid and acid chlorides thereof. Out of these, 1,1,1-tris(4-hydroxyphenyl)ethane and 1,1,1-tris(3,5-dimethyl-4-hydroxyphenyl)ethane are preferred, and 1,1,1-tris(4-hydroxyphenyl)ethane is particularly preferred.

The amount of the constituent unit derived from the polyfunctional aromatic compound in the branched polycarbonate is preferably 0.03 to 1 mol %, more preferably 0.07 to 0.7 mol %, particularly preferably 0.1 to 0.4 mol % based on 100 mol % of the total of the constituent unit derived from the dihydric phenol and the constituent unit derived from the polyfunctional aromatic compound.

The branched structural unit is derived from the polyfunctional aromatic compound and also may be derived without using the polyfunctional aromatic compound like a side reaction at the time of a melt transesterification reaction. The amount of the branched structure can be calculated by $^1$H-NMR measurement.

The aromatic polycarbonate (component A-β-3) may be a polyester carbonate obtained by copolymerizing an aromatic or aliphatic (including alicyclic) bifunctional carboxylic acid, a copolycarbonate obtained by copolymerizing a bifunctional alcohol (including an alicyclic bifunctional alcohol), or a polyester carbonate obtained by copolymerizing the bifunctional carboxylic acid and the bifunctional alcohol. It may also be a mixture of two or more of the obtained polycarbonates.

The aliphatic bifunctional carboxylic acid is preferably α,ω-dicarboxylic acid. Preferred examples of the aliphatic bifunctional carboxylic acid include linear saturated aliphatic dicarboxylic acids such as sebacic acid (decanedioic acid), dodecanedioic acid, tetradecanedioic acid, octadecanedioic acid and icosanedioic acid, and alicyclic dicarboxylic acids such as cyclohexanedicarboxylic acid. The bifunctional alcohol is preferably an alicyclic diol such as cyclohexanedimethanol, cyclohexanediol or tricyclodecanedimethanol.

Further, a polycarbonate-polyorganosiloxane copolymer obtained by copolymerizing a polyorganosiloxane unit may also be used.

The aromatic polycarbonate (component A-β-3) may be a mixture of two or more different polycarbonates selected from polycarbonates obtained from the above different dihydric phenols, polycarbonates containing a branched component, polyester carbonates, and polycarbonate-polyorganosiloxane copolymers. Further, a mixture of two or more polycarbonates produced by different processes or polycarbonates obtained by using different end-sealing agents may also be used.

Reactions such as interfacial polymerization, melt transesterification, the solid-phase transesterification of a carbonate prepolymer and the ring-opening polymerization of a cyclic carbonate compound which are polycarbonate production processes are well known through various documents and patent publications.

The viscosity average molecular weight (M) of the aromatic polycarbonate (component A-β-3) is not particularly limited but preferably $1 \times 10^4$ to $5 \times 10^4$, more preferably $1.4 \times 10^4$ to $3 \times 10^4$, much more preferably $1.4 \times 10^4$ to $2.4 \times 10^4$. A polycarbonate having a viscosity average molecular weight lower than $1 \times 10^4$ may not have practically high toughness and cracking resistance. A resin composition obtained from a polycarbonate having a viscosity average molecular weight higher than $5 \times 10^4$ is inferior in general applicability as it generally requires a high molding temperature or a special molding method. A high molding temperature tends to cause the deterioration of the deformation characteristic or rheology characteristic of a resin composition.

The above polycarbonate may be obtained by mixing a polycarbonate having a viscosity average molecular weight outside the above range. Especially a polycarbonate having a viscosity average molecular weight higher than the above value ($5 \times 10^4$) increases the melt tension of the resin composition of the present invention so that its moldability by extrusion molding, foam molding or blow molding can be improved based on this characteristic property. This improving effect is better than that of the above branched polycarbonate.

According to a more preferred aspect, as the component A-β-3 may be used an aromatic polycarbonate (I) which consists of an aromatic polycarbonate having a viscosity average molecular weight of $7 \times 10^4$ to $3 \times 10^5$ (component I-1) and an aromatic polycarbonate having a viscosity average molecular weight of $1 \times 10^4$ to $3 \times 10^4$ (component I-2) and which has a viscosity average molecular weight of $1.6 \times 10^4$ to $3.5 \times 10^4$ (to be referred to as "high molecular weight component-containing aromatic polycarbonate" hereinafter).

In the high molecular weight component-containing aromatic polycarbonate (component I), the molecular weight of the component I-1 is preferably $7 \times 10^4$ to $2 \times 10^5$, more preferably $8 \times 10^4$ to $2 \times 10^5$, much more preferably $1 \times 10^5$ to $2 \times 10^5$, particularly preferably $1 \times 10^5$ to $1.6 \times 10^5$. The molecular weight of the component I-2 is preferably $1.0 \times 10^4$ to $2.5 \times 10^4$, more preferably $1.1 \times 10^4$ to $2.4 \times 10^4$, much more preferably $1.2 \times 10^4$ to $2.4 \times 10^4$, particularly preferably $1.2 \times 10^4$ to $2.3 \times 10^4$.

The high molecular weight component-containing aromatic polycarbonate (component I) can be obtained by mixing together the above components I-1 and 1-2 and adjusting them to satisfy the predetermined molecular weight range. Preferably, the amount of the component I-1 is preferably 2 to 40 wt %, more preferably 3 to 30 wt %, much more preferably 4 to 20 wt %, particularly preferably 5 to 20 wt % based on 100 wt % of the component I.

Examples of the method of preparing the component I include (1) one in which the components I-1 and I-2 are polymerized independently and the obtained polymers are mixed together, (2) one typified by a method disclosed by JP-A 5-306336 in which a method of producing an aromatic polycarbonate showing a plurality of polymer peaks in a molecular weight distribution chart by a GPC method in the same system is used to produce the aromatic polycarbonate in such a manner that the conditions of the component I of the present invention are satisfied and (3) one in which an aromatic polycarbonate obtained by the above method (2) and the component I-1 and/or the component I-2 produced separately are mixed together.

The term "viscosity average molecular weight (M)" as used herein is obtained as follows. The specific viscosity ($\eta_{sp}$) of a solution prepared by dissolving 0.7 g of a polycarbonate in 100 ml of methylene chloride at 20° C. is first obtained from the following equation by using an Ostwald's viscometer, and the viscosity average molecular weight M is calculated from the obtained specific viscosity ($\eta_{sp}$) based on the following equation.

Specific viscosity $(\eta_{sp}) = (t - t_0)/t_0$

[$t_0$ is the number of seconds during which methylene chloride drops and t is the number of seconds during which the sample solution drops]

$\eta_{sp}/c = [\eta] + 0.45 \times [\eta]^2 c$ ([η] is an intrinsic viscosity)

$[\eta] = 1.23 \times 10^{-4} M^{0.83}$ $c = 0.7$

To calculate the viscosity average molecular weight in the resin composition of the present invention, the following procedure is taken. That is, the resin composition is mixed with methylene chloride in a weight ratio of 1:20 to 1:30 to dissolve soluble matter contained in the resin composition. The soluble matter is collected by cerite filtration. Thereafter, the solvent contained in the obtained solution is removed. The solid after the removal of the solvent is dried completely so as to obtain a methylene chloride-soluble solid. 0.7 g of the solid is dissolved in 100 ml of methylene chloride to measure the specific viscosity of the obtained solution at 20° C. in the same manner as above so as to calculate its viscosity average molecular weight M from the above specific viscosity in the same manner as above.

A recycled aromatic polycarbonate may be used as the aromatic polycarbonate (component A-β-3). In this case, the total content of components having a low environmental burden including the polylactic acid (component A-α) which is a non-oil resource material increases and therefore, this aromatic polycarbonate becomes a preferred material from the viewpoint of the effect of reducing an environmental burden. The recycled aromatic polycarbonate refers to a resin which is recovered from a resin molded article formed by at least a processing step for the production of a product of interest without a polymer decomposition step. Typical examples of the recycled aromatic polycarbonate include resins obtained from resin molded articles separated and collected from used products, resin molded articles separated and collected from defective products which are produced at the time of manufacturing products and resin molded articles which are unwanted parts such as spool runners produced at the time of molding.

The decomposition step means a step for recovering a monomer or an oligomer produced by decomposing the bond forming the main chain of an aromatic polycarbonate and does not mean heat decomposition in a step for kneading, grinding or processing.

Meanwhile, a so-called virgin aromatic polycarbonate is generally a resin which is an in-house product or a resin acquired from the market and may be in a powdery, pellet, chip or globular form. A recycled aromatic polycarbonate which contains preferably 90 wt % or more, more preferably 95 wt % or more, much more preferably 98 wt % or more of an aromatic polycarbonate component based on 100 wt % of the resin material is used.

Preferred examples of the above used products include glazing materials typified by soundproof walls, glass windows, translucent roof materials and car sunroofs, transparent members such as windshields and car head lamp lenses, containers such as water bottles, and optical recording media. They do not contain large amounts of additives and other resins, and target quality is easily obtained from them. Transparent polycarbonate molded articles having a hard coat film on the surface are particularly preferred. This is because these molded articles are often colored by the influence of a hard coating agent though they have high transparency. Examples of the molded articles include glazing materials and transparent members such as windshields and car head lamp lenses.

As the recycled aromatic polycarbonate may be used ground products of the above unwanted resin molded articles and pellets produced by re-melting and extruding the ground products. Further, when the resin molded articles have a printed film, a seal, a label, a decorative coating film, a conductive coating film, a conductive plating film or a deposited metal film, ground products from which these parts have been removed (may be ground after removal or removed after grinding) and pellets produced by re-melting and extruding the ground products can be used.

Since the recycled aromatic polycarbonate is easily colored by the influence of the printed film when it contains the printed film, it is difficult to obtain the effect of the present invention completely. Therefore, it is preferred in the present invention that the printed film should be removed. To remove the printed film or the plating film, a method such as rolling between two rolls, contact with heated and pressurized water, a solvent, or an acid alkali aqueous solution, mechanical chipping-off of a part to be removed, the application of ultraviolet waves and a blast treatment may be employed. A combination thereof may also be used.

Since a good color can be obtained in a transparent polycarbonate molded article having a hard coat film on the surface, it is more efficient to use a ground product thereof as it is, thereby contributing to the reduction of the environmental burden. The ground product can be produced by grinding a resin molded article by means of a known grinder.

The recycled aromatic polycarbonate may be contained in an amount of preferably 5 wt % or more, more preferably 10 wt % or more, much more preferably 15 wt % or more based on 100 wt % of the aromatic polycarbonate as the component A-β-3. Although the upper limit can be 100 wt %, when the amount of the recycled aromatic polycarbonate is 50 wt % or lower, a resin composition having stable characteristic properties is obtained advantageously.

As for the ratio of the polylactic acid (component A-α) and the aromatic polycarbonate (component A-β-3), preferably, the amount of the polylactic acid (component A-α) is 5 to 95 wt % and the amount of the aromatic polycarbonate (component A-β-3) is 95 to 5 wt %. More preferably, the amount of the polylactic acid (component A-α) is 25 to 95 wt % and the amount of the aromatic polycarbonate (component A-β-3) is 75 to 5 wt %. Much more preferably, the amount of the polylactic acid (component A-α) is 50 to 95 wt % and the amount of the aromatic polycarbonate (component A-β-3) is 50 to 5 wt %. When the amount of the aromatic polycarbonate (component A-β-3) is 95 wt % or more, the effect of reducing the environmental burden is small and when the amount of the aromatic polycarbonate (component A-β-3) is 5 wt % or less, the effect of improving hydrolysis resistance and mechanical properties is not obtained.

<Component B: Cyclic Carbodiimide Compound>

The cyclic carbodiimide compound (component B) has a cyclic structure. The cyclic carbodiimide compound may have a plurality of cyclic structures.

The cyclic structure has one carbodiimide group (—N=C=N—), and the first nitrogen and second nitrogen of the carbodiimide group are bonded to each other via a bonding group. Each cyclic structure has only one carbodiimide group.

The number of atoms in the cyclic structure is 8 to 50, preferably 10 to 30, more preferably 10 to 20, much more preferably 10 to 15, most preferably 10 to 14.

The number of atoms in the cyclic structure means the number of atoms directly constituting the cyclic structure. For example, when the cyclic structure is an 8-membered ring, the number of atoms is 8 and when the cyclic structure is a 50-membered ring, the number of atoms is 50. When the number of atoms in the cyclic structure is smaller than 8, the stability of the cyclic carbodiimide compound lowers, thereby making it difficult to store and use the cyclic carbodiimide compound. Although the upper limit of the number of atoms is not particularly limited from the viewpoint of reactivity, it is difficult to synthesize a cyclic carbodiimide compound having a cyclic structure with more than 50 atoms and its cost may significantly rise. From this point of view, the number of atoms in the cyclic structure is preferably 10 to 30, more preferably 10 to 20, much more preferably 10 to 15, most preferably 10 to 14.

The cyclic structure is represented by the following formula (5).

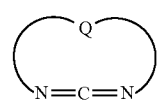

(5)

In the above formula, Q is a divalent to tetravalent bonding group represented by the following formula (5-1), (5-2) or (5-3).

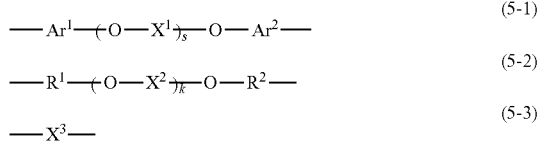

$$—Ar^1—(O—X^1)_s—O—Ar^2— \quad (5\text{-}1)$$

$$—R^1—(O—X^2)_k—O—R^2— \quad (5\text{-}2)$$

$$—X^3— \quad (5\text{-}3)$$

In the above formulas, $Ar^1$ and $Ar^2$ are each independently a divalent to tetravalent aromatic group having 5 to 15 carbon atoms which may contain a hetero atom and a substituent.

Examples of the aromatic group include arylene group having 5 to 15 carbon atoms, arenetriyl group having 5 to 15 carbon atoms and arenetetrayl group having 5 to 15 carbon atoms, all of which may have a heterocyclic structure with a hetero atom. Examples of the arylene group (divalent) include phenylene group and naphthalenediyl group. Examples of the arenetriyl group (trivalent) include benzenetriyl group and naphthalenetriyl group. Examples of the arenetetrayl group (tetravalent) include benzenetetrayl group and naphthalenetetrayl group. These aromatic groups may be substituted. Examples of the substituent include alkyl group having 1 to 20 carbon atoms, aryl group having 6 to 15 carbon atoms, halogen atom, nitro group, amido group, hydroxyl group, ester group, ether group and aldehyde group.

$R^1$ and $R^2$ are each independently a divalent to tetravalent aliphatic group having 1 to 20 carbon atoms, a divalent to tetravalent alicyclic group having 3 to 20 carbon atoms, a combination thereof, or a combination of the aliphatic group, the alicyclic group and a divalent to tetravalent aromatic group having 5 to 15 carbon atoms, all of which may contain a hetero atom and a substituent.

Examples of the aliphatic group include alkylene group having 1 to 20 carbon atoms, alkanetriyl group having 1 to 20 carbon atoms and alkanetetrayl group having 1 to 20 carbon atoms. Examples of the alkylene group include methylene group, ethylene group, propylene group, butylene group, pentylene group, hexylene group, heptylene group, octylene group, nonylene group, decylene group, dodecylene group and hexadecylene group. Examples of the alkanetriyl group include methanetriyl group, ethanetriyl group, propanetriyl group, butanetriyl group, pentanetriyl group, hexanetriyl group, heptanetriyl group, octanetriyl group, nonanetriyl group, decanetriyl group, dodecanetriyl group and hexadecanetriyl group. Example of the alkanetetrayl group include methanetetrayl group, ethanetetrayl group, propanetetrayl group, butanetetrayl group, pentanetetrayl group, hexanetetrayl group, heptanetetrayl group, octanetetrayl group, nonanetetrayl group, decanetetrayl group, dodecanetetrayl group and hexadecanetetrayl group. These aliphatic groups may be substituted. Examples of the substituent include alkyl group having 1 to 20 carbon atoms, aryl group having 6 to 15 carbon atoms, halogen atom, nitro group, amido group, hydroxyl group, ester group, ether group and aldehyde group.

Examples of the alicyclic group include cycloalkylene group having 3 to 20 carbon atoms, cycloalkanetriyl group having 3 to 20 carbon atoms and cycloalkanetetrayl group having 3 to 20 carbon atoms. Examples of the cycloalkylene group include cyclopropylene group, cyclobutylene group, cyclopentylene group, cyclohexylene group, cycloheptylene group, cyclooctylene group, cyclononylene group, cyclodecylene group, cyclododecylene group and cyclohexadecylene group. Examples of the cycloalkanetriyl group include cyclopropanetriyl group, cyclobutanetriyl group, cyclopentanetriyl group, cyclohexanetriyl group, cycloheptanetriyl group, cyclooctanetriyl group, cyclononanetriyl group, cyclodecanetriyl group, cyclododecanetriyl group and cyclohexadecanetriyl group. Examples of the cycloalkanetetrayl group include cyclopropanetetrayl group, cyclobutanetetrayl group, cyclopentanetetrayl group, cyclohexanetetrayl group, cycloheptanetetrayl group, cyclooctanetetrayl group, cyclononanetetrayl group, cyclodecanetetrayl group, cyclododecanetetrayl group and cyclohexadecanetetrayl group. These alicyclic groups may be substituted. Examples of the substituent include alkyl group having 1 to 20 carbon atoms, aryl group having 6 to 15 carbon atoms, halogen atom, nitro group, amido group, hydroxyl group, ester group, ether group and aldehyde group.

Examples of the aromatic group include arylene group having 5 to 15 carbon atoms, arenetriyl group having 5 to 15 carbon atoms and arenetetrayl group having 5 to 15 carbon atoms, all of which may have a heterocyclic structure with a hetero atom. Examples of the arylene group include phenylene group and naphthalenediyl group. Examples of the arenetriyl group (trivalent) include benzenetriyl group and naphthalenetriyl group. Examples of the arenetetrayl group (tetravalent) include benzenetetrayl group and naphthalenetetrayl group. These aromatic groups may be substituted. Examples of the substituent include alkyl group having 1 to 20 carbon atoms, aryl group having 6 to 15 carbon atoms, halogen atom, nitro group, amido group, hydroxyl group, ester group, ether group and aldehyde group.

$X^1$ and $X^2$ are each independently a divalent to tetravalent aliphatic group having 1 to 20 carbon atoms, a divalent to tetravalent alicyclic group having 3 to 20 carbon atoms, a divalent to tetravalent aromatic group having 5 to 15 carbon atoms or a combination thereof, all of which may contain a hetero atom and a substituent.

Examples of the aliphatic group include alkylene group having 1 to 20 carbon atoms, alkanetriyl group having 1 to 20 carbon atoms and alkanetetrayl group having 1 to 20 carbon atoms. Examples of the alkylene group include methylene group, ethylene group, propylene group, butylene group, pentylene group, hexylene group, heptylene group, octylene group, nonylene group, decylene group, dodecylene group and hexadecylene group. Examples of the alkanetriyl group include methanetriyl group, ethanetriyl group, propanetriyl group, butanetriyl group, pentanetriyl group, hexanetriyl group, heptanetriyl group, octanetriyl group, nonanetriyl group, decanetriyl group, dodecanetriyl group and hexadecanetriyl group. Example of the alkanetetrayl group include methanetetrayl group, ethanetetrayl group, propanetetrayl group, butanetetrayl group, pentanetetrayl group, hexanetetrayl group, heptanetetrayl group, octanetetrayl group, nonanetetrayl group, decanetetrayl group, dodecanetetrayl group and hexadecanetetrayl group. These aliphatic groups may be substituted. Examples of the substituent include alkyl group having 1 to 20 carbon atoms, aryl group having 6 to 15 carbon atoms, halogen atom, nitro group, amido group, hydroxyl group, ester group, ether group and aldehyde group.

Examples of the alicyclic group include cycloalkylene group having 3 to 20 carbon atoms, cycloalkanetriyl group having 3 to 20 carbon atoms and cycloalkanetetrayl group having 3 to 20 carbon atoms. Examples of the cycloalkylene group include cyclopropylene group, cyclobutylene group, cyclopentylene group, cyclohexylene group, cycloheptylene group, cyclooctylene group, cyclononylene group, cyclodecylene group, cyclododecylene group and cyclohexadecylene group. Examples of the alkanetriyl group include cyclopropanetriyl group, cyclobutanetriyl group, cyclopentanetriyl group, cyclohexanetriyl group, cycloheptanetriyl group, cyclooctanetriyl group, cyclononanetriyl group, cyclodecanetriyl group, cyclododecanetriyl group and cyclohexadecanetriyl group. Examples of the cycloalkanetetrayl group include cyclopropanetetrayl group, cyclobutanetetrayl group, cyclopentanetetrayl group, cyclohexanetetrayl group, cycloheptanetetrayl group, cyclooctanetetrayl group, cyclononanetetrayl group, cyclodecanetetrayl group, cyclododecanetetrayl group and cyclohexadecanetetrayl group. These alicyclic groups may be substituted. Examples of the substituent include alkyl group having 1 to 20 carbon atoms, aryl group having 6 to 15 carbon atoms, halogen atom, nitro group, amido group, hydroxyl group, ester group, ether group and aldehyde group.

Examples of the aromatic group include arylene group having 5 to 15 carbon atoms, arenetriyl group having 5 to 15 carbon atoms and arenetetrayl group having 5 to 15 carbon atoms, all of which may have a heterocyclic structure with a hetero atom. Examples of the arylene group include phenylene group and naphthalenediyl group. Examples of the arenetriyl group (trivalent) include benzenetriyl group and naphthalenetriyl group. Examples of the arenetetrayl group (tetravalent) include benzenetetrayl group and naphthalenetetrayl group. These aromatic groups may be substituted. Examples of the substituent include alkyl group having 1 to 20 carbon atoms, aryl group having 6 to 15 carbon atoms, halogen atom, nitro group, amido group, hydroxyl group, ester group, ether group and aldehyde group.

In the formulas (5-1) and (5-2), s and k are each independently an integer of 0 to 10, preferably 0 to 3, more preferably 0 to 1. When s and k are larger than 10, it is difficult to synthesize the cyclic carbodiimide compound, thereby greatly boosting its cost. From this point of view, the integer is preferably selected from a range of 0 to 3. When s or k is 2 or more, $X^1$ or $X^2$ as a recurring unit may be different from another $X^1$ or $X^2$, respectively.

$X^3$ is a divalent to tetravalent aliphatic group having 1 to 20 carbon atoms, a divalent to tetravalent alicyclic group having 3 to 20 carbon atoms, a divalent to tetravalent aromatic group having 5 to 15 carbon atoms or a combination thereof, all of which may contain a hetero atom and a substituent.

Examples of the aliphatic group include alkylene group having 1 to 20 carbon atoms, alkanetriyl group having 1 to 20 carbon atoms and alkanetetrayl group having 1 to 20 carbon atoms. Examples of the alkylene group include methylene group, ethylene group, propylene group, butylene group, pentylene group, hexylene group, heptylene group, octylene group, nonylene group, decylene group, dodecylene group and hexadecylene group. Examples of the alkanetriyl group include methanetriyl group, ethanetriyl group, propanetriyl group, butanetriyl group, pentanetriyl group, hexanetriyl group, heptanetriyl group, octanetriyl group, nonanetriyl group, decanetriyl group, dodecanetriyl group and hexadecanetriyl group. Example of the alkanetetrayl group include methanetetrayl group, ethanetetrayl group, propanetetrayl group, butanetetrayl group, pentanetetrayl group, hexanetetrayl group, heptanetetrayl group, octanetetrayl group, nonanetetrayl group, decanetetrayl group, dodecanetetrayl group and hexadecanetetrayl group. These aliphatic groups may contain a substituent. Examples of the substituent include alkyl group having 1 to 20 carbon atoms, aryl group having 6 to 15 carbon atoms, halogen atom, nitro group, amido group, hydroxyl group, ester group, ether group and aldehyde group.

Examples of the alicyclic group include cycloalkylene group having 3 to 20 carbon atoms, cycloalkanetriyl group having 3 to 20 carbon atoms and cycloalkanetetrayl group having 3 to 20 carbon atoms. Examples of the cycloalkylene group include cyclopropylene group, cyclobutylene group, cyclopentylene group, cyclohexylene group, cycloheptylene group, cyclooctylene group, cyclononylene group, cyclodecylene group, cyclododecylene group and cyclohexadecylene group. Examples of the alkanetriyl group include cyclopropanetriyl group, cyclobutanetriyl group, cyclopentanetriyl group, cyclohexanetriyl group, cycloheptanetriyl group, cyclooctanetriyl group, cyclononanetriyl group, cyclodecanetriyl group, cyclododecanetriyl group and cyclohexadecanetriyl group. Examples of the alkanetetrayl group include cyclopropanetetrayl group, cyclobutanetetrayl group, cyclopentanetetrayl group, cyclohexanetetrayl group, cycloheptanetetrayl group, cyclooctanetetrayl group, cyclononanetetrayl group, cyclodecanetetrayl group, cyclododecanetetrayl group and cyclohexadecanetetrayl group. These alicyclic groups may contain a substituent. Examples of the substituent include alkyl group having 1 to 20 carbon atoms, aryl group having 6 to 15 carbon atoms, halogen atom, nitro group, amido group, hydroxyl group, ester group, ether group and aldehyde group.

Examples of the aromatic group include arylene group having 5 to 15 carbon atoms, arenetriyl group having 5 to 15 carbon atoms and arenetetrayl group having 5 to 15 carbon atoms, all of which may have a heterocyclic structure with a hetero atom. Examples of the arylene group include phenylene group and naphthalenediyl group. Examples of the arenetriyl group (trivalent) include benzenetriyl group and naphthalenetriyl group. Examples of the arenetetrayl group (tetravalent) include benzenetetrayl group and naphthalenetetrayl group. These aromatic groups may be substituted. Examples of the substituent include alkyl group having 1 to 20 carbon atoms, aryl group having 6 to 15 carbon atoms, halogen atom, nitro group, amido group, hydroxyl group, ester group, ether group and aldehyde group.

$Ar^1$, $Ar^2$, $R^1$, $R^2$, $X^1$, $X^2$ and $X^3$ may contain a hetero atom. When Q is a divalent bonding group, $Ar^1$, $Ar^2$, $R^1$, $R^2$, $X^3$, $X^2$ and $X^3$ are all divalent groups. When Q is a trivalent bonding group, one of $Ar^1$, $Ar^2$, $R^1$, $R^2$, $X^1$, $X^2$ and $X^3$ is a trivalent group. When Q is a tetravalent bonding group, one of $Ar^1$, $Ar^2$, $R^1$, $R^2$, $X^1$, $X^2$ and $X^3$ is a tetravalent group, or two of them are trivalent groups.

Examples of the cyclic carbodiimide used in the present invention are (a) a cyclic carbodiimide of the formula (5) in which Q is a divalent bonding group, (b) a cyclic carbodiimide in which Q is a trivalent bonding group, and (c) a cyclic carbodiimide in which Q is a tetravalent bonding group.

<Cyclic Carbodiimide (a)>

The cyclic carbodiimide (a) in which Q is a divalent bonding group ($Q_a$) is represented by the following formula (6).

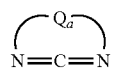

(6)

In the above formula, $Q_a$ is a divalent bonding group represented by the following formulas (6-1), (6-2) or (6-3).

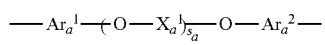 (6-1)

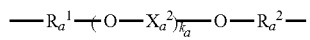 (6-2)

 (6-3)

(In the above formulas, $Ar_a^1$, $Ar_a^2$, $R_a^1$, $R_a^2$, $X_a^1$, $X_a^2$, $X_a^3$, $s_a$ and $k_a$ are identical to $Ar^1$, $Ar^2$, $R^1$, $R^2$, $X^1$, $X^2$, $X^3$, s and k in the above formulas (5-1) to (5-2), respectively. They are divalent groups.)

Examples of the cyclic carbodiimide compound (a) include the following compounds.

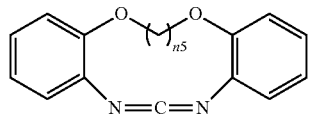

($n^5$=integer of 1 to 6)

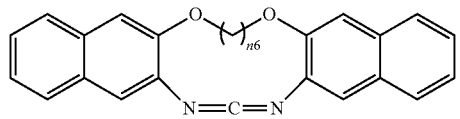

($n^6$=integer of 1 to 6)

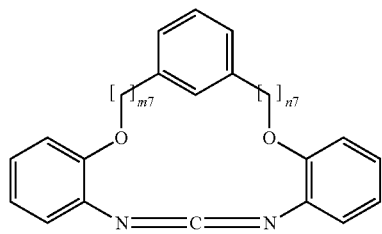

($m^7$ and $n^7$=integer of 0 to 3, respectively)

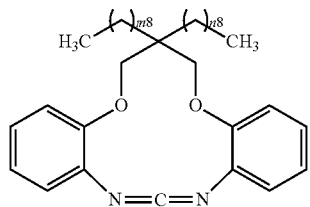

($m^8$ and $n^8$=integer of 0 to 5, respectively)

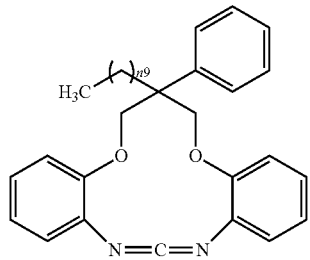

($n^9$=integer of 0 to 5)

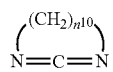

($n^{10}$=integer of 0 to 20)

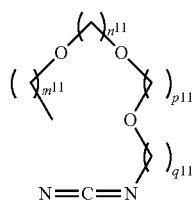

($m^{11}$, $n^{11}$, $p^{11}$ and $q^{11}$=integer of 1 to 6, respectively)

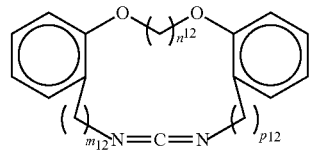

($m^{12}$, $n^{12}$ and $p^{12}$=integer of 1 to 6, respectively)

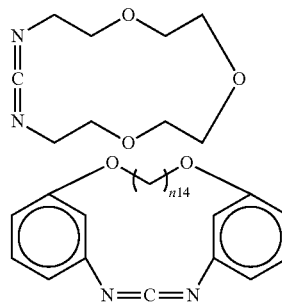

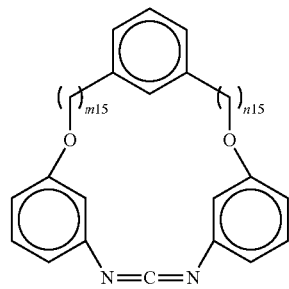

($n^{14}$=integer of 0 to 16)

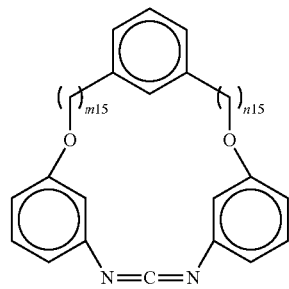

($m^{15}$ and $n^{15}$=integer of 0 to 3, respectively)

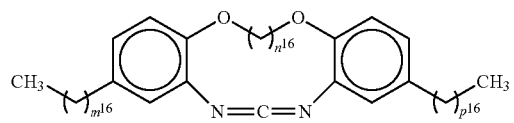

($m^{16}$ and $p^{16}$=integer of 1 to 5, $n^{16}$=integer of 1 to 6, respectively)

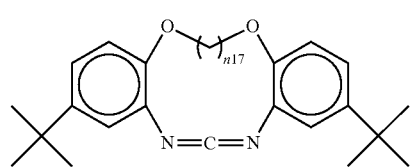

($n^{17}$=integer of 1 to 6)

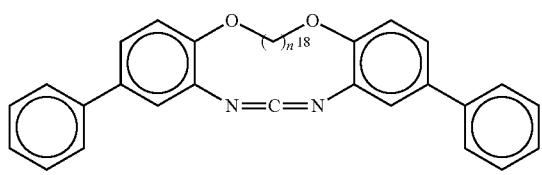

($n^{18}$=integer of 1 to 6)

<Cyclic Carbodiimide (b)>

The cyclic carbodiimide (b) in which Q is a trivalent bonding group ($Q_b$) is represented by the following formula (7).

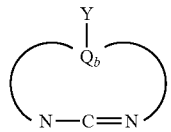 (7)

In the above formula, $Q_b$ is a trivalent bonding group represented by the following formulas, (7-1), (7-2) or (7-3), and Y is a carrier supporting a cyclic structure.

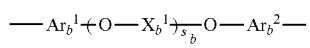 (7-1)

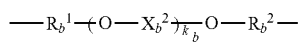 (7-2)

 (7-3)

In the above formulas, $Ar_b^1$, $Ar_b^2$, $R_b^1$, $R_b^2$, $X_b^1$, $X_b^2$, $X_b^3$, $s_b$ and $k_b$ are identical to $Ar^1$, $Ar^2$, $R^1$, $R^2$, $X^1$, $X^2$, $X^3$, s and k in the above formulas (5-1) to (5-3), respectively. One of these is a trivalent group.

Y is a single bond, double bond, atom, atom group or polymer. Y is a bond via which a plurality of cyclic structures are bonded together to form a structure represented by the formula (7). Examples of the cyclic carbodiimide compound (b) include the following compounds.

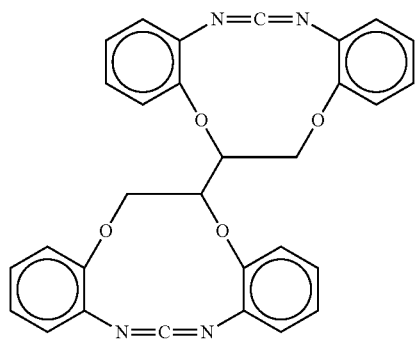

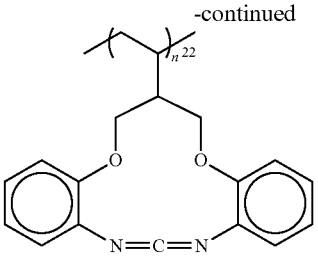

($n^{22}$=integer of 1 to 6)

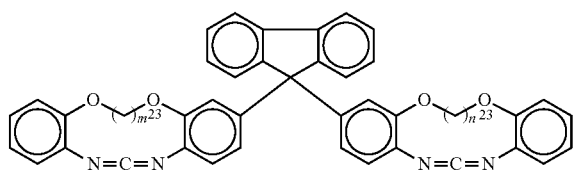

($m^{23}$ and $n^{23}$=integer of 1 to 6, respectively)

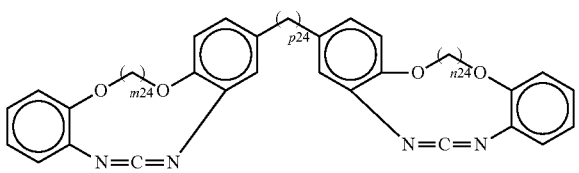

($m^{24}$, $n^{24}$ and $p^{24}$=integer of 1 to 6, respectively)

<Cyclic Carbodiimide (c)>

The cyclic carbodiimide (c) in which Q is a tetravalent bonding group ($Q_c$) is represented by the following formula (8).

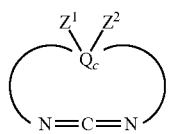 (8)

In the above formula, $Q_c$ is a tetravalent bonding group represented by the following formulas (8-1), (8-2) or (8-3), and $Z^1$ and $Z^2$ are carriers supporting a cyclic structure. $Z^1$ and $Z^2$ may be bonded together to form a cyclic structure.

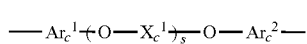 (8-1)

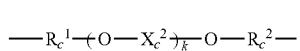 (8-2)

 (8-3)

$Ar_c^1$, $Ar_c^2$, $R_c^1$, $R_c^2$, $X_c^1$, $X_c^2$, $X_c^3$, $s_c$ and $k_c$ are identical to $Ar^1$, $Ar^2$, $R^1$, $R^2$, $X^1$, $X^2$, $X^3$, s and k in the above formulas (5-1) to (5-3), respectively. One of $Ar_c^1$, $Ar_c^2$, $R_c^1$, $R_c^2$, $X_c^1$, $X_c^2$ and $X_c^3$ is a tetravalent group, or two of them are trivalent groups.

$Z^1$ and $Z^2$ are each independently a single bond, double bond, atom, atom group or polymer. $Z^1$ and $Z^2$ are each a bond via which a plurality of cyclic structures are bonded together to form a structure represented by the formula (8). Examples of the cyclic carbodiimide compound (c) include the following compounds.

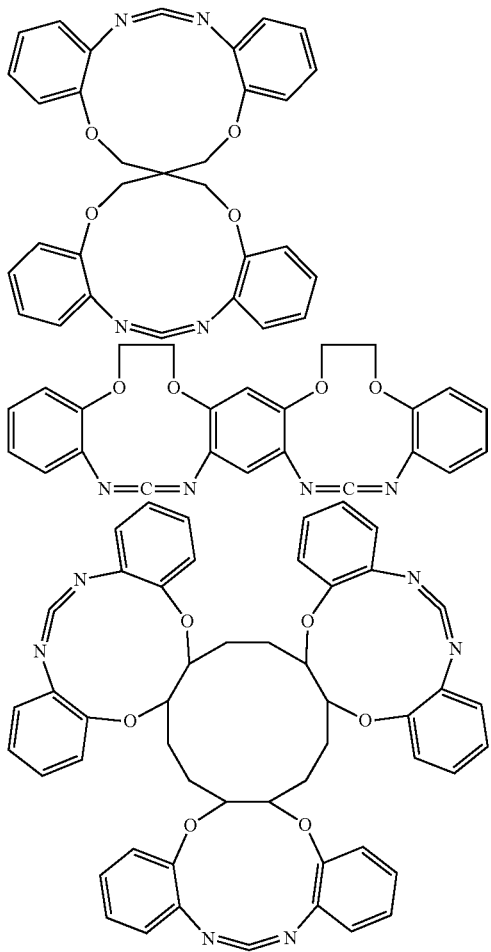

The content of the cyclic carbodiimide (component B) is 0.001 to 10 parts by weight, preferably 0.01 to 7 parts by weight, more preferably 0.1 to 5 parts by weight based on 100 parts by weight of the resin component (component A). When the content of the cyclic carbodiimide compound (component B) is lower than 0.001 part by weight, a satisfactory hydrolysis resistance improving effect is not obtained as the number of carbodiimide groups of the cyclic carbodiimide is too small as compared with the amount of the terminal group of the resin component (component A). When the content of the cyclic carbodiimide compound is higher than 10 parts by weight, hydrolysis resistance is degraded.

Although the cyclic carbodiimide compound (component B) added to the resin reacts with the terminal carboxyl group of the resin, a surplus cyclic carbodiimide compound (component B) remains unreacted in the resin composition. The content of the component B of the present invention is the amount of the cyclic carbodiimide compound remaining in the resin.

The component B remaining in the resin composition reacts with a terminal carboxyl group produced by the hydrolysis of the resin to suppress the hydrolysis of the resin. At this point, an isocyanate compound is not released, thereby giving off no terrible smell.

<Production Process of Cyclic Carbodiimide Compound>

The cyclic carbodiimide compound (component B) can be produced by a conventionally known process. Examples of the production process include one in which the cyclic carbodiimide compound is produced from an amine derivative through an isocyanate derivative, one in which the cyclic carbodiimide compound is produced from an amine derivative through an isothiocyanate derivative, one in which the cyclic carbodiimide compound is produced from an amine derivative through a triphenylphosphine derivative, one in which the cyclic carbodiimide compound is produced from an amine derivative through an urea derivative, one in which the cyclic carbodiimide compound is produced from an amine derivative through a thiourea derivative, one in which the cyclic carbodiimide compound is produced from a carboxylate derivative through an isocyanate derivative and one in which the cyclic carbodiimide compound is produced by deriving a lactam derivative.

The cyclic carbodiimide compound of the present invention may be produced by combining or modifying the processes described in the following documents from which a suitable one may be employed according to a compound to be produced.

(1) Tetrahedron Letters, Vol. 34, No. 32, 5155-5158, 1993. Medium- and Large-Membered Rings from Bis(iminophosphoranes): An Efficient Preparation of Cyclic Carbodiimides, Pedro Molina et al.

(2) Journal of Organic Chemistry, Vol. 61, No. 13, 4289-4299, 1996. New Models for the Study of the Racemization Mechanism of Carbodiimides. Synthesis and Structure (X-ray Crystallography and 1H NMR) of Cyclic Carbodiimides, Pedro Molina et al.

(3) Journal of Organic Chemistry, Vol. 43, No. 8, 1544-1546, 1978. Macrocyclic Ureas as Masked Isocyanates, Henri Ulrich et al.

(4) Journal of Organic Chemistry, Vol. 48, No. 10, 1694-1700, 1983. Synthesis and Reactions of Cyclic Carbodiimides, R. Richter et al.

(5) Journal of Organic Chemistry, Vol. 59, No. 24, 7306-7315, 1994. A New and Efficient Preparation of Cyclic Carbodiimides from Bis(iminophosphoranea) and the System $Boc_2O/DMAP$, Pedro Molina et al. A suitable process may be employed according to a compound to be produced. For example, a cyclic carbodiimide compound produced through the following steps can be advantageously used as the cyclic carbodiimide compound used in the present invention:

(1) reacting a nitrophenol represented by the following formula (a-1), a nitrophenol represented by the following formula (a-2) and a compound represented by the following formula (b) to obtain a nitro derivative represented by the following formula (c);

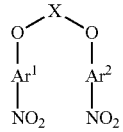

(2) reducing the obtained nitro derivative to obtain an amine derivative represented by the following formula (d);

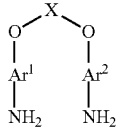
(d)

(3) reacting the obtained amine derivative with triphenylphosphine dibromide to obtain a triphenylphosphine derivative represented by the following formula (e); and

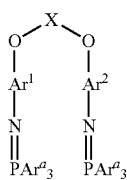
(e)

(4) isocyanating the obtained triphenylphosphine derivative in a reaction system and decarbonizing it directly.

In the above formulas, $Ar^1$ and $Ar^2$ are each independently an aromatic group which may be substituted by an alkyl group having 1 to 6 carbon atoms or a phenyl group. $E^1$ and $E^2$ are each independently a group selected from the group consisting of halogen atom, toluenesulfonyloxy group, methanesulfonyloxy group, benzenesulfonyloxy group and p-bromobenzenesulfonyloxy group. $Ar^a$ is a phenyl group. X is a bonding group represented by the following formulas (i-1), (i-2) or (i-3).

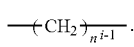
(i-1)

(In the above formula, $n^{i-1}$ is an integer of 1 to 6.)

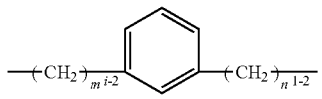
(i-2)

(In the above formula, $m^{i-2}$ and $n^{i-2}$ are each independently an integer of 0 to 3.)

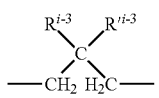
(i-3)

(In the above formula, $R^{i-3}$ and $R'^{i-3}$ are each independently an alkyl group having 1 to 6 carbon atoms or phenyl group.)

<Component C: Antioxidant>

The resin composition of the present invention comprises at least one selected from the group consisting of a hindered phenol-based compound, a phosphite-based compound, a phosphonite-based compound and a thioether-based compound as an antioxidant (component C). When the resin composition comprises an antioxidant (component C), its color and flowability at the time of molding are stabilized and also its hydrolysis resistance is improved.

Examples of the hindered phenol-based compound include α-tocopherol, butylhydroxytoluene, sinapyl alcohol, vitamin E, n-octadecyl-β-(4'-hydroxy-3',5'-di-tert-butylphenyl) propionate, 2-tert-butyl-6-(3'-tert-butyl-5'-methyl-2'-hydroxybenzyl)-4-methylphenyl acrylate, 2,6-di-tert-butyl-4-(N,N-dimethylaminomethyl)phenol, 3,5-di-tert-butyl-4-hydroxybenzylphosphonate diethyl ester, 2,2'-methylenebis(4-methyl-6-tert-butylphenol), 2,2'-methylenebis(4-ethyl-6-tert-butylphenol), 4,4'-methylenebis(2,6-di-tert-butylphenol), 2,2'-methylenebis(4-methyl-6-cyclohexylphenol), 2,2'-dimethylene-bis(6-α-methyl-benzyl-p-cresol), 2,2'-ethylidene-bis(4,6-di-tert-butylphenol), 2,2'-butylidene-bis(4-methyl-6-tert-butylphenol), 4,4'-butylidene-bis(3-methyl-6-tert-butylphenol), triethylene glycol-N-bis-3-(3-tert-butyl-4-hydroxy-5-methylphenyl)propionate, 1,6-hexanediol-bis[3-(3,5-di-tert-butyl-4-hydroxyphenyl) propionate], bis[2-tert-butyl-4-methyl-6-(3-tert-butyl-5-methyl-2-hydroxybenzyl) phenyl]terephthalate, 3,9-bis{2-[3-(3-tert-butyl-4-hydroxy-5-methylphenyl) propionyloxy]-1,1-dimethylethyl}-2,4,8,10-tetraoxaspiro[5,5]undecane, 4,4'-thiobis(6-tert-butyl-m-cresol), 4,4'-thiobis(3-methyl-6-tert-butylphenol), 2,2'-thiobis(4-methyl-6-tert-butylphenol), bis(3,5-di-tert-butyl-4-hydroxybenzyl)sulfide, 4,4'-di-thiobis(2,6-di-tert-butylphenol), 4,4'-tri-thiobis(2,6-di-tert-butylphenol), 2,2-thiodiethylenebis-[3-(3,5-di-tert-butyl-4-hydroxyphenyl) propionate], 2,4-bis(n-octylthio)-6-(4-hydroxy-3',5'-di-tert-butylanilino)-1,3,5-triazine, N,N'-hexamethylenebis-(3,5-di-tert-butyl-4-hydroxyhydrocinnamide), N,N'-bis[3-(3,5-di-tert-butyl-4-hydroxyphenyl)propionyl] hydrazine, 1,1,3-tris(2-methyl-4-hydroxy-5-tert-butylphenyl)butane, 1,3,5-trimethyl-2,4,6-tris(3,5-di-tert-butyl-4-hydroxybenzyl) benzene, tris(3,5-di-tert-butyl-4-hydroxyphenyl) isocyanurate, tris(3,5-di-tert-butyl-4-hydroxybenzyl) isocyanurate, 1,3,5-tris(4-tert-butyl-3-hydroxy-2,6-dimethylbenzyl) isocyanurate, 1,3,5-tris-2[3(3,5-di-tert-butyl-4-hydroxyphenyl) propionyloxy]ethyl isocyanurate and tetrakis[methylene-3-(3',5'-di-tert-butyl-4-hydroxyphenyl)propionate]methane.

Out of the above compounds, tetrakis[methylene-3-(3-tert-butyl-4-hydroxy-5-methylphenyl)propionate]methane, octadecyl-3-(3,5-di-tert-butyl-4-hydroxyphenyl) propionate and 3,9-bis[2-{3-(3-tert-butyl-4-hydroxy-5-methylphenyl) propionyloxy}-1,1-dimethylethyl]-2,4,8,10-tetraoxaspiro[5,5]undecane are preferably used in the present invention. Octadecyl-3-(3,5-di-tert-butyl-4-hydroxyphenyl) propionate is particularly preferred. All of them are easily acquired. The above hindered phenol-based compounds may be used alone or in combination of two or more.

Examples of the phosphite-based compound include triphenyl phosphite, tris(nonylphenyl)phosphite, tridecyl phosphite, trioctyl phosphite, trioctadecyl phosphite, didecylmonophenyl phosphite, dioctylmonophenyl phosphite, diisopropylmonophenyl phosphite, monobutyldiphenyl phosphite, monodecyldiphenyl phosphite, monooctyldiphenyl phosphite, tris(diethylphenyl)phosphite, tris(di-iso-propylphenyl)phosphite, tris(di-n-butylphenyl)phosphite, tris (2,4-di-tert-butylphenyl)phosphite, tris(2,6-di-tert-butylphenyl)phosphite, distearyl pentaerythritol diphosphite, bis(2,4-di-tert-butylphenyl)pentaerythritol diphosphite, bis(2,6-di-tert-butyl-4-methylphenyl)pentaerythritol diphosphite, bis(2,6-di-tert-butyl-4-ethylphenyl) pentaerythritol diphosphite, bis{2,4-bis(1-methyl-1-phenyl-ethyl)phenyl} pentaerythritol diphosphite, phenyl bisphenol A pentaerythritol diphosphite, bis(nonylphenyl)pentaerythritol diphosphite and dicyclohexyl pentaerythritol diphosphite.

Other phosphite-based compounds which react with a dihydric phenol to have a cyclic structure may also be used. Examples thereof include 2,2'-methylenebis(4,6-di-tert-butylphenyl)(2,4-di-tert-butylphenyl)phosphite, 2,2'-methylenebis(4,6-di-tert-butylphenyl)(2-tert-butyl-4-methylphenyl)phosphite and 2,2'-methylenebis(4,6-di-tert-butylphenyl)octyl phosphite. Out of these, distearyl pentaerythritol diphosphite, bis(2,4-di-tert-butylphenyl)pentaerythritol diphosphite, bis(2,6-di-tert-butyl-4-methylphenyl)pentaerythritol diphosphite and bis {2,4-bis (1-methyl-1-phenylethyl)phenyl} pentaerythritol diphosphite are particularly preferred. All of them are easily acquired. The above phosphite-based compounds may be used alone or in combination of two or more.

Examples of the phosphonite-based compound include tetrakis(2,4-di-tert-butylphenyl)-4,4'-biphenylene diphosphonite, tetrakis(2,4-di-tert-butylphenyl)-4,3'-biphenylene diphosphonite, tetrakis(2,4-di-tert-butylphenyl)-3,3'-biphenylene diphosphonite, tetrakis(2,6-di-tert-butylphenyl)-4,4'-biphenylene diphosphonite, tetrakis(2,6-di-tert-butylphenyl)-4,3'-biphenylene diphosphonite, tetrakis(2,6-di-tert-butylphenyl)-3,3'-biphenylene diphosphonite, bis(2,4-di-tert-butylphenyl)-4-phenyl-phenyl phosphonite, bis(2,4-di-tert-butylphenyl)-3-phenyl-phenyl phosphonite, bis(2,6-di-n-butylphenyl)-3-phenyl-phenyl phosphonite, bis(2,6-di-tert-butylphenyl)-4-phenyl-phenyl phosphonite and bis(2,6-di-tert-butylphenyl)-3-phenyl-phenyl phosphonite.

Out of these, tetrakis(di-tert-butylphenyl)-biphenylene diphosphonites and bis(di-tert-butylphenyl)-phenyl-phenyl phosphonites are preferred, and tetrakis(2,4-di-tert-butylphenyl)-biphenylene diphosphonites and bis(2,4-di-tert-butylphenyl)-phenyl-phenyl phosphonites are more preferred. The phosphonite-based compound may be and is preferably used in combination with the above phosphite-based compound having an aryl group substituted by two or more alkyl groups.

Tetrakis(2,4-di-tert-butylphenyl)-biphenylene diphosphonites are preferred as the phosphonite-based compound, and stabilizers comprising this phosphonite as the main component are marketed under the trade names of Sandostab P-EPQ (of Clariant Co., Ltd.) and Irgafos P-EPQ (of CIBA SPECIALTY CHEMICALS Co., Ltd.) and may be used. The above phosphonite-based compounds may be used alone or in combination of two or more.

Examples of the thioether-based compound include dilauryl thiodipropionate, ditridecyl thiodipropionate, dimyristyl thiodipropionate, distearyl thiodipropionate, pentaerythritol-tetrakis(3-laurylthiopropionate), pentaerythritol-tetrakis(3-dodecylthiopropionate), pentaerythritol-tetrakis(3-octadecylthiopropionate), pentaerythritol-tetrakis(3-myristylthiopropionate) and pentaerythritol-tetrakis(3-stearylthiopropionate). The above thioether-based compounds may be used alone or in combination of two or more.

The content of the antioxidant (component C) is 0.001 to 2 parts by weight, preferably 0.005 to 1 part by weight, more preferably 0.01 to 0.5 part by weight based on 100 parts by weight of the resin component (component A). When the content of the antioxidant is lower than 0.001 part by weight, the antioxidizing effect becomes unsatisfactory with the result that color and flowability at the time of molding become unstable and hydrolysis resistance degrades. When the content is higher than 2 parts by weight, hydrolysis resistance is deteriorated by a reaction component derived from the antioxidant.

It is particularly preferred that a hindered phenol-based compound and at least one selected from a phosphite-based compound, a phosphonite-based compound and a thioether-based compound should be used in combination. When a combination of a hindered phenol-based compound and at least one selected from a phosphite-based compound, a phosphonite-based compound and a thioether-based compound is used, it exhibits a synergetic effect as a stabilizer and is effective in stabilizing color and flowability at the time of molding and improving hydrolysis resistance.

A combination of a hindered phenol-based compound and a phosphite-based compound is particularly preferred. The weight ratio of the hindered phenol-based compound to the phosphite-based compound is preferably 10:1 to 1:2, more preferably 5:1 to 1:1.

<Component D: End-Sealing Agent>

The resin composition of the present invention preferably comprises 0.001 to 10 parts by weight of at least one end-sealing agent (component D) selected from the group consisting of an epoxy compound, an oxazoline compound and an oxazine compound based on 100 parts by weight of the resin component (component A).

The end-sealing agent (component D) reacts with part or all of the terminal carboxyl group of the resin component (A) to seal the end of the resin component and is an addition reaction type compound such as an epoxy compound, an oxazoline compound or an oxazine compound. The cyclic carbodiimide as the component B is not included in the end-sealing agent (component D). When an addition reaction type compound is used, it is not necessary to discharge a surplus by-product to the outside of a reaction system unlike end-sealing by the dehydration condensation reaction of an alcohol and a carboxyl group. Therefore, by adding, mixing and reacting the addition reaction type end-sealing agent, a satisfactory terminal carboxyl group sealing effect can be obtained while the decomposition of the resin by a by-product is suppressed, thereby making it possible to obtain a resin composition having practically high hydrolysis resistance and a molded article of the resin composition.

Examples of the epoxy compound out of the above end-sealing agents (component D) include N-glycidyl phthalimide, N-glycidyl-4-methyl phthalimide, N-glycidyl-4,5-dimethyl phthalimide, N-glycildyl-3-methyl phthalimide, N-glycidyl-3,6-dimethyl phthalimide, N-glycidyl-4-ethoxy phthalimide, N-glycidyl-4-chlorophthalimide, N-glycidyl-4,5-dichlorophthalimide, N-glycidyl-3,4,5,6-tetrabromophthalimide, N-glycidyl-4-n-butyl-5-bromophthalimide, N-glycidylsuccinimide, N-glycidyl hexahydrophthalimide, N-glyclidyl-1,2,3,6-tetrahydrophthalimide, N-glycidyl maleinimide, N-glycidyl-α,β-dimethylsuccinimide, N-glycidyl-α-ethylsuccinimide, N-glycidyl-α-propylsuccinimide, N-glycidylbenzamide, N-glycidyl-p-methylbenzamide, N-glycidylnaphthoamide, N-glycidyl stearamide, N-methyl-4,5-epoxycyclohexane-1,2-dicarboximide, N-ethyl-4,5-epoxycyclohexane-1,2-dicarboximide, N-phenyl-4,5-epoxycyclohexane-1,2-dicarboximide, N-naphthyl-4,5-epoxycyclohexane-1,2-dicarboximide, N-tolyl-3-methyl-4,5-epoxycyclohexane-1,2-dicarboximide, orthophenylphenylglycidyl ether, 2-methyloctylglycidyl ether, phenyl glycidyl ether, 3-(2-xenyloxy)-1,2-epoxypropane, allylglycidyl ether, butylglycidyl ether, laurylglycidyl ether, benzylglycidyl ether, cyclohexylglycidyl ether, α-cresylglycidyl ether, p-tert-butylphenylglycidyl ether, glycidyl ether methacrylate, ethylene oxide, propylene oxide, styrene oxide, octylene oxide, hydroquinone diglycidyl ether, resorcin diglycidyl ether, 1,6-hexanediol diglycidyl ether, hydrogenated bisphenol A-diglycidyl ether, terephthalic acid diglycidyl ester, tetrahydrophthalic acid diglycidyl ester, hexahydrophthalic acid diglycidyl ester, phthalic acid dimethyl diglycidyl ester, phenylene diglycidyl ether, ethylene diglycidyl ether, trimethylene diglycidyl ether, tetramethylene diglycidyl ether, hexamethylene diglycidyl ether, 3,4-epoxycyclohexylmethyl-3,4-epoxycyclohexyl carboxylate, bis(3,4-epoxycyclohexylmethyl)adipate and vinylcyclohexane diepoxide.

Further, a polymer containing an epoxy group may be used in the present invention, and an acrylic polymer may be preferably used from the viewpoint of compatibility with polylactic acid. Examples of this polymer include a homopolymer of (meth)acrylic ester monomers containing an epoxy group, a copolymer of a (meth) acrylic acid ester monomer containing an epoxy group and a (meth)acrylic acid ester monomer, a homopolymer of acrylic acid ester monomers having an epoxy group, a copolymer of an acrylic acid ester monomer having an epoxy group and an acrylic acid ester monomer, a copolymer of a (meth)acrylic acid ester monomer having an epoxy group and an acrylic acid ester monomer, and a copolymer of an acrylic acid ester monomer having an epoxy group and a (meth)acrylic acid ester monomer. Examples of the acrylic styrene-based copolymer having an epoxy group include a copolymer of a styrene monomer and a (meth)acrylic acid ester monomer having an epoxy group and a copolymer of a styrene monomer and an acrylic acid ester monomer having an epoxy group. The carboxyl end of a polylactic acid unit should be sealed by arbitrarily selecting one or more compounds from these epoxy compounds. From the viewpoint of reactivity, ethylene oxide, propylene oxide, phenylglycidyl ether, orthophenylphenylglycidyl ether, p-tert-butylphenylglycidyl ether, N-glycidyl phthalimide, hydroquinone diglycidyl ether, resorcin diglycidyl ether, 1,6-hexanediol diglycidyl ether and hydrogenated bisphenol A-diglycidyl ether are preferred.

Examples of the oxazoline compound out of the end-sealing agents (component D) include 2-methoxy-2-oxazoline, 2-ethoxy-2-oxazoline, 2-propoxy-2-oxazoline, 2-butoxy-2-oxazoline, 2-pentyloxy-2-oxazoline, 2-hexyloxy-2-oxazoline, 2-heptyloxy-2-oxazoline, 2-octyloxy-2-oxazoline, 2-nonyloxy-2-oxazoline, 2-decyloxy-2-oxazoline, 2-cyclopentyloxy-2-oxazoline, 2-cyclohexyloxy-2-oxazoline, 2-allyloxy-2-oxazoline, 2-methallyloxy-2-oxazoline, 2-crotyloxy-2-oxazoline, 2-phenoxy-2-oxazoline, 2-cresyl-2-oxazoline, 2-o-ethylphenoxy-2-oxazoline, 2-o-propylphenoxy-2-oxazoline, 2-o-phenylphenoxy-2-oxazoline, 2-m-ethylphenoxy-2-oxazoline, 2-m-propylphenoxy-2-oxazoline, 2-p-phenylphenoxy-2-oxazoline, 2-methyl-2-oxazoline, 2-ethyl-2-oxazoline, 2-propyl-2-oxazoline, 2-butyl-2-oxazoline, 2-pentyl-2-oxazoline, 2-hexyl-2-oxazoline, 2-heptyl-2-oxazoline, 2-octyl-2-oxazoline, 2-nonyl-2-oxazoline, 2-decyl-2-oxazoline, 2-cyclopentyl-2-oxazoline, 2-cyclohexyl-2-oxazoline, 2-allyl-2-oxazoline, 2-methallyl-2-oxazoline, 2-crotyl-2-oxazoline, 2-phenyl-2-oxazoline, 2-o-ethylphenyl-2-oxazoline, 2-o-propylphenyl-2-oxazoline, 2-o-phenylphenyl-2-oxazoline, 2-m-ethylphenyl-2-oxazoline, 2-m-propylphenyl-2-oxazoline and 2-p-phenylphenyl-2-oxazoline.

Further, 2,2'-bis(2-oxazoline), 2,2'-bis(4-methyl-2-oxazoline), 2,2'-bis(4,4'-dimethyl-2-oxazoline), 2,2'-bis(4-ethyl-2-oxazoline), 2,2'-bis(4,4'-diethyl-2-oxazoline), 2,2'-bis(4-propyl-2-oxazoline), 2,2'-bis(4-butyl-2-oxazoline), 2,2'-bis(4-hexyl-2-oxazoline), 2,2'-bis(4-phenyl-2-oxazoline), 2,2'-bis(4-cyclohexyl-2-oxazoline), 2,2'-bis(4-benzyl-2-oxazoline), 2,2'-p-phenylenebis(2-oxazoline), 2,2'-m-phenylenebis(2-oxazoline), 2,2'-o-phenylenebis(2-oxazoline), 2,2'-p-phenylenebis(4-methyl-2-oxazoline), 2,2'-p-phenylenebis(4,4'-dimethyl-2-oxazoline), 2,2'-m-phenylenebis(4-methyl-2-oxazoline), 2,2'-m-phenylenebis(4,4'-dimethyl-2-oxazoline), 2,2'-ethylenebis(2-oxazoline), 2,2'-tetramethylenebis(2-oxazoline), 2,2'-hexamethylenebis(2-oxazoline), 2,2'-octamethylenebis(2-oxazoline), 2,2'-decamethylenebis(2-oxazoline), 2,2'-ethylenebis(4-methyl-2-oxazoline), 2,2'-tetramethylenebis(4,4'-dimethyl-2-oxazoline), 2,2'-9,9'-diphenoxyethanebis(2-oxazoline), 2,2'-cyclohexylenebis(2-oxazoline) and 2,2'-diphenylenebis(2-oxazoline) are also included.

Polyoxazoline compounds containing any one of the above compounds as a monomer unit such as a styrene 2-isopropenyl-2-oxazoline copolymer are also included. The carboxyl end of the polylactic acid unit should be sealed by arbitrarily selecting one or more compounds from these oxazoline compounds.

Examples of the oxazine compound out of the end-sealing agents (component D) include 2-methoxy-5,6-dihydro-4H-1,3-oxazine, 2-ethoxy-5,6-dihydro-4H-1,3-oxazine, 2-propoxy-5,6-dihydro-4H-1,3-oxazine, 2-butoxy-5,6-dihydro-4H-1,3-oxazine, 2-pentyloxy-5,6-dihydro-4H-1,3-oxazine, 2-hexyloxy-5,6-dihydro-4H-1,3-oxazine, 2-heptyloxy-5,6-dihydro-4H-1,3-oxazine, 2-octyloxy-5,6-dihydro-4H-1,3-oxazine, 2-nonyloxy-5,6-dihydro-4H-1,3-oxazine, 2-decyloxy-5,6-dihydro-4H-1,3-oxazine, 2-cyclopentyloxy-5,6-dihydro-4H-1,3-oxazine, 2-cyclohexyloxy-5,6-dihydro-4H-1,3-oxazine, 2-allyloxy-5,6-dihydro-4H-1,3-oxazine, 2-methallyloxy-5,6-dihydro-4H-1,3-oxazine and 2-crotyloxy-5,6-dihydro-4H-1,3-oxazine. Further, 2,2'-bis(5,6-dihydro-4H-1,3-oxazine), 2,2'-methylenebis(5,6-dihydro-4H-1,3-oxazine), 2,2'-ethylenebis(5,6-dihydro-4H-1,3-oxazine), 2,2'-propylenebis(5,6-dihydro-4H-1,3-oxazine), 2,2'-butylenebis(5,6-dihydro-4H-1,3-oxazine), 2,2'-hexamethylenebis(5,6-dihydro-4H-1,3-oxazine), 2,2'-p-phenylenebis(5,6-dihydro-4H-1,3-oxazine), 2,2'-m-phenylenebis(5,6-dihydro-4H-1,3-oxazine), 2,2'-naphthylenebis(5,6-dihydro-4H-1,3-oxazine) and 2,2'-P,P'-diphenylenebis(5,6-dihydro-4H-1,3-oxazine) are also included. Polyoxazine compounds containing any one of the above compounds as a monomer unit are also included. The carboxyl end of the polylactic acid unit should be sealed by arbitrarily selecting one or more compounds from these oxazine compounds.

Although the carboxyl end of the polylactic acid may be sealed by arbitrarily selecting one or more compounds from the above oxazoline compounds and the above oxazine compounds, 2,2'-m-phenylenebis (2-oxazoline) and 2,2'-p-phenylenebis (2-oxazoline) are preferred from the viewpoints of heat resistance, reactivity and affinity for the polylactic acid.

Two or more compounds out of the epoxy compounds, the oxazoline compounds and the oxazine compounds enumerated as the end-sealing agents (component D) may be used in combination as the end-sealing agent.

As for the degree of sealing the terminal carboxyl group, the concentration of the terminal carboxyl group of the polylactic acid is preferably 10 equivalents/$10^3$ kg or less from the viewpoint of improving hydrolysis resistance, more preferably 6 equivalents/$10^3$ or less.

To seal the terminal carboxyl group of the polylactic acid (component A-α), the end-sealing agent should be reacted, and to seal the terminal carboxyl group through an addition reaction, a suitable amount of the end-sealing agent such as an epoxy compound, oxazoline compound or oxazine compound should be reacted while the polylactic acid is molten. After the end of the polymerization reaction of a polymer, the end-sealing agent can be added and reacted.

The content of the end-sealing agent (component D) is preferably 0.001 to 10 parts by weight, more preferably 0.01 to 5 parts by weight, much more preferably 0.1 to 3 parts by weight based on 100 parts by weight of the resin component (component A). When the content of the end-sealing agent is lower than 0.001 part by weight, the amount of the end-sealing agent is too small as compared with the terminal carboxyl group and sufficiently high hydrolysis resistance is not obtained. When the content is higher than 10 parts by weight, gelation occurs and flowability greatly degrades.

<Component E: Hydrotalcite>

The resin composition of the present invention may comprise a hydrotalcite (component E). The hydrotalcite (component E) used in the present invention is preferably a synthetic hydrotalcite represented by the following general formula (9).

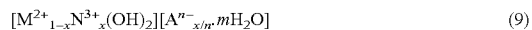

$$[M^{2+}{}_{1-x}N^{3+}{}_x(OH)_2][A^{n-}{}_{x/n}\cdot mH_2O] \qquad (9)$$

(In the above formula, $M^{2+}$ is a divalent metal ion such as magnesium ion or zinc ion, $N^{3+}$ is a trivalent metal ion such as aluminum ion or chromium ion, $A^{n-}$ is an n-valent interlayer anion, x satisfies $0<x\leq 0.33$, m satisfies $0\leq m<2$, and n is an integer which satisfies $1\leq n\leq 5$.)

$[M^{2+}{}_{1-x}N^{3+}{}_x(OH)_2]$ in the above formula (9) is a hydroxide sheet which is formed by the sharing of a hilly portion by octahedrons formed by surrounding the metal ion with 6 OH's. The hydroxide sheets are placed one upon another to form a layered structure. $[A^{n-}{}_{x/n}\cdot mH_2O]$ in the above formula (9) represents an n-valent anion and crystal water between hydroxide sheets.

$M^{2+}$ is not particularly limited as long as it is a divalent metal ion but preferably a magnesium ion. $N^{3+}$ is not particularly limited as long as it is a trivalent metal ion but preferably an aluminum ion. $A^{n-}$ is preferably a carbonate ion.

Although the mechanism that the hydrotalcite improves the hydrolysis resistance of the polylactic acid is unknown, it is considered that the hydrotalcite adsorbs an acid which serves a catalyst for the hydrolytic reaction of the polylactic acid, such as lactic acid produced by thermal decomposition and hydrolysis.

The hydrotalcite (component E) is preferably dehydrated by baking. The baking temperature may be selected according to the chemical structure of the hydrotalcite. For example, when $M^{2+}$ is a magnesium ion, $N^{3+}$ is an aluminum ion, $A^{n-}$ is a carbonate ion and the weight ratio of the magnesium ion to the aluminum ion is 2:1 (x=0.33), as the dehydration temperature of crystal water is 210° C., the hydrotalcite can be dehydrated by baking at a temperature higher than this temperature. As x becomes smaller than 0.33, the dehydration temperature of crystal water becomes lower. Since the decomposition of the resin in the extrusion or molding step can be prevented by using the dehydrated hydrotalcite, a resin composition having higher hydrolysis resistance can be obtained. Therefore, in the formula (9), "m" satisfies preferably $0\leq m<0.5$, most preferably $0\leq m\leq 0.1$.

The hydrotalcite (component E) is preferably surface treated. Examples of the surface treating agent include silane coupling agents, titanate coupling agents, silicone compounds, fatty acids, fatty acid salts and synthetic resins. Fatty acids and fatty acid salts having affinity for polylactic acid are particularly preferably used. By surface treating the hydrotalcite, the decomposition of the polylactic acid in the extrusion or molding step can be prevented and the dispersion of the hydrotalcite into the polylactic acid is enhanced, whereby an acid is adsorbed effectively, thereby making it possible to obtain a resin composition having higher hydrolysis resistance.

Although the fatty acid used for the surface treatment is not particularly limited as long as it is a fatty acid, a higher fatty acid having a relatively high boiling point and 12 or more carbon atoms is preferred. Examples of the higher fatty acid include lauric acid, myristic acid, palmitic acid, stearic acid, oleic acid, linoleic acid and linolenic acid. Although the fatty acid salt used for the surface treatment is not particularly limited as long as it is a fatty acid salt, a higher fatty acid salt having a relatively high boiling point and 12 or more carbon atoms is preferred. Examples of the higher fatty acid salt include lauric acid salts, myristic acid salts, palmitic acid salts, stearic acid salts, oleic acid salts, linoleic acid salts and linolenic acid salts. The salt used in the higher fatty acid salts is preferably an inorganic compound such as sodium, potassium or zinc.

In the present invention, a hydrotalcite which is neither dehydrated nor surface treated, a hydrotalcite which is either dehydrated or surface treated, and a hydrotalcite which is both dehydrated and surface treated may be used. A hydrotalcite which is either dehydrated or surface treated is preferred, and a hydrotalcite which is both dehydrated and surface treated is more preferred.

Commercially available products of the hydrotalcite which is neither dehydrated nor surface treated include DHT-6 (of Kyowa Chemical Industry Co., Ltd.), commercially available products of the hydrotalcite which is only dehydrated include DHT-4C (of Kyowa Chemical Industry Co., Ltd.), commercially available products of the hydrotalcite which is only surface treated include DHT-4A (of Kyowa Chemical Industry Co., Ltd.) and commercially available products of the hydrotalcite which is both dehydrated and surface treated include DHT-4A-2 (of Kyowa Chemical Industry Co., Ltd.).

The content of the hydrotalcite (component E) is preferably 0.01 to 0.3 part by weight, more preferably 0.03 to 0.2 part by weight, most preferably 0.05 to 0.2 part by weight based on 100 parts by weight of the resin component (component A). When the content of the hydrotalcite is lower than 0.01 part by weight, the effect of improving hydrolysis resistance is not obtained. When the content of the hydrotalcite (component E) is higher than 0.3 part by weight, the thermal decomposition of the polylactic acid occurs, thereby deteriorating hydrolysis resistance.

Preferably, the resin composition of the present invention comprises 0.01 to 0.3 part by weight of the hydrotalcite (component E) based on100 parts by weight of the resin component (component A).

<Component F: Impact Modifier>

The resin composition of the present invention may comprise an impact modifier (component F). When the resin composition comprises the impact modifier. (component F), impact resistance and hydrolysis resistance are improved. An impact modifier (component F-α) having at least one rubber layer therein which is made of at least one component selected from the group consisting of an acrylic component, a silicon-based component, a styrene-based component, a nitrile-based component, a conjugated diene-based component, an urethane-based component and an ethylene propylene-based component and containing a vinyl monomer as a component other than the rubber layer and/or an impact modifier (component F-β) containing substantially no rubber component are/is preferably used as the impact modifier (component F).

These two components may be used alone or in combination. It is needless to say that one or more compounds may be used as each of the above components. Preferably, these compounds are selected and used according to purpose.

(Component F-α)

The component F-α is an impact modifier having at least one rubber layer therein which is made of at least one component selected from the group consisting of an acrylic component, a silicon-based component, a styrene-based component, a nitrile-based component, a conjugated diene-based component, an urethane-based component and an ethylene propylene-based component and containing a vinyl monomer as a component other than the rubber layer. The component F-α is preferably at least one resin selected from the group consisting of a vinyl unit-containing resin containing a rubber component and having a rubber component content of less than 40 wt % (component F-α-1) and a vinyl unit-containing resin having a rubber component content of 40 wt % or more (component F-α-2).

(Component F-α-1)

The vinyl unit-containing resin which contains a rubber component and has a rubber component content of less than 40 wt % (component F-α-1) is a resin obtained by polymerizing at least one vinyl monomer and less than 40 wt % of a rubber component.

Examples of the above vinyl monomer include styrene-based compounds such as styrene and styrene derivatives including α-methylstyrene, o-methylstyrene, p-methylstyrene, vinyl xylene, ethyl styrene, dimethyl styrene, p-tert-butylstyrene, vinyl naphthalene, methoxy styrene, monobromostyrene, dibromostyrene, fluorostyrene and tribromostyrene. Vinyl cyanide compounds such as acrylonitrile and methacrylonitrile, aryl acrylates such as phenyl acrylate and benzyl acrylate, and alkyl acrylates such as methyl acrylate, ethyl acrylate, propyl acrylate, butyl acrylate, amyl acrylate, hexyl acrylate, 2-ethylhexyl acrylate, octyl acrylate, cyclohexyl acrylate and dodecyl acrylate, aryl methacrylates such as phenyl methacrylate and benzyl methacrylate, alkyl methacrylates such as methyl methacrylate, ethyl methacrylate, propyl methacrylate, butyl methacrylate, amyl methacrylate, hexyl methacrylate, 2-ethylhexyl methacrylate, octyl methacrylate, cyclohexyl methacrylate and dodecyl methacrylate, epoxy group-containing methacrylates such as glycidyl methacrylate, maleimide-based monomers such as maleimide, N-methylmaleimide and N-phenylmaleimide, and α,β-unsaturated carboxylic acids and anhydrides thereof such as acrylic acid, methacrylic acid, maleic acid, maleic anhydride, phthalic acid and itaconic acid are also included. They may be used alone or in combination of two or more.

Examples of the rubber component copolymerizable with the above vinyl monomer include diene-based copolymers such as polybutadiene, polyisoprene, styrene•butadiene random copolymer and block copolymer, acrylonitrile•butadiene copolymer, copolymers of an alkyl acrylate and/or an alkyl methacrylate and butadiene, and butadiene•isoprene copolymer; copolymers of ethylene and an α-olefin such as ethylene•propylene random copolymer and block copolymer, and ethylene•butene random copolymer and block copolymer; copolymers of ethylene and an unsaturated carboxylate such as ethylene•methacrylate copolymer and ethylene•butyl acrylate copolymer; copolymers of ethylene and an aliphatic vinyl such as ethylene•vinyl acetate copolymer; terpolymers of ethylene, propylene and a non-conjugated diene such as ethylene•propylene•hexadiene copolymer; acrylic rubbers such as butyl polyacrylate; and composite rubbers (to be referred to as "IPN type rubbers" hereinafter) having a structure that a polyorganosiloxane rubber component and a polyalkyl (meth)acrylate rubber component are intertwined with each other so that they cannot be separated from each other.

Examples of the vinyl unit component-containing resin which contains a rubber component and has a rubber component content of less than 40 wt % (component F-α-1) include styrene•butadiene•styrene copolymer (SBS resin), hydrogenated styrene•butadiene•styrene copolymer (hydrogenated SBS resin), hydrogenated styrene•isoprene•styrene copolymer (hydrogenated SIS resin), high-impact polystyrene (HIPS resin), acrylonitrile•styrene copolymer (AS resin), acrylonitrile•butadiene•styrene copolymer (ABS resin), methyl methacrylate•butadiene•styrene copolymer (MBS resin), methyl methacrylate•acrylonitrile•butadiene•styrene copolymer (MABS resin), acrylonitrile•styrene•acrylic rubber copolymer (ASA resin), acrylonitrile•ethylene propylene-based rubber•styrene copolymer (AES resin), styrene•methyl methacrylate copolymer (MS resin), methyl methacrylate•acrylonitrile•styrene copolymer (MAS resin), styrene•maleic anhydride copolymer (SMA resin), styrene•IPN type rubber copolymer and mixtures thereof. The styrene-based thermoplastic resin may have high stereoregularity like syndiotactic polystyrene due to the use of a catalyst such as a metallocene catalyst at the time of production. Further, according to the circumstances, a polymer and a copolymer having a narrow molecular weight distribution, a block copolymer, and a polymer and a copolymer having high stereoregularity, all of which are obtained by anion living polymerization or radical living polymerization, may also be used. They may be used alone or in combination of two or more.

One or a mixture of two or more selected from the group consisting of high-impact polystyrene (HIPS resin), an acrylonitrile•styrene copolymer (AS resin), an acrylonitrile•butadiene•styrene copolymer (ABS resin), an acrylonitrile•styrene•acrylic rubber copolymer (ASA resin), an acrylonitrile•ethylene propylene-based rubber•styrene copolymer (AES resin) and a methyl methacrylate•butadiene•styrene copolymer (MBS resin) out of these is preferably used, and ABS resin, ASA resin and AES resin are most preferred.

ABS resin used in the present invention is a mixture of a thermoplastic graft copolymer (ABS copolymer) obtained by graft polymerizing a vinyl cyanide compound and an aromatic vinyl compound with a diene-based rubber component and a copolymer (AS copolymer) of a vinyl cyanide compound and an aromatic vinyl compound. The copolymer of a vinyl cyanide compound and an aromatic vinyl compound may be a copolymer by-produced during the production of a resin composed of a thermoplastic graft copolymer obtained by graft copolymerizing a vinyl cyanide compound and an aromatic vinyl compound with a diene-based rubber component, or a copolymer obtained by copolymerizing an aromatic vinyl compound and a vinyl cyanide compound independently. As for the molecular weight of the copolymer of a vinyl cyanide compound and an aromatic vinyl compound, the reduced viscosity of the copolymer is preferably 0.2 to 1.0, more preferably 0.25 to 0.5. The proportion of the AS copolymer can be obtained by dissolving ABS resin in a good solvent for the AS copolymer such as acetone and centrifuging soluble matter. Insoluble matter (gel) is the net ABS copolymer.

The weight ratio (graft ratio) of the grafted vinyl cyanide compound and aromatic vinyl compound to the diene-based rubber component is preferably 20 to 200 wt %, more preferably 20 to 70 wt %.

As the diene-based rubber component forming the ABS resin is used a rubber having a glass transition point of 10° C. or lower, such as polybutadiene, polyisoprene or styrene-butadiene copolymer. The content of the diene-based rubber component is preferably 5 to 39.9 wt %, more preferably 10 to 35 wt %, much more preferably 10 to 25 wt % based on 100 wt % of the ABS resin component.

Examples of the vinyl cyanide compound to be grafted on the diene-based rubber component are those enumerated above, out of which acrylonitrile is preferred. Examples of the aromatic vinyl compound to be grafted on the diene-based rubber component are also those enumerated above, out of which styrene and α-methylstyrene are preferred. The amount of the component to be grafted on the diene-based rubber component is preferably 60.1 to 95 wt %, more preferably 65 to 90 wt %, much more preferably 75 to 90 wt % based on 100 wt % of the ABS resin component. The amount of the vinyl cyanide compound is preferably 5 to 50 wt %, more preferably 10 to 30 wt % and the amount of the aromatic vinyl compound is preferably 95 to 50 wt %, more preferably 90 to 70 wt % based on 100 wt % of the total of the vinyl cyanide compound and the aromatic vinyl compound. Further, methyl (meth)acrylate, ethyl acrylate, maleic anhydride or N-substituted maleimide may be used as part of the component to be grafted on the above diene-based rubber component, and the content thereof is preferably 15 wt % or less of the ABS resin component. Further, a conventionally known initiator, a chain transfer agent and an emulsifier which are used in a reaction may be used as required.

In the ABS resin, the diameter of rubber particles is preferably 0.1 to 5.0 μm, more preferably 0.3 to 3.0 μm, much more preferably 0.4 to 1.5 μm, particularly preferably 0.4 to 0.9 μm. Rubber particles having a particle size distribution with one mountain or two or more mountains may be used. The rubber particles may have a single phase in morphology or a salami structure that an occlusion phase is existent around the rubber particles.

The ABS resin may be produced by bulk polymerization, suspension polymerization or emulsion polymerization and copolymerized in a single stage or multiple stages. Examples of polymerization include general emulsion polymerization, soap-free polymerization using an initiator such as potassium persulfate, seed polymerization and two-stage swelling polymerization. In the suspension polymerization method, a water phase and a monomer phase are separately kept and supplied into a continuous disperser accurately to control the particle size by the revolution of the disperser. In the continuous production method, the particle size is controlled by supplying a monomer phase into an aqueous liquid having dispersion ability through a fine orifice or porous filter having an opening size of several to several tens of μm.

The ASA resin used in the present invention is a thermoplastic graft copolymer obtained by graft polymerizing a vinyl cyanide compound and an aromatic vinyl compound with an acrylic rubber component, or a mixture of the thermoplastic graft copolymer and a copolymer of a vinyl cyanide compound and an aromatic vinyl compound. The acrylic rubber used herein is an acrylic rubber which contains an alkyl acrylate unit having 2 to 10 carbon atoms. It may optionally contain another copolymerizable component such as styrene, methyl methacrylate or butadiene. Preferably, the alkyl acrylate having 2 to 10 carbon atoms is 2-ethylhexyl acrylate or n-butyl acrylate. The alkyl acrylate is preferably contained in an amount of 50 wt % or more based on 100 wt % of the acrylate rubber. The acrylate rubber is at least partially crosslinked, and examples of the crosslinking agent include ethylene glycol diacrylate, butylene glycol diacrylate, ethylene glycol dimethacrylate, allyl methacrylate and polypropylene glycol diacrylate. The crosslinking agent is preferably used in an amount of 0.01 to 3 wt % based on the acrylate rubber. The amount of the acrylic rubber component is preferably 5 to 39.9 wt %, more preferably 10 to 35 wt %, much more preferably 10 to 25 wt % based on 100 wt % of the ASA resin.

As for the ratio of the vinyl cyanide compound and the aromatic vinyl compound, preferably, the amount of the vinyl cyanide compound is 5 to 50 wt % and the amount of the aromatic vinyl compound is 95 to 50 wt % based on 100 wt % of the total of these. Particularly preferably, the amount of the vinyl cyanide compound is 15 to 35 wt % and the amount of the aromatic vinyl compound is 85 to 65 wt % based on 100 wt % of the total. The production process of the ASA resin may be the same as that of the above ABS resin.

The AES resin used in the present invention is a thermoplastic graft copolymer obtained by graft polymerizing a vinyl cyanide compound and an aromatic vinyl compound with an ethylene-propylene rubber component or an ethylene-propylene-diene rubber component, or a mixture of the thermoplastic graft copolymer and a copolymer of a vinyl cyanide compound and an aromatic vinyl compound. The production process of the AES resin may be the same as that of the above ABS resin.

(Component F-α-2)

The vinyl unit-containing resin having a rubber component content of 40 wt % or more (component F-α-2) is a resin obtained by polymerizing at least one vinyl monomer and 40 wt % or more of a rubber component.

A block copolymer of the rubber component and the above monomer may also be used. Examples of the block copolymer include thermoplastic elastomers such as styrene ethylene propylene•styrene elastomer (hydrogenated styrene•isoprene•styrene elastomer) and hydrogenated styrene•butadiene•styrene elastomer.

Elastic polymers known as thermoplastic elastomers such as polyurethane elastomers, polyester elastomers and polyether amide elastomers may also be used.

Examples of the rubber component include butadiene rubber, butadiene-acrylic composite rubber, acrylic rubber, acrylic-silicon composite rubber, isobutylene-silicon composite rubber, isoprene rubber, styrene-butadiene rubber, chloroprene rubber, ethylene-propylene rubber, nitrile rubber, ethylene-acrylic rubber, silicon rubber, epichlorohydrin rubber, fluorine rubber and rubbers obtained by adding hydrogen to the unsaturated bonds of these.

Impact modifiers containing a rubber component and having a glass transition temperature of preferably 10° C. or lower, more preferably −10° C. or lower, much more preferably −30° C. or lower are preferred. Impact modifiers comprising butadiene rubber, butadiene-acrylic composite rubber, acrylic rubber or acrylic-silicon composite rubber are particularly preferred. The composite rubber is a rubber obtained by copolymerizing two different rubber components or a polymerized rubber having an IPN structure that two different rubber components are intertwined with each other so that they cannot be separated from each other.

Examples of the aromatic vinyl include styrene, α-methylstyrene, p-methylstyrene, alkoxystyrene and halogenated styrene, out of which styrene is particularly preferred. Examples of the acrylic acid ester include methyl acrylate, ethyl acrylate, butyl acrylate, cyclohexyl acrylate and octyl acrylate. Examples of the methacrylic acid ester include methyl methacrylate, ethyl methacrylate, butyl methacrylate, cyclohexyl methacrylate and octyl methacrylate, out of which methyl methacrylate is particularly preferred.

The vinyl unit-containing resin having a rubber component content of 40 wt % or more may be produced by bulk polymerization, solution polymerization, suspension polymerization or emulsion polymerization, and copolymerization may be single-stage graft copolymerization or multi-stage graft copolymerization. The resin may be a mixture of copolymers each composed of a graft component by-produced during production. Examples of the polymerization include general emulsion polymerization, soap-free polymerization using an initiator such as potassium persulfate, seed polymerization and two-stage swelling polymerization. In the suspension polymerization method, a water phase and a monomer phase are separately kept and supplied into a continuous disperser accurately to control the particle size by the revolution of the disperser. In the continuous production method, the particle size is controlled by supplying a monomer phase into an aqueous liquid having dispersion ability through a fine orifice or porous filter having an opening size of several to several tens of μm.

The resin is commercially available and can be easily acquired. Examples of the resin comprising butadiene rubber, acrylic rubber or butadiene-acrylic composite rubber as the main rubber component include the Kaneace B series of Kaneka Corporation, the Metabrene C series of Mitsubishi Rayon Co., Ltd., the EXL series, HIA series, BTA series and KCA series of Kureha Chemical Industry Co., Ltd. and the UCL Modifier Resin Series of Ube Cyclon Co., Ltd. Examples of the resin comprising an acrylic-silicon composite rubber as the main rubber component include the Metabrene S-2001 and SRK-200 of Mitsubishi Rayon Co., Ltd.

A combination of the vinyl unit component-containing resin containing a rubber component and having a rubber component content of less than 40 wt % and the vinyl unit component-containing resin having a rubber component content of 40 wt % or more further enhances impact resistance. As a preferred example thereof, the vinyl unit component-containing resin having a rubber component content of 40 wt % or more is contained in an amount of 0.5 to 50 parts by weight based on 100 parts by weight of the vinyl unit component-containing resin containing a rubber component and having a rubber component content of less than 40 wt %.

(Component F-β)

At least one resin selected from the group consisting of a copolyester and a copolyethylene is preferred as the impact modifier (component F-β) containing substantially no rubber component of the present invention.

Examples of the copolyester include a copolyester containing a polylactic acid component and a copolyester having a star-like structure containing a polybutylene adipate terephthalate component. Specific examples of the copolyester include the "Plamate PD-150" and "PD-350" marketed by Dainippon Ink and Chemicals, Ltd. under the trade name of Plamate and the "Ecoflex SBX7025" marketed by BASF Japan Co., Ltd. under the trade name of Ecoflex.

Specific examples of the copolyethylene include "Bond Fast E" comprising ethylene and glycidyl methacrylate and "Bond Fast 7M" containing a methyl acrylate unit, marketed by Sumitomo Chemical Co., Ltd. under the trade name of Bond Fast and Biomax Strong 100 manufactured by DuPont Co., Ltd.

The polyester elastomer is an elastomer which has a polybutylene terephthalate skeleton as the main skeleton and contains a polyalkylene glycol, as exemplified by the TR-EL-1 of Teijin Limited.

The polyamide elastomer is an elastomer which comprises a hard segment composed of a polyamide oligomer and a soft segment composed of a polyester or polyether ester, as exemplified by the TPAE31, TPAE32 and TPAE38 of Fuji Kasei Kogyo Co., Ltd.

The content of the impact modifier (component F) is preferably 2 to 100 parts by weight, more preferably 3 to 90 parts by weight, much more preferably 5 to 80 parts by weight based on 100 parts by weight of the resin component (component A). When the content of the impact modifier is lower than 2 parts by weight, the amount of the impact modifier is too small, whereby sufficiently high impact resistance and hydrolysis resistance are not obtained. When the content is higher than 100 parts by weight, heat resistance deteriorates, which is not preferred from the viewpoint of environmental burden as most impact modifiers are derived from oil.

Preferably, the resin composition of the present invention comprises 2 to 100 parts by weight of the impact modifier (component F) based on 100 parts by weight of the resin component (component A).

<Component G: Flame Retardant>

The resin composition of the present invention may comprise at least one flame retardant (component G) selected from the group consisting of a phosphorus-based flame retardant (component G-1), a nitrogen-based flame retardant (component G-2), a metal hydroxide-based flame retardant (component G-3), a metal oxide-based flame retardant (component G-4) and a bromine-based flame retardant (component G-5). These flame retardants (component G) may be used alone or in combination of two or more, and a plurality of compounds of the same type may be used in combination. Preferably, they are selected and used according to purpose.

(Phosphorus-Based Flame Retardant: Component G-1)

Examples of the phosphorus-based flame retardant (component G-1) include (1) a phosphate-based flame retardant (2) a phosphonitrile-based flame retardant, (3) a phosphonate-based flame retardant, (4) a metal phosphinate-based flame retardant and (5) a metal phosphate-based flame retardant.

(1) Phosphate-Based Flame Retardant

The phosphate-based flame retardant which can be used in the present invention is selected from a phosphate compound and a phosphaphenanthrene compound. A specific example of the phosphate-based flame retardant is at least one phosphate compound represented by the following formula (10).

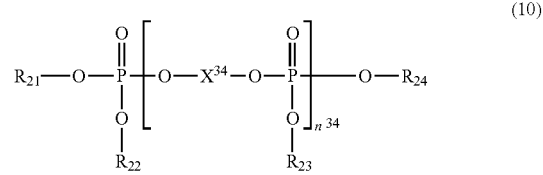

(10)

In the above formula, $X^{34}$ is a group derived from hydroquinone, resorcinol, bis(4-hydroxydiphenyl)methane, bisphenol A, dihydroxydiphenyl, dihydroxynaphthalene, bis(4-hydroxyphenyl)sulfone, bis(4-hydroxyphenyl)ketone or bis (4-hydroxyphenyl)sulfide. $n^{34}$ is an integer of 0 to 5 or an average value of 0 to 5 in the case of a mixture of phosphates which differ in n. $R_{21}$, $R_{22}$, $R_{23}$ and $R_{24}$ are each independently a group derived from phenol, cresol, xylenol, isopropylphenol, butylphenol and p-cumylphenol at least one halogen atom of which is substituted or not substituted.

More preferably, $X^{34}$ in the formula is a group derived from hydroquinone, resorcinol, bisphenol A and dihydroxydiphenyl, $n^{34}$ is an integer of 1 to 3 or an average value in the case of a blend of phosphates which differ in n, and $R_{21}$, $R_{22}$, $R_{23}$ and $R_{24}$ are each independently a group derived from phenol, cresol and xylenol at least one halogen atom of which is substituted or preferably not substituted.

Out of these phosphate-based flame retardants, triphenyl phosphate as a phosphate compound and resorcinol bis (dixylenylphosphate) and bisphenol A bis(diphenylphosphate) as phosphase oligomers are preferably used as they are excellent in hydrolysis resistance. Resorcinol bis(dixylenylphosphate) and bisphenol A bis(diphenylphosphate) are more preferred from the viewpoint of heat resistance. Since they have high heat resistance, they do not thermally deteriorate or volatilize.

(2) Phosphonitrile-Based Flame Retardant

The phosphonitrile-based flame retardant used in the present invention is a phosphonitrile linear polymer or a phosphonitrile cyclic polymer which is an oligomer or polymer having a recurring unit represented by the following formula (11) and preferably has a number average degree of polymerization of 3 or more. It may be linear or cyclic, particularly preferably a cyclic trimer. It may be a mixture of a linear product and a cyclic product in an arbitrary ratio.

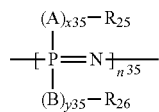

(11)

In the above formula, A and B are each independently an O, N or S atom. $R_{25}$ and $R_{26}$ are each independently an aryl group having 6 to 15 carbon atoms, alkyl group having 6 to 15 carbon atoms, aralkyl group having 6 to 15 carbon atoms or cycloalkyl group having 6 to 15 carbon atoms. $R_{25}$ and $R_{26}$ may be bonded together to form a cyclic structure. $X^{35}$ and $y^{35}$ are each 0 or 1. $n^{35}$ which means the number average degree of polymerization is 3 or more.

The phosphonitrile linear polymer and the phosphonitrile cyclic polymer can be synthesized by reacting hexachlorocyclotriphosphazene, octachlorocyclotetraphosphazene or poly(dichlorophosphazene) obtained by ring-opening polymerizing any one of these cyclic oligomers with a nucleophilic reagent such as an alcohol, phenol, amine, thiol or Grignard reagent in accordance with a known method.

(3) Phosphonate-Based Flame Retardant

The phosphonate-based flame retardant is preferably represented by the following general formula (12).

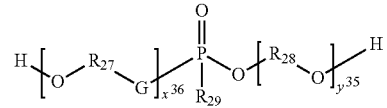

(12)

In the above formula, $R_{27}$ and $R^{28}$ are each independently a branched or unbranched alkylene group having 1 to 24 carbon atoms, substituted or unsubstituted arylene group having 6 to 20 carbon atoms, substituted or unsubstituted aralkylene group having 6 to 30 carbon atoms, or substituted or unsubstituted alkarylene group having 6 to 30 carbon atoms.

$R_{29}$ is a hydrogen atom, branched or unbranched alkyl group having 1 to 24 carbon atoms, substituted or unsubstituted aryl group having 6 to 20 carbon atoms, substituted or unsubstituted aralkyl group having 6 to 30 carbon atoms, or substituted or unsubstituted alkaryl group having 6 to 30 carbon atoms. $X^{36}$ and $y^{37}$ are each independently a numeral of 1 to 50.

(4) Metal Phosphinate-Based Flame Retardant

Organic metal phosphinates represented by the following formulas (13) and (14) are used alone or in combination of two or more.

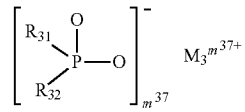

(13)

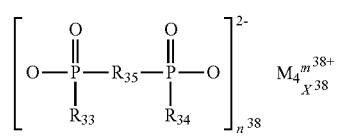

(14)

In the above formulas, $R_{31}$, $R_{32}$, $R_{33}$ and $R_{34}$ are each independently a linear or branched alkyl group having 1 to 20 carbon atoms, cycloalkyl group having 6 to 20 carbon atoms, aryl group having 6 to 20 carbon atoms or aralkyl group having 7 to 20 carbon atoms. $R_{35}$ is a linear or branched alkylene group having 1 to 20 carbon atoms, cycloalkylene group having 6 to 20 carbon atoms, arylene group having 6 to 20 carbon atoms, alkylene arylene group having 7 to 20 carbon atoms or cycloalkylene arylene group having 7 to 20 carbon atoms. $M_3$ and $M_4$ are each Mg, Ca, Al, Zn, Fe, Zr, Ce, Bi, Sr, Mn, Li, Na, K or protonated nitrogen base. $X^{38}$ is 1 or 2. $m^{37}$ and $m^{38}$ are each 2 or 3, and $n^{38}$ is 1 or 3.

$R_{31}$, $R_{32}$, $R_{33}$ and $R_{34}$ are each preferably selected from a linear or branched alkyl group having 1 to 20 carbon atoms, a cycloalkyl group having 6 to 20 carbon atoms, an aryl group having 6 to 20 carbon atoms and an aralkyl group having 7 to 20 carbon atoms so as to keep a suitable content of phosphorus in the flame retardant and develop flame retardancy and the crystallinity of the resin composition advantageously. Out of these, a linear or branched alkyl group having 1 to 20 carbon atoms and an aryl group having 6 to 20 carbon atoms are particularly preferably selected.

Preferred examples of the alkyl group and the aryl group include methyl group, ethyl group, n-propyl group, isopropyl group, n-butyl group, tert-butyl group, n-pentyl group and phenyl group. $R_{35}$ is preferably selected from a linear or branched alkylene group having 1 to 10 carbon atoms, a cycloalkylene group having 6 to 20 carbon atoms, an arylene group having 6 to 20 carbon atoms, an alkylene arylene group having 7 to 20 carbon atoms and a cycloalkylene arylene group having 7 to 20 carbon atoms so as to keep a suitable content of phosphorus in the flame retardant and develop flame retardancy and the crystallinity of the resin composition advantageously.

Specific examples of these groups include methylene group, ethylene group, methylethane-1,3-diyl group, propane-1,3-diyl group, 2,2-dimethylpropane-1,3-diyl group, butane-1,4-diyl group, octane-1,8-diyl group, phenylene group, naphthylene group, ethylphenylene group, tert-butylphenylene group, methylnaphthylene group, ethylnaphthylene group, phenylenemethylene group, phenyleneethylene group, phenylenepropylene group and phenylenebutylene group.

$M_3$ and $M_q$ are each at least one selected from Mg, Ca, Al, Zn, Fe, Zr, Ce, Bi, Sr, Mn, Li, Na, K and protonated nitrogen base. Examples of the protonated nitrogen base include amido group, ammonium group, alkylammonium group and melamine-derived group.

To improve the flame retardancy, crystallinity and moldability of the resin composition of the present invention, $M_3$ and $M_4$ are each one selected from the group consisting of Mg, Ca, Al, Zn, amido group, ammonium group, alkylammonium group and melamine-derived group. Out of these, Al is most preferred.

When phosphinates represented by the above formulas (13) and (14) are used in combination, the weight ratio of the phosphinate of the formula (13) to the phosphinate of the formula (14) is preferably selected from a range of 10/90 to 30/70.

The metal phosphinate-based flame retardant used in the present invention may be surface treated or coated with a thermosetting resin to improve its moisture resistance. Examples of the above thermosetting resin include phenolic resin, melamine-based resin, urea-based resin, alkyd resin, unsaturated polyester resin, epoxy resin and silicone-based resin which may be used alone or in combination of two or more.

The metal phosphinate-based flame retardant used in the present invention may be surface treated with a surface treating agent to improve its adhesion to a base resin. As the surface treating agent may be used functional compounds (such as epoxy-based compounds, silane-based compounds and titanate-based compounds).

(5) Metal Phosphate-Based Flame Retardant

The metal phosphate is preferably selected from aluminum phosphite represented by the following general formula (15), monobasic aluminum phosphate represented by the following general formula (16) and tribasic aluminum phosphate represented by the following formula (17), all of which contain aluminum.

(15)

(16)

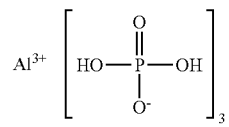
(17)

Out of the flame retardants represented by the general formulas (15) to (17), flame retardants represented by the general formulas (15) and (16) are preferred from the viewpoints of the heat stability and flame retardancy of the resin composition, aluminum phosphite represented by the general formula (15) is particularly preferred from the viewpoints of heat stability and flame retardancy, and expandable aluminum phosphite is most preferred from the viewpoint of flame retardancy.

The expandable aluminum phosphite is obtained by reacting a phosphoric acid or phosphorous acid component with an aluminum compound and optionally a basic component. A basic aluminum compound (such as aluminum hydroxide) may be used in place of the aluminum compound and the basic component. This expandable aluminum phosphite is available from Taihei Kagaku Sangyo Co., Ltd. under the trade name of APA series (such as APA-100).

The expandable aluminum phosphite can be generally expanded to preferably 10 to 70 times, more preferably 20 to 50 times, much more preferably 30 to 40 times at a temperature of 380 to 480° C.

The content of aluminum in aluminum phosphite which is a most preferred metal phosphate is preferably 5 to 25 wt o, more preferably 8 to 20 wt %. The content of phosphorus is preferably 15 to 35 wt o, more preferably 16 to 35 wt o, much more preferably 17 to 33 wt %. A water dispersion containing 5 wt % of aluminum phosphite has a pH of preferably 3.5 to 8.5, more preferably 4 to 8, much more preferably 4.5 to 7.5. Aluminum phosphite can be generally used in a particulate form. The average particle diameter of the particulate aluminum phosphite is preferably 0.01 to 100 μm, more preferably 0.1 to 50 μm. The oil adsorption of aluminum phosphite is preferably 15 to 50 mL/100 g, more preferably 20 to 40 mL/100 g, much more preferably 25 to 30 mL/100 g. The BET specific surface area of aluminum phosphite is preferably 0.3 to 2 m$^2$/g, more preferably 0.5 to 1.5 m$^2$/g, much more preferably 0.8 to 1.2 m$^2$/g. Since this metal salt has excellent safety, it has a low environmental burden and is economically advantageous and when it is added to the resin composition, a material having excellent heat stability, heat resistance and moldability is obtained.

The metal phosphate-based flame retardant used in the present invention may be surface treated or coated with a thermosetting resin to improve its moisture resistance. Examples of the above thermosetting resin include phenolic resin, melamine-based resin, urea-based resin, alkyd resin, unsaturated polyester resin, epoxy resin and silicone-based resin which may be used alone or in combination of two or more.

The metal phosphate-based flame retardant used in the present invention may be surface treated with a surface treating agent to improve its adhesion to a base resin. As the surface treating agent may be used functional compounds (such as epoxy-based compounds, silane-based compounds and titanate-based compounds).

(Nitrogen-Based Flame Retardant: Component G-2)

The nitrogen-based flame retardant (component G-2) is preferably at least one selected from the group consisting of a melamine-based compound, a reaction product of a melamine-based compound and a polyphosphoric acid, and a reaction product of a melamine condensate and a polyphosphoric acid, particularly preferably at least one selected from the group consisting of flame retardants represented by the following formulas (18) and (19).

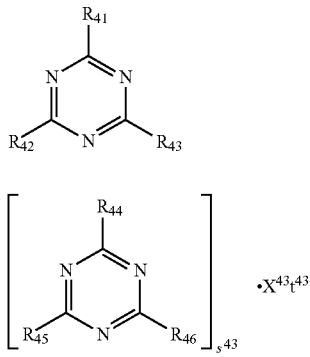

(18)

(19)

[In the above formulas, $R_{41}$ to $R_{46}$ are each independently a hydrogen atom, alkyl group having 1 to 8 carbon atoms, cycloalkyl group having 5 to 16 carbon atoms (they are not substituted or substituted by a hydroxyl group or hydroxyalkyl group having 1 to 4 carbon atoms), alkenyl group having 2 to 8 carbon atoms, alkoxy group having 1 to 8 carbon atoms, acyl group or acyloxy group aryl group having 6 to 12 carbon atoms, —O—RA or —N(RA)(RB). RA and RB are each a hydrogen atom, alkyl group having 1 to 8 carbon atoms, cycloalkyl group having 5 to 16 carbon atoms (they are not substituted or substituted by a hydroxyl group or hydroxyalkyl functional group having 1 to 4 carbon atoms), alkenyl group having 2 to 8 carbon atoms, alkoxy group having 1 to 8 carbon atoms, acyl group or acyloxy group, or aryl group having 6 to 12 carbon atoms. All of $R_{41}$ to $R_{46}$ cannot be hydrogen atoms at the same time, and all of $R_{41}$ to $R_{46}$ in the formulas (18) and (19) cannot be —$NH_2$ at the same time. $X^{43}$ is melamine or an acid capable of forming an adduct with a triazine compound, and $s^{43}$ and $t^{43}$ are each independently 1 or 2.]

Preferred examples of the flame retardants represented by the formulas (18) and (19) include dimelamine pyrophosphate, melamine polyphosphate, melem polyphosphate, melam polyphosphate and melon polyphosphate.

In the present invention, the flame retardancy of the resin composition of the present invention can be improved by using at least one of compounds represented by the following formulas (20) to (23) in combination with the nitrogen-based flame retardant having a triazine skeleton.

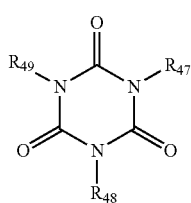

(20)

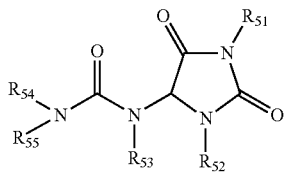

(21)

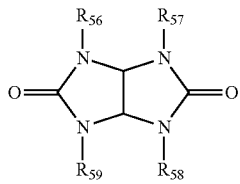

(22)

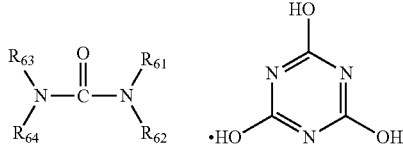

(23)

In the above formulas, $R_{47}$ to $R_{49}$, $R_{51}$ to $R_{59}$ and $R_{61}$ to $R_{64}$ are preferably each independently functional groups enumerated for $R_{41}$ to $R_{46}$. Preferred examples of these groups include tris(hydroxyethyl)isocyanurate, alanine, glycoluril, urea and cyanurate. The compound is used in an amount of 10 to 50 wt % based on the nitrogen-based flame retardant having a triazine skeleton.

(Metal Hydroxide-Based Flame Retardant: Component G-3)

Examples of the metal hydroxide-based flame retardant (component G-3) include magnesium hydroxide, aluminum hydroxide, calcium hydroxide, zinc hydroxide, potassium hydroxide, silicon hydroxide, titanium hydroxide, iron hydroxide, copper hydroxide, sodium hydroxide, nickel hydroxide, boron hydroxide, manganese hydroxide and lithium hydroxide. Out of these, magnesium hydroxide, aluminum hydroxide and calcium hydroxide are particularly preferred because they have a high flame retarding effect due to the high concentration of the hydroxyl group per molecular weight and low toxicity and are inexpensive.

To improve the heat stability of the resin composition, the metal hydroxide-based flame retardant (component G-3) preferably has high purity, especially a purity of 99.5% or more. The purity of the metal hydroxide-based flame retardant can be measured by a known method. For example, the purity of the metal hydroxide-based flame retardant can be obtained by measuring the content of impurities in the metal hydroxide-based flame retardant by a known method and subtracting the above content of impurities from the whole amount. For example, in the case of aluminum hydroxide, the impurities include $Fe_2O_3$, $SiO_2$, T-$Na_2O$ and S—$Na_2O$.

The content of $Fe_2O_3$ is obtained by O-phenanthroline absorptiometry (JISH 1901) after it is dissolved in a sodium carbonate-boric acid solution. The content of $SiO_2$ is obtained by molybdenum blue absorptiometry (JISH 1901) after it is dissolved in a sodium carbonate-boric acid solution. The content of T-$Na_2O$ is obtained by flame photometry after it is dissolved in sulfuric acid, and the content of S—$Na_2O$ is obtained by flame photometry after it is extracted with hot water. The purity of the hydroxide can be obtained by subtracting the above obtained contents from the weight of aluminum hydroxide. It is needless to say that different types of metal hydroxide-based flame retardants can be used in combination.

The shape of the metal hydroxide-based flame retardant (component G-3) is not particularly limited but preferably particulate. The average particle diameter obtained by a laser diffraction method of the flame retardant is preferably about 100 μm or less. In this case, any particle size distribution is acceptable. From the viewpoints of injection moldability in the molding process and dispersibility at the time of kneading, the average particle diameter is preferably within the above range and a smaller average particle diameter out of the above range is more preferred. To increase the filling rate into the resin composition, a plurality of metal hydroxide-based flame retardants which differ in average particle diameter may be used in combination.

Further, particles having a BET specific surface area obtained by a nitrogen gas adsorption method of about 5.0 $m^2/g$ or less are preferably used. As a matter of course, to increase the filling rate into the resin composition, a plurality of metal hydroxide-based flame retardants which differ in BET specific surface area may be used in combination. From the viewpoint of moldability, the BET specific surface area is preferably within the above range, and a smaller BET specific surface area out of the above range is more preferred.

The metal hydroxide-based flame retardant (component G-3) may be surface treated or coated with a thermosetting resin to improve its moisture resistance. Examples of the above thermosetting resin include phenolic resin, melamine-based resin, urea-based resin, alkyd resin, unsaturated polyester resin, epoxy resin and silicone-based resin which may be used alone or in combination of two or more.

The metal hydroxide-based flame retardant (component G-3) may be surface treated with a surface treating agent to improve its adhesion to a base resin. As the surface treating agent may be used functional compounds (such as epoxy-based compounds, silane-based compounds and titanate-based compounds).

(Component G-4: Metal Oxide-Based Flame Retardant)

Examples of the metal oxide-based flame retardant (component G-4) include magnesium oxide, aluminum oxide, calcium oxide, zinc oxide, potassium oxide, silicon oxide, titanium oxide, iron oxide, copper oxide, sodium oxide, nickel oxide, boron oxide, manganese oxide, lithium oxide and antimony oxide.

The shape of the metal oxide-based flame retardant (component G-4) is not particularly limited but preferably particulate. The average particle diameter obtained by a laser diffraction method of the flame retardant is preferably about 100 μm or less. In this case, any particle size distribution is acceptable. From the viewpoint of injection moldability in the molding process and dispersibility at the time of kneading, the average particle diameter is preferably within the above range and a smaller average particle diameter out of the above range is more preferred. To increase the filling rate into the resin composition, a plurality of metal oxide-based flame retardants which differ in average particle diameter may be used in combination.

Further, particles having a BET specific surface area obtained by a nitrogen gas adsorption method of about 5.0 $m^2/g$ or less are preferably used. As a matter of course, to increase the filling rate into the resin composition, a plurality of metal oxide-based flame retardants which differ in BET specific surface area may be used in combination. From the viewpoint of moldability, the BET specific surface area is preferably within the above range, and a smaller BET specific surface area out of the above range is more preferred.

The metal oxide-based flame retardant (component G-4) may be surface treated or coated with a thermosetting resin to improve its moisture resistance. Examples of the above thermosetting resin include phenolic resin, melamine-based resin, urea-based resin, alkyd resin, unsaturated polyester resin, epoxy resin and silicone-based resin which may be used alone or in combination of two or more.

The metal oxide-based flame retardant (component G-4) used in the present invention may be surface treated with a surface treating agent to improve its adhesion to a base resin. As the surface treating agent may be used functional compounds (such as epoxy-based compounds, silane-based compounds and titanate-based compounds).

Although each metal oxide-based flame retardant (component G-4) may be used alone, when it is used in combination with a phosphorus-based flame retardant, nitrogen-based flame retardant or bromine-based flame retardant, an especially high flame retarding effect is obtained advantageously.

(Bromine-Based Flame Retardant: Component G-5)

The bromine-based flame retardant (component G-5) is selected from a brominated bisphenol A type polycarbonate flame retardant having a bromine content of 20 wt % or more, a modified product of a brominated bisphenol A type epoxy resin and/or a modified product obtained by sealing part or all of the terminal glycidyl group of the brominated bisphenol A type epoxy resin, a brominated diphenyl ether flame retardant, a brominated imide flame retardant and a brominated polystyrene flame retardant.

Specific examples of the bromine-based flame retardant include decabromodiphenyl oxide, octabromodiphenyl oxide, tetrabromodiphenyl oxide, tetrabromophthalic anhydride, hexabromocyclododecane, bis(2,4,6-tribromophenoxy)ethane, ethylenebistetrabromophthalimide, hexabromobenzene, 1,1-sulfonyl[3,5-dibromo-4-(2,3-dibromopropoxy)]benzene, polydibromophenylene oxide, tetrabromobisphenol S, tris(2,3-dibromopropyl-1)isocyanurate, tribromophenol, tribromophenylallyl ether, tribromoneopentyl alcohol, brominated polystyrene, brominated polyethylene, tetrabromobisphenol A, tetrabromobisphenol A derivatives, tetrabromobisphenol A-epoxy oligomer or polymer, tetrabromobisphenol A-carbonate oligomer or polymer, brominated epoxy resins such as brominated phenol novolak epoxy, tetrabromobisphenol A-bis(2-hydroxydiethyl ether), tetrabromobisphenol A-bis(2,3-dibromopropyl ether), tetrabromobisphenol A-bis(allyl ether), tetrabromocyclooctane, ethylenebispentabromodiphenyl, tris(tribromoneopentyl)phosphate, poly(pentabromobenzyl polyacrylate), octabromotrimethylphenyl indane, dibromoneopentyl glycol, pentabromobenzyl polyacrylate, dibromocresyl glycidyl ether and N,N'-ethylene-bis-tetrabromophthalimide. Out of these, tetrabromobisphenol A-epoxy oligomer, tetrabromobisphenol A-carbonate oligomer and brominated epoxy resins are preferred.

The content of at least one flame retardant (component G) selected from a phosphorus-based flame retardant (component G-1), a nitrogen-based flame retardant (component G-2), a metal hydroxide-based flame retardant (component G-3), a metal oxide-based flame retardant (component G-4) and a bromine-based flame retardant (component G-5) is preferably 1 to 100 parts by weight, more preferably 3 to 90 parts by weight, much more preferably 5 to 80 parts by weight based on 100 parts by weight of the resin component (component A). When the content of the flame retardant (component G) is lower than 1 part by weight, the amount of the flame retardant is too small, whereby flame retardancy is not obtained and when the content is higher than 100 parts by weight, heat resistance deteriorates and releasability degrades disadvantageously.

Preferably, the resin composition comprises 1 to 100 parts by weight of at least one flame retardant (component G) selected from the group consisting of a phosphorus-based flame retardant (component G-1), a nitrogen-based flame retardant (component G-2), a metal hydroxide-based flame retardant (component G-3), a metal oxide-based flame retardant (component G-4) and a bromine-based flame retardant (component G-5) based on 100 parts by weight of the resin component (component A).

(Component H: Inorganic Filler)

The resin composition of the present invention may comprise an inorganic filler (component H). When the resin composition comprises an inorganic filler, it can have excellent mechanical properties, heat resistance and moldability. The inorganic filler used in the present invention is a fibrous, lamellar or powdery filler which is generally used to reinforce an ordinary thermoplastic resin.

Examples of the inorganic filler include fibrous inorganic fillers such as carbon nanotubes, glass fibers, asbestos fibers, carbon fibers, graphite fibers, metal fibers, potassium titanate whiskers, aluminum borate whiskers, magnesium-based whiskers, silicon-based whiskers, wollastonite, imogolite, sepiolite, asbestos, slug fibers, zonolite, gypsum fibers, silica fibers, silica-alumina fibers, zirconia fibers, boron nitride fibers, silicon nitride fibers and boron fibers, and lamellar and particulate inorganic fillers such as lamellar silicates, lamellar silicates exchanged with an organic onium ion, glass flakes, non-swelling mica, graphite, metal foils, ceramic beads, talc, clay, mica, sericite, zeolite, bentonite, dolomite, kaolin, powdery silicic acid, feldspar powder, potassium titanate, sirasu balloon, calcium carbonate, magnesium carbonate, barium sulfate, calcium oxide, aluminum oxide, titanium oxide, aluminum silicate, silicon oxide, gypsum, novaculite, dawsonite and carbon nanoparticles including white clay fullerene.

The lamellar silicates include smectite-based clay minerals such as montmorillonite, beidellite, nontronite, saponite, hectorite and sauconite, clay minerals such as vermiculite, halocite, kanemite and kenyaite, and swelling micas such as Li-fluoro taeniolite, Na-fluoro taeniolite, Li-tetrasilica fluoro mica and Na-tetrasilica fluoro mica. They may be natural or synthetic. Out of these, smectite-based clay minerals such as montmorillonite and hectorite, and swelling synthetic micas such as Li-fluoro taeniolite and Na-tetrasilica fluoro mica are preferred.

Out of these inorganic fillers (component H), fibrous or lamellar inorganic fillers are preferred, and glass fibers, wollastonite, aluminum borate whiskers, potassium titanate whiskers, mica, kaolin and cation exchanged lamellar silicates are particularly preferred. The aspect ratio of the fibrous filler is preferably 5 or more, more preferably 10 or more, much more preferably 20 or more.

The filler may be coated with or converged by a thermoplastic resin such as an ethylene-vinyl acetate copolymer or a thermosetting resin such as epoxy resin, or treated with a coupling agent such as aminosilane or epoxysilane.

The content of the inorganic filler (component H) is preferably 0.05 to 150 parts by weight, more preferably 0.5 to 100 parts by weight, much more preferably 1 to 70 parts by weight, particularly preferably 1 to 50 parts by weight, most preferably 1 to 30 parts by weight based on 100 parts by weight of the resin component (component A). When the content of the inorganic filler is lower than 0.05 part by weight, the reinforcing effect becomes unsatisfactory and when the content is higher than 150 parts by weigh, the appearance of a molded article may become worse and a strand may be broken at the time of extrusion.

<Component I: Flame Retarding Aid>

The resin composition of the present invention may comprise a flame retarding aid (component I). The flame retarding aid (component I) used in the present invention is preferably an aromatic resin and/or a fluorine-containing polymer having fibril forming ability.

Examples of the aromatic resin include polyphenylene ether resin, phenolic resin, aromatic epoxy resin, phenoxy resin, polyphenylene sulfide-based resin, polyarylate-based resin, aromatic polyamide-based resin and aromatic polyester amide-based resin. Polyphenylene ether resin, phenolic resin, aromatic epoxy resin and phenoxy resin are particularly preferred as they have high carbonization acceleration efficiency at the time of combustion. The polyphenylene ether resin of the present invention is a phenol polymer or copolymer having a phenylene ether structure.

Specific examples of the polyphenylene ether resin include poly(oxy-1,4-phenylene), poly(oxy-2,6-dimethylphenylene-1,4-diyl), poly(oxy-2,6-methyl-6-ethylphenylene-1,4-diyl), poly(oxy-2,6-diethylphenylene-1,4-diyl), poly(oxy-2-ethyl-6-n-propylphenylene-1,4-diyl), poly(oxy-2,6-di(n-propyl)phenylene-1,4-diyl), poly(oxy-2-methyl-6-n-butylphenylene-1,4-diyl), poly(oxy-2-ethyl-6-isopropylphenylene-1,4-diyl), poly(oxy-2-methyl-6-hydroxyethylphenylene-1,4-diyl) and poly(oxy-2-methyl-6-chloroethylphenylene-1,4-diyl). Out of these, poly(oxy-2,6-dimethylphenylene-1,4-diyl) is particularly preferred.

Examples of the copolymer having a phenylene ether structure include a copolymer of 2,6-dimethylphenol and 2,3,6-trimethylphenol, a copolymer of 2,6-dimethylphenol and o-cresol, and a copolymer of 2,6-dimethylphenol, 2,3,6-trimethylphenol and o-cresol. The production process of the above polyphenylene ether polymer is not particularly limited, and the polyphenylene ether polymer may be produced by oxidative-coupling polymerization in accordance with the process disclosed by U.S. Pat. No. 4,788,277.

As for the molecular weight of the polyphenylene ether resin, the reduced viscosity (0.5 g/dl chloroform solution, 30° C.) as a molecular weight parameter is preferably 0.20 to 0.70 dl/g, more preferably 0.30 to 0.55 dl/g.

Various phenylene ether units may be contained as a partial structure in the polyphenylene ether resin as long as they do not act counter to the gist of the present invention. Examples of the structure include oxy-2-(N,N-dialkylaminomethyl)-6-methylphenylene-1,4-diyl units and oxy-2-(N-alkyl-N-phenylaminomethyl)-6-methylphenylene-1,4-diyl units as disclosed by JP-A 63-301222. A polyphenylene ether resin containing a small amount of diphenoquinone bonded to the main chain is also included.

The polyphenylene ether resin also includes a polyphenylene ether resin modified by an ethylenically unsaturated compound such as an α,β-unsaturated carboxylic acid or an anhydride thereof. When the modified polyphenylene ether resin is used, a molded product having excellent miscibility with a vinyl compound polymer and no phase separation can be provided. Examples of the α,β-unsaturated carboxylic acid or anhydride thereof include maleic anhydride, phthalic acid, itaconic anhydride, glutaconic anhydride, citraconic anhydride, aconitic anhydride, himic anhydride, 5-norbornene-2-methyl-2-carboxylic acid, maleic acid and fumaric acid. Maleic anhydride is particularly preferred.

The polyphenylene ether resin can be modified by the above ethylenically unsaturated compound by heating up to a temperature equal to or higher than the glass transition temperature of the polyphenylene ether resin in the presence or absence of an organic peroxide. In the present invention, the polyphenylene ether resin modified by the above ethylenically unsaturated compound may be used. The above ethylenically unsaturated compound may be added to be reacted with a polyphenylene ether polymer at the same time as the production of the resin composition of the present invention.

The phenolic resin used in the present invention may be any polymer having a plurality of phenolic hydroxyl groups, as exemplified by novolac type, resol type and heat reactive type resins and modified resins thereof. They may be uncured resins without adding a curing agent, half-cured resins or cured resins. Out of these, phenolic novolac resins which are nonreactive when a curing agent is not added are preferred from the viewpoints of flame retardancy, impact resistance and economy. The shape of the phenolic resin is not particularly limited and may be ground, particulate, flaky, powdery, needle-like or liquid. The above phenolic resins may be used alone or in combination of two or more. The phenolic resin is not particularly limited, and commercially available products thereof may be used.

For example, in the case of the novolac type phenolic resin, a phenol and an aldehyde are fed to a reactor in a molar ratio of 1:07 to 1:0.9, a catalyst such as oxalic acid, hydrochloric acid, sulfuric acid or toluenesulfonic acid is added, and then heating and a reflux reaction are carried out. The novolac type phenolic resin is obtained by vacuum dehydration or static dehydration for the removal of the produced water and further removing remaining water and an unreacted phenol. A co-condensed phenolic resin can be obtained by using a plurality of raw material components and can be used likewise. The resol type phenolic resin can be obtained by the same operation as the novolac type phenolic resin after a phenol and an aldehyde are fed to a reactor in a molar ratio of 1:1 to 1:2 and a catalyst such as sodium hydroxide, ammonia water or another basic substance is added. Examples of the phenol include phenol, o-cresol, m-cresol, p-cresol, thymol, p-tert-butylphenol, tert-butyl catechol, catechol, isoeugenol, o-methoxyphenol, 4,4'-dihydroxyphenylpropane, isoamyl salicylate, benzyl salicylate, methyl salicylate and 2,6-di-tert-butyl-p-cresol. These phenols may be used alone or in combination of two or more as required. Examples of the aldehyde include formaldehyde, paraformaldehyde, polyoxymethylene and trioxane. These aldehydes may be used alone or in combination of two or more as required. Although the molecular weight of the phenolic resin is not particularly limited, a phenolic resin having a number average molecular weight of preferably 200 to 2,000, more preferably 400 to 1,500 is excellent in mechanical properties, moldability and economy.

The aromatic epoxy resin and the phenoxy resin used in the present invention are an epoxy resin and a phenoxy resin synthesized from an aromatic polyol and epihalogenohydrin. Out of these, an epoxy resin and a phenoxy resin formed from a condensation reaction between bisphenol A and epichlorohydrin are particularly preferred. The average molecular weight of each of these resins is preferably 10,000 to 50,000, more preferably 10,000 to 40,000. Examples of the aromatic epoxy resin include the Epotot YD series of Toto Kasei Co., Ltd. and examples of the phenoxy resin include the Phenotot of Toto Kasei Co., Ltd. They are easily acquired from the market.

The content of the aromatic resin is preferably 0.1 to 30 parts by weight, more preferably 0.5 to 25 parts by weight, much more preferably 1 to 20 parts by weight based on 100 parts by weight of the resin component (component A).

Examples of the fluorine-containing polymer having fibril forming ability used in the present invention include polytetrafluoroethylene, tetrafluoroethylene-based copolymer (such as a copolymer of tetrafluoroethylene and hexafluoropropylene), partially fluorinated polymers disclosed by U.S. Pat. No. 4,379,910 and polycarbonate resins produced from fluorinated diphenols. Out of these, polytetrafluoroethylene (to be abbreviated as PTFE hereinafter) is preferred.

The polytetrafluoroethylene having fibril forming ability (fibrillated PTFE) has an extremely high molecular weight and tends to become fibrous through the bonding of PTFE's by an external function such as shear force. The number average molecular weight thereof is preferably 1,500,000 to several tens of million. The lower limit of the number average molecular weight is more preferably 3,000,000. The number average molecular weight is calculated based on the melt viscosity of polytetrafluoroethylene at 380° C. as disclosed by JP-A 6-145520. That is, the fibrillated PTFE has a melt viscosity measured at 380° C. by the method disclosed by the above publication of preferably $10^7$ to $10^{13}$ poise, more preferably $10^8$ to $10^{12}$ poise.

The PTFE in a solid form and an aqueous dispersion form may be used. A mixture of PTFE having fibril forming ability and another resin may be used to improve dispersibility in a resin and obtain high flame retardancy and mechanical properties. As disclosed by JP-A 6-145520, a polymer having a core-shell structure that the core is made of fibrillated PTFE and the shell is made of low-molecular weight polytetrafluoroethylene is preferably used as well.

Commercially available products of the fibrillated PTFE include the Teflon (registered trademark) 6J of Mitsui•DuPont Florochemical Co., Ltd. and the Polyfuron MPA FA 500 and F-201L of Daikin Industries, Ltd. Typical commercially available products of the fibrillated PTFE aqueous dispersion include the Fluon AD-1 and AD-936 of Asahi ICI Fluoropolymers Co., Ltd., the Fluon D-1 and D-2 of Daikin Industries, Ltd. and the Teflon (registered trademark) 30J of Mitsui•DuPont Florochemical Co., Ltd.

The fibrillated PTFE mixture may be obtained by (1) a method in which a fibrillated PTFE aqueous dispersion and an aqueous dispersion or solution of an organic polymer are mixed together and co-precipitation is carried out to obtain a coaggregated mixture (disclosed by JP-A 60-258263 and JP-A 63-154744), (2) a method in which a fibrillated PTFE aqueous dispersion and dried organic polymer particles are mixed together (disclosed by JP-A 4-272957), (3) a method in which a fibrillated PTFE aqueous dispersion and an organic polymer particle solution are mixed together uniformly and media are removed from the mixture at the same time (disclosed by JP-A 06-220210 and JP-A 08-188653), (4) a method in which a monomer for forming an organic polymer is polymerized in a fibrillated PTFE aqueous dispersion (disclosed by JP-A 9-95583), and (5) a method in which a PTFE aqueous dispersion and an organic polymer dispersion are mixed together uniformly and a vinyl-based monomer is polymerized in the mixed dispersion to obtain a mixture (disclosed by JP-A 11-29679). Commercially available products of these fibrillated PTFE mixtures include the Metabrene A3800 (trade name) of Mitsubishi Rayon Co., Ltd., the BLENDEX B449 (trade name) of GE Specialty Chemicals Co., Ltd. and the POLY TS AD001 (trade name) of Pacific Interchem Corporation. The content of the fibrillated PTFE is preferably 10 to 80 wt %, more preferably 15 to 75 wt % based on 100 wt % of the mixture. When the content of the fibrillated PTFE falls within the above range, the high dispersibility of the fibrillated PTFE can be obtained.

The content of the fluorine-containing polymer having fibril forming ability is preferably 0.01 to 3 parts by weight, more preferably 0.01 to 2 parts by weight, much more preferably 0.05 to 1.5 parts by weight based on 100 parts by weight of the resin component (component A). The above aromatic resin and the fluorine-containing polymer having fibril forming ability may be used in combination according to use and purpose.

<Optical Stabilizer>

The resin composition of the present invention may comprise an optical stabilizer. The optical stabilizer is selected from a benzophenone-based compound, a benzotriazole-based compound, an aromatic benzoate-based compound, an anilide oxalate-based compound, a cyanoacrylate-based compound and a hindered amine-based compound.

Examples of the benzophenone-based compound include benzophenone, 2,4-dihydroxybenzophenone, 2,2'-dihydroxybenzophenone, 2,2',4,4'-tetrahydroxybenzophenone, 2-hydroxy-4-methoxybenzophenone, 2,2'-dihydroxy-4,4'-dimethoxybenzophenone, 2,2'-dihydroxy-4,4'-dimethoxy-5-sulfobenzophenone and 2-hydroxy-4-octoxybenzophenone.

Examples of the benzotriazole-based compound include 2-(5-methyl-2-hydroxyphenyl)benzotriazole, 2-(3,5-di-tert-butyl-2-hydroxyphenyl)benzotriazole and 2-(3,5-di-tert-amyl-2-hydroxyphenyl)benzotriazole.

Examples of the aromatic benzoate-based compound include alkylphenyl salicylates such as p-tert-butylphenyl salicylate and p-octylphenyl salicylate.

Examples of the anilide oxalate-based compound include 2-ethoxy-2'-ethyloxalic acid bisanilide, 2-ethoxy-5-tert-butyl-2'-ethyloxalic acid bisanilide and 2-ethoxy-3'-dodecyloxalic acid bisanilide.

Examples of the cyanoacrylate-based compound include ethyl-2-cyano-3,3'-diphenyl acrylate and 2-ethylhexyl-cyano-3,3'-diphenyl acrylate.

Examples of the hindered amine-based compound include 4-acetoxy-2,2,6,6-tetramethylpiperidine, 4-stearoyloxy-2,2,6,6-tetramethylpiperidine, 4-acryloyloxy-2,2,6,6-tetramethylpiperidine, 4-(phenylacetoxy)-2,2,6,6-tetramethylpiperidine, 4-benzoyloxy-2,2,6,6-tetramethylpiperidine, 4-methoxy-2,2,6,6-tetramethylpiperidine, 4-octadecyloxy-2,2,6,6-tetramethylpiperidine and 4-cyclohexyloxy-2,2,6,6-tetramethylpiperidine.

The content of the optical stabilizer is preferably 0.01 to 3 parts by weight, more preferably 0.03 to 2 parts by weight based on 100 parts by weight of the resin component (component A).

<Crystallization Accelerator>

The resin composition of the present invention may comprise a crystallization accelerator. When the resin composition comprises the crystallization accelerator, a molded article having excellent mechanical properties, heat resistance and moldability can be obtained.

That is, by using the crystallization accelerator, the moldability and crystallinity of the polylactic acid (component A-α) are improved, the polylactic acid is fully crystallized even by ordinary injection molding, and a molded article having excellent heat resistance and moist heat resistance stability can be obtained. In addition, the time required for the manufacture of a molded article can be drastically shortened with the result that its economic effect is large.

Both an inorganic crystallization nucleating agent and an organic crystallization nucleating agent may be used as the crystallization accelerator. Examples of the inorganic crystallization nucleating agent include talc, kaolin, silica, synthetic mica, clay, zeolite, graphite, carbon black, zinc oxide, magnesium oxide, titanium oxide, calcium carbonate, calcium sulfate, barium sulfate, calcium sulfide, boron nitride, montmorillonite, neodymium oxide, aluminum oxide and phenylphosphonate metal salts. These inorganic crystallization nucleating agents are preferably treated with a dispersion aid so as to improve their dispersibility in the resin composition and their effect so that they are highly dispersed to such an extent that their primary particle diameters become about 0.01 to 0.5 μm.

Examples of the organic crystallization nucleating agent include organic metal carboxylates such as calcium benzoate, sodium benzoate, lithium benzoate, potassium benzoate, magnesium benzoate, barium benzoate, calcium oxalate, disodium terephthalate, dilithium terephthalate, dipotassium terephthalate, sodium laurate, potassium laurate, sodium myristate, potassium myristate, calcium myristate, barium myristate, sodium octanoate, calcium octanoate, sodium stearate, potassium stearate, lithium stearate, calcium stearate, magnesium stearate, barium stearate, sodium montanate, calcium montanate, sodium toluoylate, sodium salicylate, potassium salicylate, zinc salicylate, aluminum dibenzoate, sodium β-naphthoate, potassium β-naphthoate and sodium cyclohexanecarboxylate, and organic metal sulfonates such as sodium p-toluenesulfonate and sodium sulfoisophthalate.

Organic carboxylic acid amides such as stearic acid amide, ethylenebis lauric acid amide, palmitic acid amide, hydroxystearic acid amide, erucic acid amide and trimesic acid tris(tert-butylamide), low-density polyethylene, high-density polyethylene, polyisopropylene, polybutene, poly-4-methylpentene, poly-3-methylbutene-1, polyvinyl cycloalkane, polyvinyl trialkylsilane, high-melting point polylactic acid, sodium salts of an ethylene-acrylic acid copolymer, sodium salts of a styrene-maleic anhydride copolymer (so-called "ionomer"), benzylidene sorbitol and derivatives thereof such as dibenzylidene sorbitol are also included.

At least one selected from talc and organic metal carboxylates out of these is preferably used. These crystallization nucleating agents may be used alone or in combination of two or more in the present invention.

The content of the crystallization accelerator is preferably 0.01 to 30 parts by weight, more preferably 0.05 to 20 parts by weight based on 100 parts by weight of the resin component (component A).

<Organic Filler>

The resin composition of the present invention may comprise an organic filler. By using the organic filler, a resin composition having excellent mechanical properties, heat resistance and moldability can be obtained.

Examples of the organic filler include chip fillers such as rice husk chips, wooden chips, bean curd refuse, old paper crushed chips and apparel crushed chips, fibrous fillers such as plant fibers including cotton fibers, hemp fibers, bamboo fibers, wooden fibers, kenaf fibers, jute fibers, banana fibers and coconut fibers, pulp and cellulose fibers obtained from these plant fibers, animal fibers including silk, wool, Angora, cashmere and camel fibers, and synthetic fibers including polyester fibers, nylon fibers and acrylic fibers, and powdery fillers such as paper powders, wooden powders, cellulose powders, rice husk powders, fruit shell powders, chitin powders, chitosan powders, protein powders and starch powders. From the viewpoint of moldability, powdery fillers such as paper powders, wooden powders, bamboo powders, cellulose powders, kenaf powders, rice husk powders, fruit shell powders, chitin powders, chitosan powders, protein powders and starch powders are preferred, and paper powders, wooden powders, bamboo powders, cellulose powders and kenaf powders are more preferred. Paper powders and wooden powders are much more preferred. Paper powders are particularly preferred.

Organic fillers directly obtained from natural products may be used, and organic fillers recycled from waste materials such as used paper, waste timber and used clothing may also be used. Conifers such as yellow pine, cedar, cypress and fir, and broadleaf trees such as beech, chinquapin and eucalyptus are preferred as timber.

Paper powders preferably contain an adhesive, especially an emulsion-based adhesive such as vinyl acetate resin-based emulsion or acrylic resin-based emulsion which is generally used to process paper, or a hot melt adhesive such as polyvinyl alcohol-based adhesive or polyamide-based adhesive from the viewpoint of moldability.

The content of the organic filler is preferably 1 to 300 parts by weight, more preferably 5 to 200 parts by weight, much more preferably 10 to 150 parts by weight, particularly preferably 15 to 100 parts by weight based on 100 parts by weight of the resin component (component A) from the viewpoints of moldability and heat resistance.

<Release Agent>

The resin composition of the present invention may comprise a release agent. The release agent is selected from a fatty acid, a fatty acid metal salt, an oxyfatty acid, a paraffin, a low-molecular weight polyolefin, a fatty acid amide, an alkylenebis fatty acid amide, an aliphatic ketone, a fatty acid partially saponified ester, a fatty acid lower alcohol ester, a fatty acid polyhydric alcohol ester, a fatty acid polyglycol ester and a modified silicone. When the resin composition comprises a release agent, a molded article having excellent mechanical properties, moldability and heat resistance can be obtained.

The fatty acid is preferably a fatty acid having 6 to 40 carbon atoms, as exemplified by oleic acid, stearic acid, lauric acid, hydroxystearic acid, behenic acid, arachidonic acid, linoleic acid, linolenic acid, ricinoleic acid, palmitic acid, montanic acid and mixtures thereof. The fatty acid metal salt is preferably an alkali (earth) metal salt of a fatty acid having 6 to 40 carbon atoms, as exemplified by calcium stearate, sodium montanate and calcium montanate.

Examples of the oxyfatty acid include 1,2-oxystearic acid. The paraffin is preferably a paraffin having 18 or more carbon atoms, as exemplified by liquid paraffin, natural paraffin, microcrystalline wax and petrolactam.

The low-molecular weight polyolefin is preferably a polyolefin having a molecular weight of 5,000 or less, as exemplified by polyethylene wax, maleic acid modified polyethylene wax, oxide type polyethylene wax, chlorinated polyethylene wax and polypropylene wax. The fatty acid amide is preferably a fatty acid amide having 6 or more carbon atoms, as exemplified by oleic acid amide, erucic acid amide and behenic acid amide.

The alkylenebis fatty acid amide is preferably an alkylenebis fatty acid amide having 6 or more carbon atoms, as exemplified by methylenebis stearic acid amide, ethylenebis stearic acid amide and N,N-bis(2-hydroxyethyl)stearic acid amide. The aliphatic ketone is preferably an aliphatic ketone having 6 or more carbon atoms, as exemplified by higher aliphatic ketones.

Examples of the fatty acid partially saponified ester include montanic acid partially saponified esters. Examples of the fatty acid lower alcohol ester include stearic acid esters, oleic acid esters, linoleic acid esters, linolenic acid esters, adipic acid esters, behenic acid esters, arachidonic acid esters, montanic acid esters and isostearic acid esters.

Examples of the fatty acid polyhydric alcohol ester include glycerol tristearate, glycerol distearate, glycerol monostearate, pentaerythritol tetrastearate, pentaerythritol tristearate, pentaerythritol dimyristate, pentaerythritol monostearate, pentaerythritol adipate stearate and sorbitan monobehenate. Examples of the fatty acid polyglycol ester include polyethylene glycol fatty acid esters, polytrimethylene glycol fatty acid esters and polypropylene glycol fatty acid esters.

Examples of the modified silicone include polyether modified silicone, higher fatty acid alkoxy modified silicone, higher fatty acid-containing silicone, higher fatty acid ester modified silicone, methacryl modified silicone and fluorine modified silicone.

Out of these, fatty acids, fatty acid metal salts, oxyfatty acids, fatty acid esters, fatty acid partially saponified esters, paraffins, low-molecular weight polyolefins, fatty acid amides and alkylenebis fatty acid amides are preferred, and fatty acid partially saponified esters and alkylenebis (fatty acid amides) are more preferred. Montanic acid esters, montanic acid partially saponified esters, polyethylene wax, oxide type polyethylene wax, sorbitan fatty acid esters, erucic acid amide and ethylenebis stearic acid amide are much more preferred, and montanic acid partially saponified esters and ethylenebis stearic acid amide are particularly preferred.

These release agents may be used alone or in combination of two or more. The content of the release agent is preferably 0.01 to 3 parts by weight, more preferably 0.03 to 2 parts by weight based on 100 parts by weight of the resin component (component A).

<Antistatic Agent>

The resin composition of the present invention may comprise an antistatic agent. Examples of the antistatic agent include quaternary ammonium salt-based and sulfonate-based compounds such as (β-lauramidepropionyl) trimethylammonium sulfate and sodium dodecylbenzenesulfonate, and alkyl phosphate-based compounds. These antistatic agents may be used alone or in combination of two or more. The content of the antistatic agent is preferably 0.05 to 5 parts by weight, more preferably 0.1 to 5 parts by weight based on 100 parts by weight of the resin component (component A).

<Plasticizer>

The resin composition of the present invention may comprise a plasticizer. The plasticizer is selected from a polyester-based plasticizer, a glycerin-based plasticizer, a polycarboxylate-based plasticizer, a phosphate-based plasticizer, a polyalkylene glycol-based plasticizer and an epoxy-based plasticizer.

Examples of the polyester-based plasticizer include polyesters comprising an acid component such as adipic acid, sebacic acid, terephthalic acid, isophthalic acid, naphthalenedicarboxylic acid or diphenyldicarboxylic acid and a diol component such as ethylene glycol, 1,3-propanediol, propylene glycol, 1,3-butanediol, 1,4-butanediol, 1,6-hexanediol or diethylene glycol, and polyesters comprising a hydroxycarboxylic acid such as polycaprolactone. The ends of these polyesters may be sealed by a monofunctional carboxylic acid or a monofunctional alcohol.

Examples of the glycerin-based plasticizer include glycerin monostearate, glycerin distearate, glycerin monoacetomonolaurate, glycerin monoacetomonostearate, glycerin diacetomonooleate and glycerin monoacetomonomontanate.

Examples of the polycarboxylate-based plasticizer include phthalates such as dimethyl phthalate, diethyl phthalate, dibutyl phthalate, diheptyl phthalate, dibenzyl phthalate and butylbenzyl phthalate, trimellitates such as tributyl trimellitate, trioctyl trimellitate and trihexyl trimellitate, adipates such as isodecyl adipate and n-decyl-n-octyl adipate, citrates such as tributyl acetylcitrate, azelates such as bis(2-ethylhexyl)azelate, and sebacates such as dibutyl sebacate and bis(2-ethylhexyl)sebacate.

Examples of the phosphate-based plasticizer include tributyl phosphate, tris(2-ethylhexyl)phosphate, trioctyl phosphate, triphenyl phosphate, tricresyl phosphate and diphenyl-2-ethylhexyl phosphate.

Examples of the polyalkylene glycol-based plasticizer include polyalkylene glycols such as polyethylene glycol, polytrimethylene glycol, polypropylene glycol, polytramethylene glycol, poly(ethylene oxide-propylene oxide) block or random copolymer, ethylene oxide addition polymers of a bisphenol and tetrahydrofuran addition polymers of a bisphenol, and end-sealing compounds such as terminal epoxy modified compounds, terminal ester modified compounds and terminal ether modified compounds thereof.

Examples of the epoxy-based plasticizer include epoxy triglyceride comprising alkyl epoxystearate and soybean oil, and epoxy resin obtained from bisphenol A and epichlorohydrin.

Other examples of the plasticizer include benzoates of an aliphatic polyol such as neopentyl glycol dibenzoate, diethylene glycol dibenzoate and triethylene glycol-bis(2-ethylbutyrate), fatty acid amides such as stearic acid amide, fatty acid esters such as butyl oleate, oxyacid esters such as methyl acetyl ricinoleate and butyl acetyl ricinoleate, pentaerythritol, sorbitols, polyacrylates, silicone oil and paraffins.

The plasticizer is preferably at least one selected from polyester-based plasticizers and polyalkylene-based plasticizers. They may be used alone or in combination of two or more.

The content of the plasticizer is preferably 0.01 to 30 parts by weight, more preferably 0.05 to 20 parts by weight, much more preferably 0.1 to 10 parts by weight based on 100 parts by weight of the resin component (component A). In the present invention, a crystallization nucleating agent and a plasticizer may be used independently but preferably in combination.

<Others>

The resin composition of the present invention may comprise a thermosetting resin such as phenolic resin, melamine resin, thermocurable polyester resin, silicone resin or epoxy resin, or a thermoplastic resin such as polyarylate resin, liquid crystalline polyester resin, polyamide resin, polyimide resin, polyether imide resin, polyphenylene ether resin, polyphenylene sulfide resin, polysulfone resin, polystyrene resin, acrylonitrile/styrene copolymer (AS resin), polystyrene resin, high-impact polystyrene resin or syndiotactic polystyrene resin as long as it does not act counter to the gist of the present invention.

The resin composition may further comprise a colorant including an organic or inorganic dye or pigment, for example, an oxide such as titanium dioxide, a hydroxide such as alumina white, a sulfide such as zinc sulfide, a ferrocyanide such as iron blue, a chromate such as zinc chromate, a sulfate such as barium sulfate, a carbonate such as calcium carbonate, a silicate such as ultramarine blue, a phosphate such as manganese violet, carbon such as carbon black, or a metal colorant such as bronze powder or aluminum powder.

The resin composition may still further comprise a nitroso-based condensation polycyclic colorant such as Naphthol Green B, a nitro-based condensation polycyclic colorant such as Naphthol Yellow S, an azo-based condensation polycyclic colorant such as Naphthol Red or Chromophthal Yellow, a phthalocyanine-based condensation polycyclic colorant such as Phthalocyanine Blue or Fast Sky Blue, or Indanthrene Blue, and a slidability modifier such as graphite or fluororesin. These additives may be used alone or in combination of two or more.

<Production Process of Resin Composition>

(i) Preparation of Coexistence Composition

When a mixture of poly-L-lactic acid (component A-α-1) and poly-D-lactic acid (component A-α-2) is used as the polylactic acid (component A-α) in the present invention, before the mixture is melt mixed with other additives, a phosphate metal salt (s) represented by the formula (3) and/or the formula (4), poly-L-lactic acid (component A-α-1) and poly-D-lactic acid (component A-α-2) are preferably coexistent in advance. To make them coexistent, a method in which poly-L-lactic acid (component A-α-1) and poly-D-lactic acid (component A-α-2) are mixed together as uniformly as possible is preferably employed because a stereocomplex crystal can be formed efficiently when they are heated. The method of preparing the coexistence composition is not particularly limited if poly-L-lactic acid (component A-α-1) and poly-D-lactic acid (component A-α-2) are uniformly mixed together when they are heated, as exemplified by a method in which the coexistence composition is prepared in the presence of a solvent and a method in which the coexistence composition is prepared in the absence of a solvent.

To carry out the preparation of the above coexistence composition in the presence of a solvent, a method in which the coexistence composition is obtained by re-precipitation from a solution thereof and a method in which the coexistence composition is obtained by removing the solvent by heating are preferably employed.

To obtain the coexistence composition by re-precipitation in the presence of a solvent, the coexistence composition comprising poly-L-lactic acid (component A-α-1) and poly-D-lactic acid (component A-α-2) is first prepared by re-precipitation. Preferably, a solution of the component A-α-1 dissolved in a solvent and a solution of the component A-α-2 dissolved in a solvent are prepared separately and mixed together, or both of them are dissolved in a solvent and mixed together.

It is preferred that the weight ratio (component A-α-1/component A-α-2) of the poly-L-lactic acid (component A-α-1) to the poly-D-lactic acid (component A-α-2) should be adjusted to 10/90 to 90/10 so as to produce the stereocomplex crystal of polylactic acids (component A-α-1, component A-α-2) efficiently in the resin composition of the present invention. The weight ratio of the component A-α-1 to the component A-α-2 is more preferably 25/75 to 75/25, much more preferably 40/60 to 60/40.

The solvent is not particularly limited as long as it dissolves the polylactic acids (component A-α-1, component A-α-2), and preferred examples thereof include chloroform, methylene chloride, dichloroethane, tetrachloroethane, phenol, tetrahydrofuran, N-methylpyrrolidone, N,N-dimethylformamide, butyrolactone, trioxane, hexafluoroisopropanol and a mixture of two or more thereof.

Since the phosphate metal salt represented by the formula (3) or (4) is insoluble in the above solvent or remains in the solvent after re-precipitation when it dissolves in the solvent, the coexistence composition must be prepared by mixing a mixture of the polylactic acids (component A-α-1, component A-α-2) obtained by re-precipitation and the phosphate metal salt represented by the formula (3) or (4)

separately. The method of obtaining the coexistence composition comprising a mixture of the polylactic acids (component A-α-1, component A-α-2) and the phosphate metal salt represented by the formula (3) or (4) is not particularly limited if they are uniformly mixed together, and any method in which they are mixed together in a powdery form or they are melt mixed together may be employed.

Then, to prepare the coexistence composition comprising the polylactic acids (component A-α-1, component A-α-2) and the phosphate metal salt represented by the formula (3) or (4) at a time by removing a solvent in the presence of the solvent, a dispersion of the polylactic acids (component A-α-1, component A-α-2) dissolved or dispersed in a solvent or a dispersion of the phosphate metal salt represented by the formula (3) or (4) dissolved or dispersed in a solvent are prepared separately and mixed together, or a dispersion of all the components dissolved or dispersed in a solvent is prepared and mixed, and then the solvent is evaporated by heating. The solvent is not particularly limited as long as it dissolves the polylactic acids (component A-α-1, component A-α-2) and the phosphate metal salt represented by the formula (3) or (4). Preferred examples thereof include chloroform, methylene chloride, dichloroethane, tetrachloroethane, phenol, tetrahydrofuran, N-methylpyrrolidone, N,N-dimethylformamide, butyrolactone, trioxane, hexafluoroisopropanol and a mixture of two or more thereof. Since the solvent may be decomposed when the heat treatment is carried out for a long time, the temperature elevation rate of the heat treatment after the evaporation of the solvent is preferably high but not particularly limited.

The preparation of the coexistence composition comprising the polylactic acids (component A-α-1, component A-α-2) and the phosphate metal salt represented by the formula (3) or (4) may be carried out in the absence of a solvent. That is, predetermined amounts of the component A-α-1 and the component A-α-2 which have been powdered or chipped in advance and a predetermined amount of the phosphate metal salt represented by the formula (3) or (4) are mixed together and melt mixed together, or either one of the component A-α-1 and the component A-α-2 is molten and the remaining components are added to and mixed with that component.

The size of the above powder or chip is not particularly limited if the powders or chips of the polylactic acid units (component A-α-1, component A-α-2) are uniformly mixed together but preferably 3 mm or less, more preferably 1 to 0.25 mm. When they are melt mixed together, regardless of the sizes of these components, a stereocomplex crystal is formed. However, when the powders or chips are simply molten after they are uniformly mixed together, if the diameter of each of the powders or the chips is 3 mm or more, mixing becomes nonuniform and a homopolylactic acid crystal is apt to separate out disadvantageously. As a mixer used to mix together the above powders or the above chips uniformly, a reactor equipped with a batch type stirring blade, a continuous reactor or a double-screw or single-screw extruder may be preferably used to mix them together by melting, and a tumbler powder mixer, a continuous powder mixer or various milling machines may be preferably used to mix together the powders.

When the coexistence composition is to be prepared, a cyclic carbodiimide (component B), an antioxidant (component C), an end-sealing agent (component D), a hydrotalcite (component E), an impact modifier (component F), a flame retardant (component G), an inorganic filler (component H) and other additives such as an inorganic filler bending inhibitor, a lubricant, an ultraviolet absorbent, an optical stabilizer, a release agent, a flowability modifier, a colorant, a light diffusing agent, a fluorescent brightener, a light accumulating pigment, a fluorescent dye, an antistatic agent, an antibacterial agent, a crystal nucleating agent and a plasticizer may be coexistent.

Addition of the cyclic carbodiimide (component B) and the end-sealing agent (component D) in the stage of preparing the coexistence composition is preferred for the improvement of the hydrolysis resistance of the finally obtained resin composition because the end-sealing agent and the polylactic acid (component A) are mixed together uniformly, thereby sealing the acidic end of the polylactic acid more efficiently. Addition of an antioxidant such as a hindered phenol-based compound, a phosphite-based compound, a phosphonite-based compound or a thioether-based compound in the stage of preparing the coexistence composition is particularly preferred for the improvement of heat stability in the subsequent stage of the heat treatment of the coexistence composition.

(ii) Heat Treatment of Coexistence Composition

When a mixture of poly-L-lactic acid (component A-α-1) and poly-D-lactic acid (component A-α-2) is used as the polylactic acid (component A-α) in the present invention, before the mixture is melt mixed with other additives, the coexistence composition of the polylactic acids (component A-α-1, component A-α-2) and the phosphate metal salt represented by the formula (3) or (4) is preferably heated. This heat treatment is to keep the composition at a temperature range of 240 to 300° C. for a certain period of time. The heat treatment temperature is preferably 250 to 300° C., more preferably 260 to 290° C. When the temperature is higher than 300° C., it is difficult to suppress a decomposition reaction and when the temperature is lower than 240° C., uniform mixing by the heat treatment does not proceed and a stereocomplex crystal is hardly formed efficiently disadvantageously. The heat treatment time which is not particularly limited is 0.2 to 60 minutes, preferably 1 to 20 minutes. The atmosphere at the time of the heat treatment is an inert atmosphere at normal pressure or reduced pressure. As the apparatus and method used for the heat treatment, any apparatus and any method may be used if they are capable of heating while the control of the atmosphere is carried out. For example, a method in which the composition is processed by using a batch reactor, a continuous reactor, a double-screw or single-screw extruder, a press or flow pipe type extruder while it is molded may be employed. When the coexistence composition of the polylactic acids (component A-α-1, component A-α-2) and the phosphate metal salt represented by the formula (3) or (4) is to be prepared by melt mixing in the absence of a solvent, the heat treatment of the coexistence composition can be carried out at the same time as the preparation of the coexistence composition.

(iii) Preparation of Resin Composition

The resin composition of the present invention is manufactured by mixing together the polylactic acid (component A) (including the above heated coexistence composition), the cyclic carbodiimide (component B), the antioxidant (component C), the end-sealing agent (component D), the hydrotalcite (component E), the inorganic filler (component F) and other additive components. (components contained in the coexistence composition are excluded.) The other additive components include an inorganic filler bending inhibitor, a lubricant, an ultraviolet absorbent, an optical stabilizer, a release agent, a flowability modifier, a colorant, a light diffusing agent, a fluorescent brightener, a light accumulating pigment, a fluorescent dye, an antistatic agent, an antibacterial agent, a crystal nucleating agent and a plasticizer.

To produce the resin composition of the present invention any process is employed. For example, the polylactic acid (component A) and other components are premixed together, melt kneaded together and pelletized. Examples of the premixing means include a Nauter mixer, a twin-cylinder mixer, a Henschel mixer, a mechanochemical device and an extrusion mixer. During premixing, the resulting mixture may be granulated by means of an extrusion granulator or a briquetting machine according to circumstances. After premixing, the obtained product is melt kneaded by means of a melt kneader typified by a vented double-screw extruder and pelletized by means of a device such as a pelletizer. Other examples of the melt kneader include a Banbury mixer, a kneading roll and a constant heat stirring vessel, and a vented double-screw extruder is preferred. The components may be supplied into a melt kneader typified by a double-screw extruder independently without being premixed together.

The present invention includes a process for producing the above resin composition, comprising the steps:
(i) preparing a stereocomplex polylactic acid by melt kneading together poly-L-lactic acid (component A-α-1) and poly-D-lactic acid (component A-α-2) in a weight ratio of 10:90 to 90:10; and
(ii) melt kneading together (A) 100 parts by weight of a resin component (component A) containing the stereocomplex polylactic acid, (B) 0.001 to 10 parts by weight of a cyclic carbodiimide compound (component B) having one carbodiimide group and a cyclic structure represented by the formula (5) in which first nitrogen and second nitrogen are bonded to each other via a bonding group, the cyclic structure consisting of 8 to 50 atoms, and (C) 0.001 to 2 parts by weight of at least one antioxidant (component C) selected from the group consisting of a hindered phenol-based compound, a phosphite-based compound, a phosphonite-based compound and a thioether-based compound.

The present invention also includes the above production process in which the resin component (component A) contains 5 to 95 wt % of a stereocomplex polylactic acid (component A-α-3) and 95 to 5 wt % of at least one thermoplastic resin (component A-β) selected from the group consisting of an aromatic polyester (component A-β-1), a polyolefin (component A-β-2) and an aromatic polycarbonate (component A-β-3).

According to the production process of the resin composition of the present invention, since a cyclic carbodiimide component (component B) is used as an end-sealing agent, the release of a compound having an isocyanate group is prevented so that the resin composition can be manufactured in a good work environment.

When a linear carbodiimide compound ($R_1$—N=C=N—$R_2$) is used as an end-sealing agent for a polymer having a terminal carboxyl group, a reaction represented by the following formula takes place. In the formula, W is the main chain of the polymer. The linear carbodiimide compound reacts with the carboxyl group to form an amido group at the end of the polymer, thereby releasing an isocyanate compound ($R_1NCO$).

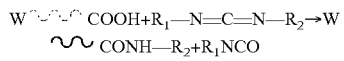

On the other hand, when a cyclic carbodiimide compound (component B) is used as an end-sealing agent for a polymer having a terminal carboxyl group, a reaction represented by the following formula takes place. The cyclic carbodiimide compound (component B) reacts with the carboxyl group to form an isocyanate group (—NCO) via the amido group at the end of the polymer, thereby not releasing the isocyanate group.

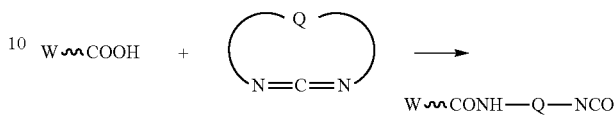

Since the cyclic carbodiimide compound used in the present invention does not contain a long chain, it can be used to seal the end of a polymer having excellent heat resistance and a high melting point.

<Molded Article>

The present invention includes a molded article of the above resin composition. Examples of the molded article include car parts, electric/electronic parts, electric equipment exterior parts and OA exterior parts.

The resin composition of the present invention is generally obtained as a pellet produced by the above process from which products can be manufactured by various molding methods such as injection molding, extrusion molding, thermo-molding and blow molding.

In injection molding, not only ordinary cold runner systems but also hot runner systems can be used. Molded articles can be obtained by using not only ordinary molding methods but also injection molding methods such as injection compression molding, injection press molding, gas assist injection molding, foam molding (including what comprises the injection of a super-critical fluid), insert molding, in-mold coating molding, insulated runner molding, quick heat and cool molding, two-color molding, sandwich molding and super high-speed injection molding according to purpose. The advantages of these molding methods are already widely known.

Profile extrusion molded articles, sheets and films can be obtained by extrusion molding. For the molding of a sheet or a film, an inflation, calendering or casting method may also be used. Further, the resin composition can be molded into a heat shrinkable tube by carrying out specific stretching operation.

The resin composition of the present invention can be formed into a hollow molded article by rotational molding or blow molding as well.

Molded articles molded from the resin composition of the present invention are suitable for use as electric/electronic parts and exterior materials for OA equipment and home electric appliances. Examples thereof include exterior materials for personal computers, notebook personal computers, game machines (such as game machines for home use, game machines for business use, pachinko machines and slot machines), displays (such as CRT, liquid crystal, plasma, projector and organic EL displays), mice, printers, copiers, scanners and facsimiles (including composite machines thereof), electric/electronic parts and switch molded articles such as keys for keyboards and various switches. Further, the molded articles of the present invention are very useful for other wide purposes, for example, electric and electronic equipment such as portable digital assistants (so-called PDA), cell-phones, portable books (such as dictionaries), portable TVs and drives for recording media (such as CD, MD, DVD, next-generation high-density disks and hard disks), readers for recording media (IC cards, smart media and memory sticks), optical cameras, digital cameras, parabolic antennas, electric power tools, VTR's, irons, hair driers, rice cookers, microwave ovens, audio equipment, lighting equipment, refrigerators, air conditioners, air cleaners, minus ion generators and typewriters. The molded articles of the present invention can be used as various parts such as exterior materials for these. They are also suitable for use in miscellaneous goods such as containers, covers, writing things and ornaments. Further, car parts such as lamp sockets, lamp reflectors, lamp housings, instrumental panels, center console panels, deflector parts, car navigation parts, car audio visual parts and auto mobile computer parts are also included.

Further, other functions can be provided to molded articles molded from the resin composition of the present invention by carrying out surface modification. The surface modification as used herein refers to deposition (physical deposition, chemical deposition, etc.), plating (electroplating, electroless plating, hot dipping, etc.), painting, coating or printing, all of which are used to form a new layer on the surface layer of a resin molded article, and a method which is used for ordinary resin molded articles can be employed.

EXAMPLES

The following examples are provided to further illustrate the present invention. The present invention is not limited to these.

1. Production of Polylactic Acid

The production of the polylactic acid was carried out by the process shown in the following production examples. Values in the production examples were obtained by the following methods.

(1) Weight average molecular weight (Mw) and number average molecular weight (Mn) of polymer They were measured by gel permeation chromatography (GPC) and calculated in terms of standard polystyrene. GPC measurement equipment include the RID-6A differential refractometer of Shimadzu Corporation as a detector and the TSKgelG3000HXL of Tosoh Corporation as a column. Measurement was carried out by using chloroform as an eluant and injecting 10 μl of a sample having a concentration of 1 mg/ml (chloroform containing 1% of hexafluoroisopropanol) at a temperature of 40° C. and a flow rate of 1.0 ml/min.

(2) carboxyl group concentration

The sample was dissolved in purified o-cresol in a nitrogen gas stream and titrated with an ethanol solution of 0.05 N potassium hydroxide by using Bromocresol Blue as an indicator.

(3) stereocomplex crystal rate

The stereocomplex crystal rate was evaluated from the following equation using melting enthalpy derived from the polylactic acid (component A) crystal in the temperature elevation step of DSC (TA-2920 of TA Instrument Co., Ltd.) measurement.

Stereocomplex crystal rate=$\Delta Hms/(\Delta Hms+\Delta Hmh) \times 100$

[In the above equation, $\Delta Hmh$ and $\Delta Hms$ are the melting enthalpy of a crystal melting point ($\Delta Hmh$) which appears at a temperature lower than 190° C. and the melting enthalpy ($\Delta Hms$) of a crystal melting point which appears at a temperature of 190° C. or higher to lower than 250° C. in the temperature elevation step of a differential scanning calorimeter (DSC), respectively.]

The above $\Delta Hmh$ and $\Delta Hms$ were obtained by measuring the resin composition in a nitrogen atmosphere at a temperature elevation rate of 20° C./min by means of a differential scanning calorimeter (DSC).

The following materials were used in Examples and Comparative Examples of the present invention.

Production Example 1-1 (A-α-1: poly-L-lactic Acid (PLLA))

0.005 part by weight of tin octylate was added to 100 parts by weight of L-lactide (manufactured by Musashino Chemical Laboratory, Ltd., optical purity of 100%) to carry out a reaction in a reactor equipped with a stirring blade in a nitrogen atmosphere at 180° C. for 2 hours, phosphoric acid was added in an amount 1.2 times the equivalent of tin octylate, the remaining lactide was removed at 13.3 Pa, and the obtained product was cut into a chip to obtain poly-L-lactic acid.

The obtained poly-L-lactic acid had a weight average molecular weight of 152,000, a melting enthalpy ($\Delta Hmh$) of 49 J/g, a melting point (Tmh) of 175° C., a glass transition point (Tg) of 55° C. and a carboxyl group content of 14 eq/ton.

Production Example 1-2 (A-α-2: poly-D-lactic Acid (PDLA))

The operation of Production Example 1-1 was repeated except that D-lactide (manufactured by Musashino Chemical Laboratory, Ltd., optical purity of 100%) was used in place of L-lactide of Production Example 1-1 to obtain poly-D-lactic acid. The obtained poly-D-lactic acid had a weight average molecular weight of 151,000, a melting enthalpy ($\Delta Hmh$) of 48 J/g, a melting point (Tmh) of 175° C., a glass transition point (Tg) of 55° C. and a carboxyl group content of 15 eq/ton.

Production Example 1-3 (A-α-3: Stereocomplex Polylactic Acid (scPLA))

100 parts by weight of polylactic acids consisting of 50 parts by weight of PLLA and 50 parts by weight of PDLA obtained in Production Examples 1-1 and 1-2 and 0.1 part by weight of phosphoric acid-2,2'-methylenebis(4,6-di-tert-butylphenyl)sodium (Adecastab NA-11: ADEKA Corporation) were mixed together by means of a blender, and the resulting mixture was dried at 110° C. for 5 hours and supplied into the TEX30XSST 30 mmφ vented double-screw extruder of The Japan Steel Works, Ltd. to be melt extruded into a pellet at a cylinder temperature of 250° C., a screw revolution of 250 rpm, a discharge rate of 9 kg/h and a vent vacuum degree of 3 kPA so as to obtain polylactic acid 1. The obtained stereocomplex polylactic acid had a weight average molecular weight of 130,000, a melting enthalpy (nHms) of 56 J/g, a melting point (Tms) of 220° C., a glass transition point (Tg) of 58° C., a carboxyl group content of 17 eq/ton and a stereocomplex crystal rate of 100%.

The results are shown in Table 1-1. $\Delta Hms$ in Table 1-1 is the melting enthalpy of a crystal melting point which appears at a temperature of 190° C. or higher to lower than 250° C. and $\Delta Hmh$ is the melting enthalpy of a crystal melting point which appears at a temperature lower than 190° C. Tms is a crystal melting point which appears at a temperature of 190° C. or higher to lower than 250° C., and Tmh is a crystal melting point which appears at a temperature lower than 190° C.

TABLE 1-1

| | | Production Example | | |
|---|---|---|---|---|
| | | Production 1-1 PLLA | Production 1-2 PDLA | Production 1-3 scPLA |
| ΔHms | J/g | 0 | 0 | 56 |
| ΔHmh | J/g | 49 | 48 | 0 |
| Tms | ° C. | Not detected | Not detected | 220 |
| Tmh | ° C. | 175 | 175 | Not detected |
| Tg | ° C. | 55 | 55 | 58 |
| Stereocomplex crystal rate | % | 0 | 0 | 100 |
| Mw | (×10⁴) | 15.2 | 15.1 | 13 |
| Carboxyl group concentration | eq/ton | 14 | 15 | 17 |

2. Production of Cyclic Carbodiimide

Cyclic carboidiimides were produced by the method shown in the following production examples. Values in the production examples were obtained by the following methods.

(1) NMR identification of cyclic carbodiimide structure

The NMR identification of the synthesized cyclic carbodiimide compound was confirmed by $^1$H-NMR and $^{13}$C-NMR using the JNR-EX270 of JEOL Ltd. Heavy chloroform was used as a solvent.

(2) IR identification of carbodiimide skeleton of cyclic carbodiimide

The identification of the carbodiimide skeleton of the synthesized cyclic carbodiimide compound was carried out by confirming an absorption peak at 2,100 to 2,200 cm$^{-1}$ which is the characteristic of a carbodiimide by FT-IR using the Magna-750 of Nicoley Co., Ltd.

The following materials were used in Examples of the present invention.

Production Example 2-1 )Component B-1: Cyclic Carbodiimide (CC1))

o-nitrophenol (0.11 mol), 1,2-dibromoethane (0.05 mol), potassium carbonate (0.33 mol) and 200 ml of N,N-dimethylformamide (DMF) were fed to a reactor equipped with a stirrer and a heater in an N$_2$ atmosphere and reacted at 130° C. for 12 hours, DMF was removed under reduced pressure, the obtained solid was dissolved in 200 ml of dichloromethane, and the resulting solution was separated with 100 ml of water 3 times. An organic layer was dehydrated with 5 g of sodium sulfate and dichloromethane was removed under reduced pressure to obtain an intermediate product A (nitro derivative).

Then, the intermediate product A (0.1 mol), 5% palladium carbon (Pd/C) (1 g) and 200 ml of ethanol/dichloromethane (70/30) were fed to a reactor equipped with a stirrer, hydrogen substitution was carried out 5 times, and a reaction was carried out at 25° C. while hydrogen was always supplied and terminated when the amount of hydrogen did not decrease any more. When Pd/C was collected and the mixed solvent was removed, an intermediate product B (amine derivative) was obtained.

Then, triphenylphosphine dibromide (0.11 mol) and 150 ml of 1,2-dichloroethane were fed to a reactor equipped with a stirrer, a heater and a dropping funnel in an N$_2$ atmosphere and stirred. A solution obtained by dissolving the intermediate product B (0.05 mol) and triethylamine (0.25 mol) in 50 ml of 1,2-dichloroethane was gradually added dropwise to the resulting mixture at 25° C. After the end of addition, a reaction was carried out at 70° C. for 5 hours. Thereafter, the reaction solution was filtered, and the filtrate was separated with 100 ml of water 5 times. An organic layer was dehydrated with 5 g of sodium sulfate and 1,2-dichloroethane was removed under reduced pressure to obtain an intermediate product C (triphenylphosphine derivative).

Thereafter, di-tert-butyl dicarbonate (0.11 mol), N,N-dimethyl-4-aminopyridine (0.055 mol) and 150 ml of dichloromethane were fed to a reactor equipped with a stirrer and a dropping funnel in an N$_2$ atmosphere and stirred. 100 ml of dichloromethane containing the intermediate product C (0.05 mol) dissolved therein at 25° C. was gradually added dropwise to the resulting mixture. After the end of addition, a reaction was carried out for 12 hours. Thereafter, a solid obtained by removing dichloromethane was purified to obtain CC1. When the structure of CC1 was checked by NMR and IR, it was a structure represented by the following formula (the number of atoms in the cyclic structure is 10).

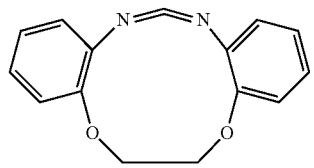 [SMILES: C1=Nc2ccccc2OCCOc2ccccc2N=1]

Production Example 2-2 (Component B-2: Production of Cyclic Carbodiimide (CC2))

o-nitrophenol (0.11 mol), pentaerythritol tetrabromide (0.025 mol), potassium carbonate (0.33 mol) and 200 ml of N,N-dimethylformamide were fed to a reactor equipped with a stirrer and a heater in an N$_2$ atmosphere and reacted at 130° C. for 12 hours, DMF was removed under reduced pressure, the obtained solid was dissolved in 200 ml of dichloromethane, and the resulting solution was separated with 100 ml of water 3 times. An organic layer was dehydrated with 5 g of sodium sulfate and dichloromethane was removed under reduced pressure to obtain an intermediate product D (nitro derivative).

Then, the intermediate product D (0.1 mol), 5% palladium carbon (Pd/C) (2 g) and 400 ml of ethanol/dichloromethane (70/30) were fed to a reactor equipped with a stirrer, hydrogen substitution was carried out 5 times, and a reaction was carried out at 25° C. while hydrogen was always supplied and terminated when the amount of hydrogen did not decrease any more. When Pd/C was collected and the mixed solvent was removed, an intermediate product E (amine derivative) was obtained.

Then, triphenylphosphine dibromide (0.11 mol) and 150 ml of 1,2-dichloroethane were fed to a reactor equipped with a stirrer, a heater and a dropping funnel in an N$_2$ atmosphere and stirred. A solution obtained by dissolving the intermediate product E (0.025 mol) and triethylamine (0.25 mol) in 50 ml of 1,2-dichloroethane was gradually added dropwise to the resulting mixture at 25° C. After the end of addition, a reaction was carried out at 70° C. for 5 hours. Thereafter, the reaction solution was filtered, and the filtrate was separated with 100 ml of water 5 times. An organic layer was dehydrated with 5 g of sodium sulfate and 1,2-dichloroethane was removed under reduced pressure to obtain an intermediate product F (triphenylphosphine derivative).

Thereafter, di-tert-butyl dicarbonate (0.11 mol), N,N-dimethyl-4-aminopyridine (0.055 mol) and 150 ml of dichloromethane were fed to a reactor equipped with a stirrer and a dropping funnel in an $N_2$ atmosphere and stirred. 100 ml of dichloromethane containing the intermediate product F (0.025 mol) dissolved therein at 25° C. was gradually added dropwise to the resulting mixture. After the end of addition, a reaction was carried out for 12 hours. A solid obtained by removing dichloromethane was purified to obtain CC2. When the structure of CC2 was confirmed by NMR and IR, it was a structure represented by the following formula (the number of atoms in the cyclic structure is 12).

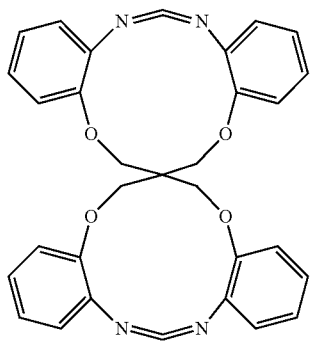 [SMILES: C1=Nc2ccccc2OCC2(COc3ccccc3N=1)COc1ccccc1N=C=Nc1ccccc1OC2]

3. Production and Evaluation of Polylactic Acid Resin Pellet

A resin composition pellet comprising polylactic acid (component A) and additives was manufactured by the method shown in the following examples and comparative examples. Values in the examples were obtained by the following methods.

(1) Evaluation of work environment

Sensory evaluation was made on whether a worker detected an irritating smell derived from an isocyanate gas or not at the time of extrusion and molding works. The work environment was evaluated as X when an irritating smell was detected and ○ when no irritating smell was not detected.

(2) qualitative and quantitative determination of isocyanate gas by GC/MS

The resin composition pellet was heated at 230° C. for minutes to carry out its qualitative and quantitative determination by pyrolysis GC/MS analysis. The quantitative determination was made by using an analytical curve formed with an isocyanate. The GC/MS Jms Q100000 K9 of JEOL Ltd. was used for GC/MS.

(3) Hydrolysis resistance

A 4 mm-thick molded piece for ISO measurement was formed from the resin composition by using an injection molding machine (IS-150EN of Toshiba Machine Co., Ltd.) at a cylinder temperature of 230° C. and a mold temperature of 120° C. Then, this molded piece was subjected to a moist heat treatment at 80° C. and 95% RH for 200 hours. A tensile test was conducted in accordance with 150527-1 and ISO527-2 to calculate a retention [(tensile maximum stress after moist heat treatment/tensile maximum stress before moist heat treatment)×100] from tensile maximum stress before the moist heat treatment and tensile maximum stress after the moist heat treatment.

(4) Long-term heat resistance

A 4 mm-thick molded piece for ISO measurement was formed from the resin composition by using an injection molding machine (IS-150EN of Toshiba Machine Co., Ltd.) at a cylinder temperature of 230° C., a mold temperature of 120° C. and a molding cycle of 70 seconds. Then, this molded piece was dry heated at 120° C. with a hot air circulation drier for 3,000 hours. A tensile test was conducted in accordance with ISO527-1 and ISO527-2 to calculate a retention [(tensile maximum stress after moist heat treatment/tensile maximum stress before moist heat treatment)×100] from tensile maximum stress before the moist heat treatment and tensile maximum stress after the moist heat treatment.

(5) Notched impact value

A 4 mm-thick ISO standard test specimen was formed from the resin composition by using an injection molding machine (IS-150EN of Toshiba Machine Co., Ltd.) at a cylinder temperature of 230° C., a mold temperature of 120° C. and a molding cycle of 70 sec. The notched impact value of the test specimen was measured in accordance with ISO standards after it was left in a 23° C.-50% RH environment for 24 hours.

(6) Flame retardancy

The flame retardancy of a test specimen having a thickness of 1.5 mm was evaluated by the method (UL94) specified by Underwriters Laboratories Inc. of the U.S.

(7) Deflection temperature under load

A 4 mm-thick ISO standard test specimen was formed from the resin composition by using an injection molding machine (IS-150EN of Toshiba Machine Co., Ltd.) at a cylinder temperature of 230° C., a mold temperature of 120° C. and a molding cycle of 70 sec. The deflection temperature under load of the test specimen was measured under a load of 0.45 MPa in accordance with 15075-1 and 15075-2 after it was left in a 23° C.-50% RH environment for 24 hours.

(8) Tensile distortion at break

A 4 mm-thick molded piece for ISO measurement was formed from the resin composition by using an injection molding machine (IS-150EN of Toshiba Machine Co., Ltd.) at a cylinder temperature of 230° C., a mold temperature of 120° C. and a molding cycle of 70 sec. A tensile test was conducted at a tensile speed of 5 mm/min in accordance with ISO 527-1 and 150527-2 to measure the amount of distortion when the test piece was broken.

(9) Melt heat stability

After continuous molding, the molding machine was suspended temporarily to retain the resin in the cylinder. The appearance of a molded piece obtained by molding after 10 minutes of residence was checked visually. The melt heat stability was judged based on the following criteria.

○: no silver streak is seen in molded article

X: a silver streak is seen in molded article.

<Component A-α>

The components A-α-1, A-α-2 and A-α-3 prepared in Production Examples 1-1 to 1-3 were used as the component A-α.

<Component A-β-1>

A-β-1-1: Juranex 300 FP of Wintec Polymer Co., Ltd. [polybutylene terephthalate resin]

A-β-1-2: TR-4550BH of Teijin Limited [polyethylene terephthalate]

<Component A-β-2>

A-β-2-1: Novatec FA3DA of Mitsui Chemical Co., Ltd., MVR [240° C., 2.16 kg]=12 $cm^3$/10 min [polypropylene resin]

<Component A-β-3>
A-β-3-1: linear aromatic polycarbonate powder having a viscosity average molecular weight of 25,110 (Panlite L-1250WQ (trade name) of Teijin Chemicals Ltd.)<component B>
B-1: cyclic carbodiimide (CC1) produced in Production Example 2-1
B-2: cyclic carbodiimide (CC2) produced in Production Example 2-2
<Component B'>
B'-1: Carbodilite LA-1 of Nisshinbo Industries, Ltd. [aliphatic polycarbodiimide]
B'-2: stabaxol-P of Line Chemie Japan Co., Ltd. [aromatic polycarbodiimide]
<Component C>
C-1: Irganox 1076 of Ciba Specialty Chemicals Co., Ltd. [n-octadecyl-3-(3',5'-di-tert-butyl-4'-hydroxyphenyl) propionate]
C-2: PEP-24G of ADEKA Corporation [bis(2,4-di-tert-butylphenyl)pentaerythritol diphosphite]
C-3: Sandstab P-EPQ of Clariant Japan Co., Ltd. [tetrakis (2,4-di-tert-butylphenyl) [1,1-biphenyl]-4,4'-diylbis phosphonite]
C-4: Adecastab AO-412S of ADEKA Corporation [3-lauryl thiopropionate]
<Component D>
D-1: ADR-4368CS of BASF Japan Co., Ltd. [epoxy group-containing acrylic styrene copolymer]
D-2: BOX-210 of Takemoto Yushi Co., Ltd. [2,2-(1,3-phenylene)bis-2-oxazoline]
<Component E>
E-1: DHT-4A-2 of Kyowa Chemical Industry, Co., Ltd. [baked hydrotalcite]
<Component F>
F-1: Metabrene S-2001 of Mitsubishi Rayon Co., Ltd. [silicone-based core-shell rubber]
F-2: Paraloid BPM500 of Rohm and Haase Co., Ltd. [acrylic core-shell rubber]
F-3: AT-05 of Nippon A and L Co., Ltd. [acrylonitrile-butadiene-styrene copolymer]
F-4: Bond Fast 7M of Sumitomo Chemical Co., Ltd. [polyethylene-glycidyl methacrylate copolymer]
F-5: TPAE-32 of Fuji Kasei Kogyo Co., Ltd. [polyether ester amide elastomer]
<Component G>
G-1-1: PX-200 of Daihachi Chemical Industry Co., Ltd. [resorcinol bis(di-2,6-xylyl phosphate)]
G-1-2: Exolit OP1240 of Clariant Japan Co., Ltd. [aluminum diethyl phosphinate]
G-1-3: APA-100 of Taihei Kagaku Sangyo Co., Ltd. [aluminum phosphite]
G-2-1: MELAPUR200 of Ciba Specialty Chemicals Co., Ltd. [melamine polyphosphate]
G-2-2: MC610 of Nissan Chemical Industries, Ltd. {melamine isocyanurate}
G-3: EP-1 of Kamishima Kagaku Co., Ltd. [magnesium hydroxide]
G-4: PATOX-K of Nippon Seiko Co., Ltd. [antimony trioxide]
G-5: EP-100 of Dainippon Ink and Chemicals, Inc. {brominated epoxy resin}
<Component H>
H-1: 3PE-937S of Nitto Boseki Co., Ltd. (chopped strand having an average diameter of 13 μm and a cut length of 3 mm)
<Component I>
I-1: SA-120 of SABIC Inovative Plastics Japan Co., Ltd. [polyphenylene ether oligomer]
I-2: FA-500C of Daikin Industries, Ltd. [tetrafluoroethylene]

Example 1-1

The poly-L-lactic acid (A-α-1) produced in Production Example 1 was used as polylactic acid and premixed with components shown in Table 1-2 uniformly by dry blending, and the premixture was supplied from a first feed port and melt extruded into a pellet. The first feed port is a feed port at the base. Melt extrusion was carried out by using a 30 mmφ vented double-screw extruder having a side screw [TEX30XSST of The Japan Steel Works, Ltd.]. The extrusion temperatures of C1/C2 to C5/C6/C7 to C11/D were 10° C./240° C./230° C./220° C./220° C., respectively, the revolution of the main screw was 150 rpm, the revolution of the side screw was 50 rpm, the delivery rate was 20 kg/h, and the vent vacuum degree was 3 kPa.

The obtained pellet was dried at 100° C. for 5 hours by means of a hot air circulating drier and molded by means of an injection molding machine (IS-150EN of Toshiba Machine Co., Ltd.) to make evaluations. The results are shown in Table 1-2.

Example 1-2

A pellet was obtained in the same manner as in Example 1-1 except that the poly-D-lactic acid (A-α-2) produced in Production Example 1-2 was used as the polylactic acid and evaluated. The results are shown in Table 1-2.

Examples 1-3 to 1-17 and Comparative Examples 1-1 to 1-9

Pellets were obtained in the same manner as in Example 1-1 except that the stereocomplex polylactic acid (A-α-3) produced in Production Example 1-3 was used as the polylactic acid and evaluated. As for the composition comprising the component H-1, components excluding the component H-1 were premixed together uniformly by dry blending, and the premixture was supplied from the first feed port and the component H-1 was supplied from a second feed port. The second feed port is provided in a side screw. The results are shown in Tables 1-2 to 1-4. The word "unmeasurable" for hydrolysis resistance in these tables means that a molded article lost its original shape after a moist heat treatment and a tensile test could not be made.

TABLE 1-2

| | | Unit | Ex. 1-1 | Ex. 1-2 | Ex. 1-3 | Ex. 1-4 | Ex. 1-5 | C. Ex. 1-1 | C. Ex. 1-2 | C. Ex. 1-3 | C. Ex. 1-4 |
|---|---|---|---|---|---|---|---|---|---|---|---|
| Component A | A-α-1 | pbw | 100 | | | | | | | | |
| | A-α-2 | | | 100 | | | | | | | |
| | A-α-3 | | | | 100 | 100 | 100 | 100 | 100 | 100 | 100 |
| Component B | B-1 | | | | 1 | | | | | | |
| | B-2 | | 1 | 1 | | 1 | 8 | 0.1 | 1 | 15 | 1 |

TABLE 1-2-continued

|  |  | Unit | Ex. 1-1 | Ex. 1-2 | Ex. 1-3 | Ex. 1-4 | Ex. 1-5 | C. Ex. 1-1 | C. Ex. 1-2 | C. Ex. 1-3 | C. Ex. 1-4 |
|---|---|---|---|---|---|---|---|---|---|---|---|
| Component B' | B'-1 |  |  |  |  |  |  |  |  |  |  |
|  | B'-2 |  |  |  |  |  |  |  |  |  |  |
| Component C | C-1 |  | 0.1 | 0.1 | 0.1 | 0.1 | 0.1 | 0.1 |  | 0.1 | 3 |
|  | C-2 |  |  |  |  |  |  |  |  |  |  |
|  | C-3 |  |  |  |  |  |  |  |  |  |  |
|  | C-4 |  |  |  |  |  |  |  |  |  |  |
| Component D | D-1 |  |  |  |  |  |  |  |  |  |  |
|  | D-2 |  |  |  |  |  |  |  |  |  |  |
| Component E | E-1 |  |  |  |  |  |  |  |  |  |  |
| Component H | H-1 |  |  |  |  |  |  |  |  |  |  |
| Work environment |  | — | ○ | ○ | ○ | ○ | ○ | ○ | ○ | ○ | ○ |
| Quantitative determination of isocyanate gas |  | ppm | Not detected | Not detected | Not detected | Not detected | Not detected | Not detected | Not detected | Not detected | Not detected |
| Melt heat stability |  | — | ○ | ○ | ○ | ○ | ○ | ○ | ○ | ○ | ○ |
| Hydrolysis resistance |  | % | 78 | 76 | 78 | 74 | 65 | Unmeasurable | 38 | 31 | 42 |

Ex.: Example,
C. Ex.: Comparative Example,
pbw: Parts by weight

TABLE 1-3

|  |  | Unit | Ex. 1-6 | Ex. 1-7 | Ex. 1-8 | Ex. 1-9 | Ex. 1-10 | Ex. 1-11 | Ex. 1-12 | C. Ex. 1-5 | C. Ex. 1-6 |
|---|---|---|---|---|---|---|---|---|---|---|---|
| Component A | A-α-1 | pbw |  |  |  |  |  |  |  |  |  |
|  | A-α-2 |  |  |  |  |  |  |  |  |  |  |
|  | A-α-3 |  | 100 | 100 | 100 | 100 | 100 | 100 | 100 | 100 | 100 |
| Component B | B-1 |  |  |  |  |  |  |  |  |  |  |
|  | B-2 |  | 1 | 1 | 1 | 1 | 1 | 1 | 1 |  |  |
| Component B' | B'-1 |  |  |  |  |  |  |  |  | 1 |  |
|  | B'-2 |  |  |  |  |  |  |  |  |  | 1 |
| Component C | C-1 |  | 1.5 |  |  |  | 0.1 | 0.1 | 0.1 | 0.1 | 0.1 |
|  | C-2 |  |  | 0.1 |  |  | 0.1 |  |  |  |  |
|  | C-3 |  |  |  | 0.1 |  |  | 0.1 |  |  |  |
|  | C-4 |  |  |  |  | 0.1 |  |  | 0.1 |  |  |
| Component D | D-1 |  |  |  |  |  |  |  |  |  |  |
|  | D-2 |  |  |  |  |  |  |  |  |  |  |
| Component E | E-1 |  |  |  |  |  |  |  |  |  |  |
| Component H | H-1 |  |  |  |  |  |  |  |  |  |  |
| Work environment |  | — | ○ | ○ | ○ | ○ | ○ | ○ | ○ | x | x |
| Quantitative determination of isocyanate gas |  | ppm | not detected | not detected | not detected | not detected | not detected | not detected | not detected | 200 | 260 |
| Melt heat stability |  | — | ○ | ○ | ○ | ○ | ○ | ○ | ○ | x | x |
| Hydrolysis resistance |  | % | 71 | 71 | 70 | 70 | 84 | 82 | 82 | 23 | 71 |

Ex.: Example,
C. Ex.: Comparative Example,
pbw: Parts by weight

TABLE 1-4

|  |  | Unit | Ex. 1-13 | Ex. 1-14 | Ex. 1-15 | Ex. 1-16 | Ex. 1-17 | C. Ex. 1-7 | C. Ex. 1-8 | C. Ex. 1-9 |
|---|---|---|---|---|---|---|---|---|---|---|
| Component A | A-α-1 | pbw |  |  |  |  |  |  |  |  |
|  | A-α-2 |  |  |  |  |  |  |  |  |  |
|  | A-α-3 |  | 100 | 100 | 100 | 100 | 100 | 100 | 100 | 100 |
| Component B | B-1 |  |  |  |  |  |  |  |  |  |
|  | B-2 |  | 1 | 1 | 1 | 1 | 1 |  |  | 1 |
| Component B' | B'-1 |  |  |  |  |  |  |  |  |  |
|  | B'-2 |  |  |  |  |  |  |  |  |  |
| Component C | C-1 |  | 0.1 | 0.1 | 0.1 | 0.1 | 0.1 | 0.1 | 0.1 |  |
|  | C-2 |  | 0.1 | 0.1 | 0.1 | 0.1 |  | 0.1 |  |  |
|  | C-3 |  |  |  |  |  |  |  |  |  |
|  | C-4 |  |  |  |  |  |  |  |  |  |
| Component D | D-1 |  | 0.5 |  |  | 0.5 |  | 0.5 |  |  |
|  | D-2 |  |  | 0.5 |  |  |  |  |  |  |

TABLE 1-4-continued

|  | Unit | Ex. 1-13 | Ex. 1-14 | Ex. 1-15 | Ex. 1-16 | Ex. 1-17 | C. Ex. 1-7 | C. Ex. 1-8 | C. Ex. 1-9 |
|---|---|---|---|---|---|---|---|---|---|
| Component E E-1 |  |  |  | 0.1 | 0.1 |  |  | 0.1 |  |
| Component H H-1 |  |  |  |  |  | 30 |  | 30 | 30 |
| Work environment | — | ○ | ○ | ○ | ○ | ○ | ○ | ○ | ○ |
| Quantitative determination of isocyanate gas | ppm | not detected | not detected | not detected | not detected | not detected | not detected | not detected | not detected |
| Melt heat stability | — | ○ | ○ | ○ | ○ | ○ | ○ | ○ | ○ |
| Hydrolysis resistance | % | 89 | 87 | 92 | 99 | 82 | Unmeasurable | Unmeasurable | 44 |

Example 1-1 to 1-17 comprising both a cyclic carbodiimide and an antioxidant were materials which ensured a good work environment, produced no isocyanate gas and had excellent hydrolysis resistance. On the other hand, Comparative Examples 1-1 to 1-2 and Comparative Examples 1-8 to 1-9 which comprised one of them were greatly inferior in hydrolysis resistance. Comparative Examples 1-3 and 1-4 in which the amount of the cyclic carbodiimide and the amount of the antioxidant were too large had poor hydrolysis resistance. In Comparative Examples 1-5 and 1-6 comprising a carbodiimide which is not a cyclic carbodiimide, the work environment became bad due to an irritating smell, the production of an isocyanate gas was observed by GC/MS, and melt heat stability was low. Comparative Example 1-7, which contained only an antioxidant comprising a carbodiimide (component C) and an end-sealing agent (component D), was greatly inferior in hydrolysis resistance.

When the content of the cyclic carbodiimide component B-2 in the resin composition was checked by NMR in Examples 1-3 and 1-5 and Comparative Example 1-1, it was 0.6 part by weight in Example 1-3, 7.5 parts by weight in Example 1-5 and not detected (0 part by weight) in Comparative Example 1-1 based on 100 parts by weight of the resin component (component A).

Example 2-1

The poly-L-lactic acid (A-α-1) produced in Production Example 1-1 was used as the polylactic acid and premixed with components shown in Table 2-1 uniformly by dry blending, and the premixture was supplied from a first feed port and melt extruded into a pellet. The first feed port is a feed port at the base. Melt extrusion was carried out by using a 30 mmφ vented double-screw extruder having a side screw [TEX30XSST of The Japan Steel Works, Ltd.]. The extrusion temperatures of C1/C2 to C5/C6/C7 to C11/D were 10° C./240° C./230° C./220° C./220° C., respectively, the revolution of the main screw was 150 rpm, the revolution of the side screw was 50 rpm, the delivery rate was 20 kg/h, and the vent vacuum degree was 3 kPa.

The obtained pellet was dried at 100° C. for 5 hours by means of a hot air circulating drier and molded by means of an injection molding machine (IS-150EN of Toshiba Machine Co., Ltd.) to make evaluations. The results are shown in Table 2-2.

Example 2-2

A pellet was obtained in the same manner as in Example 1 except that the poly-D-lactic acid (A-α-2) produced in Production Example 1-2 was used as the polylactic acid and evaluated. The results are shown in Table 2-2.

Examples 2-3 to 2-37

Pellets were obtained in the same manner as in Example 2-1 except that the stereocomplex polylactic acid (A-α-3) produced in Production Example 1-3 was used as the polylactic acid and evaluated. In the composition comprising the component I-1, components excluding the component I-1 were premixed together uniformly by dry blending, and the premixture was supplied from the first feed port and the component I-1 was supplied from a second feed port. The second feed port is provided in a side screw. The results are shown in Tables 2-2 to 2-5. The word "collapse" for hydrolysis resistance in these tables means that a molded article lost its original shape after a moist heat treatment and a tensile test could not be made.

TABLE 2-1

|  |  | Unit | Ex. 2-1 | Ex. 2-2 | Ex. 2-3 | Ex. 2-4 | Ex. 2-5 | Ex. 2-6 | Ex. 2-7 | Ex. 2-8 |
|---|---|---|---|---|---|---|---|---|---|---|
| Component A | A-α-1 | pbw | 75 |  |  |  |  |  |  |  |
|  | A-α-2 |  |  | 75 |  |  |  |  |  |  |
|  | A-α-3 |  |  |  | 75 | 75 | 75 | 75 | 75 | 75 |
|  | A-β-1-1 |  | 25 | 25 | 25 |  | 25 |  | 25 |  |
|  | A-β-1-2 |  |  |  |  | 25 |  | 25 |  | 25 |
| Component B | B-2 |  | 1 | 1 | 1 | 1 | 10 | 10 | 0.05 | 0.05 |
| Component B' | B'-1 |  |  |  |  |  |  |  |  |  |
|  | B'-2 |  |  |  |  |  |  |  |  |  |
| Component C | C-1 |  | 0.1 | 0.1 | 0.1 | 0.1 | 0.1 | 0.1 | 0.1 | 0.1 |
|  | C-2 |  |  |  |  |  |  |  |  |  |
|  | C-3 |  |  |  |  |  |  |  |  |  |
|  | C-4 |  |  |  |  |  |  |  |  |  |

TABLE 2-1-continued

|  |  | Unit | Ex. 2-1 | Ex. 2-2 | Ex. 2-3 | Ex. 2-4 | Ex. 2-5 | Ex. 2-6 | Ex. 2-7 | Ex. 2-8 |
|---|---|---|---|---|---|---|---|---|---|---|
| Work environment | | — | ○ | ○ | ○ | ○ | ○ | ○ | ○ | ○ |
| Quantitative determination of isocyanate gas | | ppm | Not detected | Not detected | Not detected | Not detected | Not detected | Not detected | Not detected | Not detected |
| Hydrolysis resistance | | % | 84 | 83 | 91 | 92 | 84 | 83 | 86 | 83 |
| Long-term heat resistance | | % | 53 | 55 | 71 | 83 | 70 | 69 | 71 | 71 |
| Notched impact value | | kJ/m² | 3 | 3 | 3 | 3 | 3 | 3 | 3 | 3 |

Ex.: Example

TABLE 2-2

|  |  | Unit | Ex. 2-9 | Ex. 2-10 | Ex. 2-11 | Ex. 2-12 | Ex. 2-13 |
|---|---|---|---|---|---|---|---|
| Component A | A-α-1 | pbw | | | | | |
|  | A-α-2 | | | | | | |
|  | A-α-3 | | 75 | 75 | 75 | 75 | 75 |
|  | A-β-1-1 | | 25 | 25 | 25 | 25 | 25 |
|  | A-β-1-2 | | | | | | |
| Component B | B-2 | | 1 | 1 | 1 | 1 | 1 |
| Component B' | B'-1 | | | | | | |
|  | B'-2 | | | | | | |
| Component C | C-1 | | 2 | 0.005 | | | |
|  | C-2 | | | | 0.1 | | |
|  | C-3 | | | | | 0.1 | |
|  | C-4 | | | | | | 0.1 |
| Work environment | | — | ○ | ○ | ○ | ○ | ○ |
| Quantitative determination of isocyanate gas | | ppm | Not detected | Not detected | Not detected | Not detected | Not detected |
| Hydrolysis resistance | | % | 70 | 71 | 88 | 89 | 87 |
| Long-term heat resistance | | % | 71 | 56 | 68 | 66 | 67 |
| Notched impact value | | kJ/m² | 2 | 3 | 3 | 3 | 3 |

|  |  | Unit | Ex. 2-14 | Ex. 2-15 | Ex. 2-16 | Ex. 2-17 | Ex. 2-18 |
|---|---|---|---|---|---|---|---|
| Component A | A-α-1 | pbw | | | | | |
|  | A-α-2 | | | | | | |
|  | A-α-3 | | 75 | 75 | 75 | 50 | 25 |
|  | A-β-1-1 | | 25 | 25 | 25 | 50 | 75 |
|  | A-β-1-2 | | | | | | |
| Component B | B-2 | | 1 | 1 | 1 | 1 | 1 |
| Component B' | B'-1 | | | | | | |
|  | B'-2 | | | | | | |
| Component C | C-1 | | 0.1 | 0.1 | 0.1 | 0.1 | 0.1 |
|  | C-2 | | 0.1 | | | | |
|  | C-3 | | | 0.1 | | | |
|  | C-4 | | | | 0.1 | | |
| Work environment | | — | ○ | ○ | ○ | ○ | ○ |
| Quantitative determination of isocyanate gas | | ppm | Not detected | Not detected | Not detected | Not detected | Not detected |
| Hydrolysis resistance | | % | 95 | 94 | 95 | 96 | 100 |
| Long-term heat resistance | | % | 73 | 72 | 74 | 81 | 90 |
| Notched impact value | | kJ/m² | 3 | 3 | 3 | 3 | 4 |

Ex.: Example

TABLE 2-3

|  |  | Unit | Ex. 2-19 | Ex. 2-20 | Ex. 2-21 | Ex. 2-22 | Ex. 2-23 |
|---|---|---|---|---|---|---|---|
| Component A | A-α-1 | pbw | | | | | |
|  | A-α-2 | | | | | | |
|  | A-α-3 | | 75 | 75 | 75 | 75 | 75 |
|  | A-β-1-1 | | 25 | 25 | 25 | 25 | 25 |
|  | A-β-1-2 | | | | | | |

TABLE 2-3-continued

|   |   | Ex. (cont.) | | | | |
|---|---|---|---|---|---|---|
| Component B | B-2 | 1 | 1 | 1 | 1 | 1 |
| Component B' | B'-1 | | | | | |
|  | B'-2 | | | | | |
| Component C | C-1 | 0.1 | 0.1 | 0.1 | 0.1 | 0.1 |
|  | C-2 | | | | | |
|  | C-3 | | | | | |
|  | C-4 | | | | | |
| Component D | D-1 | 1 | | 1 | 1 | 1 |
|  | D-2 | | 1 | | | |
| Component E | E-1 | | | 0.1 | | |
| Component F | F-1 | | | | 5 | |
|  | F-2 | | | | | 5 |
|  | F-3 | | | | | |
|  | F-4 | | | | | |
|  | F-5 | | | | | |
| Work environment | — | ○ | ○ | ○ | ○ | ○ |
| Quantitative determination of isocyanate gas | ppm | Not detected | Not detected | Not detected | Not detected | Not detected |
| Hydrolysis resistance | % | 95 | 95 | 100 | 100 | 100 |
| Long-term heat resistance | % | 73 | 71 | 72 | 62 | 59 |
| Notched impact value | kJ/m² | 3 | 3 | 3 | 7 | 7 |

|   |   | Unit | Ex. 2-24 | Ex. 2-25 | Ex. 2-26 | Ex. 2-27 |
|---|---|---|---|---|---|---|
| Component A | A-α-1 | pbw | | | | |
|  | A-α-2 | | | | | |
|  | A-α-3 | | 75 | 75 | 75 | 75 |
|  | A-β-1-1 | | 25 | 25 | 25 | 25 |
|  | A-β-1-2 | | | | | |
| Component B | B-2 | | 1 | 1 | 1 | 1 |
| Component B' | B'-1 | | | | | |
|  | B'-2 | | | | | |
| Component C | C-1 | | 0.1 | 0.1 | 0.1 | 0.1 |
|  | C-2 | | | | | |
|  | C-3 | | | | | |
|  | C-4 | | | | | |
| Component D | D-1 | | 1 | 1 | 1 | 1 |
|  | D-2 | | | | | |
| Component E | E-1 | | | | | |
| Component F | F-1 | | | | | |
|  | F-2 | | | | | |
|  | F-3 | | 5 | | | |
|  | F-4 | | | 5 | | 2 |
|  | F-5 | | | | 5 | 5 |
| Work environment | — | ○ | ○ | ○ | ○ | |
| Quantitative determination of isocyanate gas | ppm | Not detected | Not detected | Not detected | Not detected | |
| Hydrolysis resistance | % | 100 | 100 | 100 | 100 | |
| Long-term heat resistance | % | 65 | 69 | 70 | 70 | |
| Notched impact value | kJ/m² | 8 | 7 | 7 | 9 | |

Ex.: Example

TABLE 2-4

|   |   | Unit | Ex. 2-28 | Ex. 2-29 | Ex. 2-30 | Ex. 2-31 | Ex. 2-32 |
|---|---|---|---|---|---|---|---|
| Component A | A-α-1 | pbw | | | | | |
|  | A-α-2 | | | | | | |
|  | A-α-3 | | 75 | 75 | 75 | 75 | 75 |
|  | A-β-1-1 | | 25 | 25 | 25 | 25 | 25 |
|  | A-β-1-2 | | | | | | |
| Component B | B-2 | | 1 | 1 | 1 | 1 | 1 |
| Component B' | B'-1 | | | | | | |
|  | B'-2 | | | | | | |

TABLE 2-4-continued

| Component | | | | | | |
|---|---|---|---|---|---|---|
| Component C | C-1 | 0.1 | 0.1 | 0.1 | 0.1 | 0.1 |
| | C-2 | | | | | |
| | C-3 | | | | | |
| | C-4 | | | | | |
| Component D | D-1 | 1 | 1 | 1 | 1 | 1 |
| | D-2 | | | | | |
| Component E | E-1 | 0.1 | 0.1 | 0.1 | 0.1 | 0.1 |
| Component F | F-1 | | 5 | 5 | 5 | 5 |
| | F-2 | | | | | |
| | F-3 | | | | | |
| | F-4 | | | | | |
| | F-5 | | | | | |

| | | Unit | Ex. 2-33 | Ex. 2-34 | Ex. 2-35 | Ex. 2-36 | Ex. 2-37 |
|---|---|---|---|---|---|---|---|
| Component A | A-α-1 | pbw | | | | | |
| | A-α-2 | | | | | | |
| | A-α-3 | | 75 | 75 | 75 | 75 | 75 |
| | A-β-1-1 | | 25 | 25 | 25 | 25 | 25 |
| | A-β-1-2 | | | | | | |
| Component B | B-2 | | 1 | 1 | 1 | 1 | 1 |
| Component B' | B'-1 | | | | | | |
| | B'-2 | | | | | | |
| Component C | C-1 | | 0.1 | 0.1 | 0.1 | 0.1 | 0.1 |
| | C-2 | | | | | | |
| | C-3 | | | | | | |
| | C-4 | | | | | | |
| Component D | D-1 | | 1 | 1 | 1 | 1 | 1 |
| | D-2 | | | | | | |
| Component E | E-1 | | 0.1 | 0.1 | 0.1 | 0.1 | 0.1 |
| Component F | F-1 | | 5 | 5 | 5 | 5 | |
| | F-2 | | | | | | |
| | F-3 | | | | | | |
| | F-4 | | | | | | |
| | F-5 | | | | | | |

| | | Unit | Ex. 2-28 | Ex. 2-29 | Ex. 2-30 | Ex. 2-31 | Ex. 2-32 |
|---|---|---|---|---|---|---|---|
| Component G | G-1-1 | pbw | 10 | 10 | | | |
| | G-1-2 | | | | 10 | | 10 |
| | G-1-3 | | | | | 10 | |
| | G-2-1 | | | | | | 5 |
| | G-2-2 | | | | | | |
| | G-3 | | | | | | |
| | G-4 | | | | | | |
| | G-5 | | | | | | |
| Component H | H-1 | | | | | | |
| Component I | I-1 | | | | | | 5 |
| | I-2 | | | | | | 0.5 |
| Work environment | | — | ○ | ○ | ○ | ○ | ○ |
| Quantitative determination of isocyanate gas | | ppm | Not detected | Not detected | Not detected | Not detected | Not detected |
| Hydrolysis resistance | | % | 98 | 99 | 89 | 97 | 87 |
| Long-term heat resistance | | % | 68 | 62 | 61 | 67 | 51 |
| Notched impact value | | kJ/m² | 3 | 6 | 5 | 5 | 5 |
| Flame retardant | | — | V-2 | V-2 | V-2 | V-2 | V-0 |

| | | Unit | Ex. 2-33 | Ex. 2-34 | Ex. 2-35 | Ex. 2-36 | Ex. 2-37 |
|---|---|---|---|---|---|---|---|
| Component G | G-1-1 | pbw | | | | | |
| | G-1-2 | | | | | | |
| | G-1-3 | | 10 | 10 | | | |
| | G-2-1 | | 5 | | | | |
| | G-2-2 | | | 5 | | | |
| | G-3 | | | | 40 | | |
| | G-4 | | | | | 3 | 3 |
| | G-5 | | | | | 10 | 10 |
| Component H | H-1 | | | | | | 40 |
| Component I | I-1 | | 5 | 5 | 5 | | |
| | I-2 | | 0.5 | 0.5 | | 0.5 | 0.5 |
| Work environment | | — | ○ | ○ | ○ | ○ | ○ |

TABLE 2-4-continued

| | | | | | | |
|---|---|---|---|---|---|---|
| Quantitative determination of isocyanate gas | ppm | Not detected | Not detected | Not detected | Not detected | Not detected |
| Hydrolysis resistance | % | 94 | 89 | 86 | 98 | 98 |
| Long-term heat resistance | % | 52 | 53 | 52 | 72 | 76 |
| Notched impact value | kJ/m² | 5 | 5 | 4 | 7 | 10 |
| Flame retardant | — | V-0 | V-0 | V-0 | V-0 | V-0 |

Exx.: Example
Ex.: Example

Examples 2-1 to 2-18 were materials which ensured a good work environment, produced no isocyanate gas and were excellent in hydrolysis resistance, long-term heat resistance and notched impact value. In Examples 2-19 and 2-20 in which the component D was further added, the further improvement of hydrolysis resistance was seen. In Example 2-21 in which the component E-1 was further added, the effect of improving hydrolysis resistance was greater than that of Example 2-19. Examples 2-22 to 2-27 were materials which saw the improvement of the notched impact value as they contained the component F, ensured a good work environment, produced no isocyanate gas and were excellent in hydrolysis resistance and long-term heat resistance. Examples 2-28 to 2-37 were materials which further provided flame retardancy, ensured a good work environment, produced no isocyanate gas and were excellent in hydrolysis resistance, long-term heat resistance and notched impact value.

Example 3-1

The poly-L-lactic acid (A-α-1) produced in Production Example 1-1 was used as the polylactic acid and premixed with components shown in Table 3-2 uniformly by dry blending, and the premixture was supplied from a first feed port and melt extruded into a pellet. The first feed port is a feed port at the base. Melt extrusion was carried out by using a 30 mmφ vented double-screw extruder having a side screw [TEX30XSST of The Japan Steel Works, Ltd.]. The extrusion temperatures of C1/C2 to C5/C6/C7 to C11/D were 10° C./240° C./230° C./220° C./220° C., respectively, the revolution of the main screw was 150 rpm, the revolution of the side screw was 50 rpm, the delivery rate was 20 kg/h, and the vent vacuum degree was 3 kPa.

The obtained pellet was dried at 100° C. for 5 hours by means of a hot air circulating drier and molded by means of an injection molding machine (IS-150EN of Toshiba Machine Co., Ltd.) to make evaluations. The results are shown in Table 3-2.

Example 3-2

A pellet was obtained in the same manner as in Example 3-1 except that the poly-D-lactic acid (A-α-2) produced in Production Example 1-2 was used as the polylactic acid and evaluated. The results are shown in Table 3-2.

Examples 3-3 to 3-34

Pellets were obtained in the same manner as in Example 3-1 except that the stereocomplex polylactic acid (A-α-3) produced in Production Example 1-3 was used as the polylactic acid and evaluated. In the composition comprising the component I-1, components excluding the component I-1 were premixed together uniformly by dry blending, and the premixture was supplied from the first feed port and the component I-1 was supplied from a second feed port. The second feed port is provided in a side screw. The results are shown in Tables 3-2 to 3-5. The word "collapse" for hydrolysis resistance in these tables means that a molded article lost its original shape after a moist heat treatment and a tensile test could not be made.

TABLE 3-1

| | | Unit | Ex. 3-1 | Ex. 3-2 | Ex. 3-3 | Ex. 3-4 | Ex. 3-5 |
|---|---|---|---|---|---|---|---|
| Component A | A-α-1 | pbw | 75 | | | | |
| | A-α-2 | | | 75 | | | |
| | A-α-3 | | | | 75 | 75 | 75 |
| | A-β-2-1 | | 25 | 25 | 25 | 25 | 25 |
| Component B | B-2 | | 1 | 1 | 1 | 10 | 0.05 |
| Component B' | B'-1 | | | | | | |
| | B'-2 | | | | | | |
| Component C | C-1 | | 0.1 | 0.1 | 0.1 | 0.1 | 0.1 |
| | C-2 | | | | | | |
| | C-3 | | | | | | |
| | C-4 | | | | | | |
| Work environment | | — | ○ | ○ | ○ | ○ | ○ |
| Quantitative determination of isocyanate gas | | ppm | Not detected | Not detected | Not detected | Not detected | Not detected |
| Deflection temperature under load | | ° C. | 97 | 95 | 125 | 121 | 124 |
| Tensile distortion at break | | % | 10 | 10 | 9 | 8 | 9 |
| Notched impact value | | kJ/m² | 4 | 4 | 4 | 4 | 4 |
| Hydrolysis resistance | | % | 82 | 81 | 88 | 78 | 75 |

Ex.: Example

TABLE 3-2

|  |  | Unit | Ex. 3-6 | Ex. 3-7 | Ex. 3-8 | Ex. 3-9 | Ex. 3-10 |
|---|---|---|---|---|---|---|---|
| Component A | A-α-1 | pbw |  |  |  |  |  |
|  | A-α-2 |  |  |  |  |  |  |
|  | A-α-3 |  | 75 | 75 | 75 | 75 | 75 |
|  | A-β-2-1 |  | 25 | 25 | 25 | 25 | 25 |
| Component B | B-2 |  | 1 | 1 | 1 | 1 | 1 |
| Component B' | B'-1 |  |  |  |  |  |  |
|  | B'-2 |  |  |  |  |  |  |
| Component C | C-1 |  | 2 | 0.005 |  |  |  |
|  | C-2 |  |  |  | 0.1 |  |  |
|  | C-3 |  |  |  |  | 0.1 |  |
|  | C-4 |  |  |  |  |  | 0.1 |
| Work environment |  | — | ○ | ○ | ○ | ○ | ○ |
| Quantitative determination of isocyanate gas | | ppm | Not detected | Not detected | Not detected | Not detected | Not detected |
| Deflection temperature under load | | °C. | 119 | 120 | 121 | 123 | 121 |
| Tensile distortion at break | | % | 10 | 9 | 10 | 10 | 11 |
| Notched impact value | | kJ/m$^2$ | 4 | 4 | 4 | 4 | 4 |
| Hydrolysis resistance | | % | 78 | 76 | 85 | 86 | 83 |

|  |  | Unit | Ex. 3-11 | Ex. 3-12 | Ex. 3-13 | Ex. 3-14 | Ex. 3-15 |
|---|---|---|---|---|---|---|---|
| Component A | A-α-1 | pbw |  |  |  |  |  |
|  | A-α-2 |  |  |  |  |  |  |
|  | A-α-3 |  | 75 | 75 | 75 | 50 | 25 |
|  | A-β-2-1 |  | 25 | 25 | 25 | 50 | 75 |
| Component B | B-2 |  | 1 | 1 | 1 | 1 | 1 |
| Component B' | B'-1 |  |  |  |  |  |  |
|  | B'-2 |  |  |  |  |  |  |
| Component C | C-1 |  | 0.1 | 0.1 | 0.1 | 0.1 | 0.1 |
|  | C-2 |  | 0.1 |  |  |  |  |
|  | C-3 |  |  | 0.1 |  |  |  |
|  | C-4 |  |  |  | 0.1 |  |  |
| Work environment |  | — | ○ | ○ | ○ | ○ | ○ |
| Quantitative determination of isocyanate gas | | ppm | Not detected | Not detected | Not detected | Not detected | Not detected |
| Deflection temperature under load | | °C. | 124 | 123 | 122 | 119 | 121 |
| Tensile distortion at break | | % | 10 | 10 | 10 | 40 | 82 |
| Notched impact value | | kJ/m$^2$ | 4 | 4 | 4 | 5 | 6 |
| Hydrolysis resistance | | % | 92 | 91 | 93 | 97 | 98 |

Ex: Example

TABLE 3-3

|  |  | Unit | Ex. 3-16 | Ex. 3-17 | Ex. 3-18 | Ex. 3-19 | Ex. 3-20 |
|---|---|---|---|---|---|---|---|
| Component A | A-α-1 | pbw |  |  |  |  |  |
|  | A-α-2 |  |  |  |  |  |  |
|  | A-α-3 |  | 75 | 75 | 75 | 75 | 75 |
|  | A-β-2-1 |  | 25 | 25 | 25 | 25 | 25 |
| Component B | B-2 |  | 1 | 1 | 1 | 1 | 1 |
| Component B' | B'-1 |  |  |  |  |  |  |
|  | B'-2 |  |  |  |  |  |  |
| Component C | C-1 |  | 0.1 | 0.1 | 0.1 | 0.1 | 0.1 |
|  | C-2 |  |  |  |  |  |  |
|  | C-3 |  |  |  |  |  |  |
|  | C-4 |  |  |  |  |  |  |
| Component D | D-1 |  | 1 |  | 1 | 1 | 1 |
|  | D-2 |  |  | 1 |  |  |  |
| Component E | E-1 |  |  |  | 0.1 |  |  |
| Component F | F-1 |  |  |  |  | 5 |  |
|  | F-2 |  |  |  |  |  | 5 |
|  | F-3 |  |  |  |  |  |  |
|  | F-4 |  |  |  |  |  |  |
|  | F-5 |  |  |  |  |  |  |
| Work environment |  | — | ○ | ○ | ○ | ○ | ○ |
| Quantitative determination of isocyanate gas | | ppm | Not detected | Not detected | Not detected | Not detected | Not detected |
| Deflection temperature under load | | °C. | 121 | 123 | 125 | 115 | 114 |
| Tensile distortion at break | | % | 13 | 11 | 13 | 31 | 32 |

TABLE 3-3-continued

| | | | | | | | |
|---|---|---|---|---|---|---|---|
| Notched impact value | kJ/m$^2$ | 4 | 4 | 3 | 12 | 13 | |
| Hydrolysis resistance | % | 94 | 95 | 98 | 98 | 98 | |

| | | Unit | Ex. 3-21 | Ex. 3-22 | Ex. 3-23 | Ex. 3-24 |
|---|---|---|---|---|---|---|
| Component A | A-α-1 | pbw | | | | |
| | A-α-2 | | | | | |
| | A-α-3 | | 75 | 75 | 75 | 75 |
| | A-β-2-1 | | 25 | 25 | 25 | 25 |
| Component B | B-2 | | 1 | 1 | 1 | 1 |
| Component B' | B'-1 | | | | | |
| | B'-2 | | | | | |
| Component C | C-1 | | 0.1 | 0.1 | 0.1 | 0.1 |
| | C-2 | | | | | |
| | C-3 | | | | | |
| | C-4 | | | | | |
| Component D | D-1 | | 1 | 1 | 1 | 1 |
| | D-2 | | | | | |
| Component E | E-1 | | | | | |
| Component F | F-1 | | | | | |
| | F-2 | | | | | |
| | F-3 | | 5 | | | |
| | F-4 | | | 5 | | 2 |
| | F-5 | | | | 5 | 5 |
| Work environment | | — | ○ | ○ | ○ | ○ |
| Quantitative determination of isocyanate gas | | ppm | Not detected | Not detected | Not detected | Not detected |
| Deflection temperature under load | | °C. | 116 | 117 | 116 | 112 |
| Tensile distortion at break | | % | 34 | 33 | 35 | 32 |
| Notched impact value | | kJ/m$^2$ | 12 | 12 | 11 | 15 |
| Hydrolysis resistance | | % | 97 | 99 | 99 | 98 |

Ex.: Example

TABLE 3-4

| | | Unit | Ex. 3-25 | Ex. 3-26 | Ex. 3-27 | Ex. 3-28 | Ex. 3-29 |
|---|---|---|---|---|---|---|---|
| Component A | A-α-1 | pbw | | | | | |
| | A-α-2 | | | | | | |
| | A-α-3 | | 75 | 75 | 75 | 75 | 75 |
| | A-β-2-1 | | 25 | 25 | 25 | 25 | 25 |
| Component B | B-2 | | 1 | 1 | 1 | 1 | 1 |
| Component B' | B'-1 | | | | | | |
| | B'-2 | | | | | | |
| Component C | C-1 | | 0.1 | 0.1 | 0.1 | 0.1 | 0.1 |
| | C-2 | | | | | | |
| | C-3 | | | | | | |
| | C-4 | | | | | | |
| Component D | D-1 | | 1 | 1 | 1 | 1 | 1 |
| | D-2 | | | | | | |
| Component E | E-1 | | 0.1 | 0.1 | 0.1 | 0.1 | 0.1 |
| Component F | F-1 | | | 5 | 5 | 5 | 5 |
| | F-2 | | | | | | |
| | F-3 | | | | | | |
| | F-4 | | | | | | |
| | F-5 | | | | | | |
| Component G | G-1-1 | | 10 | 10 | | | |
| | G-1-2 | | | | 10 | | 12 |
| | G-1-3 | | | | | 10 | |
| | G-2-1 | | | | | | 6 |
| | G-2-2 | | | | | | |
| | G-3 | | | | | | |
| | G-4 | | | | | | |
| | G-5 | | | | | | |
| Component H | H-1 | | | | | | |
| Component I | I-1 | | | | | | 5 |
| | I-2 | | | | | | 0.5 |
| Work environment | | — | ○ | ○ | ○ | ○ | ○ |
| Quantitative determination of isocyanate gas | | ppm | Not detected | Not detected | Not detected | Not detected | Not detected |
| Deflection temperature under load | | °C. | 111 | 107 | 119 | 118 | 115 |
| Tensile distortion at break | | % | 6 | 23 | 19 | 18 | 17 |
| Notched impact value | | kJ/m$^2$ | 3 | 8 | 7 | 7 | 7 |
| Hydrolysis resistance | | % | 95 | 96 | 85 | 86 | 82 |
| Flame retardance | | — | V-2 | V-2 | V-2 | V-2 | V-0 |

TABLE 3-4-continued

| | | Unit | Ex. 3-30 | Ex. 3-31 | Ex. 3-32 | Ex. 3-33 | Ex. 3-34 |
|---|---|---|---|---|---|---|---|
| Component A | A-α-1 | pbw | | | | | |
| | A-α-2 | | | | | | |
| | A-α-3 | | 75 | 75 | 75 | 75 | 75 |
| | A-β-2-1 | | 25 | 25 | 25 | 25 | 25 |
| Component B | B-2 | | 1 | 1 | 1 | 1 | 1 |
| Component B' | B'-1 | | | | | | |
| | B'-2 | | | | | | |
| Component C | C-1 | | 0.1 | 0.1 | 0.1 | 0.1 | 0.1 |
| | C-2 | | | | | | |
| | C-3 | | | | | | |
| | C-4 | | | | | | |
| Component D | D-1 | | 1 | 1 | 1 | 1 | 1 |
| | D-2 | | | | | | |
| Component E | E-1 | | 0.1 | 0.1 | 0.1 | 0.1 | 0.1 |
| Component F | F-1 | | 5 | 5 | 5 | 5 | |
| | F-2 | | | | | | |
| | F-3 | | | | | | |
| | F-4 | | | | | | |
| | F-5 | | | | | | |
| Component G | G-1-1 | | | | | | |
| | G-1-2 | | | | | | |
| | G-1-3 | | 12 | 12 | | | |
| | G-2-1 | | 6 | | | | |
| | G-2-2 | | | 6 | | | |
| | G-3 | | | | 40 | | |
| | G-4 | | | | | 4 | 4 |
| | G-5 | | | | | 12 | 12 |
| Component H | H-1 | | | | | | 40 |
| Component I | I-1 | | 5 | 5 | 5 | | |
| | I-2 | | 0.5 | 0.5 | | 0.5 | 0.5 |
| Work environment | | — | ○ | ○ | ○ | ○ | ○ |
| Quantitative determination of isocyanate gas | | ppm | Not detected | Not detected | Not detected | Not detected | Not detected |
| Defrection temperature under load | | °C. | 119 | 112 | 122 | 125 | 203 |
| Tensile distortion at break | | % | 15 | 17 | 7 | 28 | 5 |
| Notched impact value | | kJ/m$^2$ | 7 | 7 | 5 | 11 | 12 |
| Hydrolysis resistance | | % | 82 | 83 | 78 | 98 | 98 |
| Flame retardance | | — | V-1 | V-1 | V-1 | V-0 | V-0 |

Ex.: Example

The resin compositions of Examples 3-1 to 3-15 were materials which ensured a good work environment, produced no isocyanate gas and were excellent in deflection temperature under load, tensile distortion at break, notched impact value and hydrolysis resistance. In Examples 3-16 and 3-17 in which the component D was further added, the further improvement of hydrolysis resistance was seen. Example 3-18 in which the component E-1 was further added was a material which saw the further improvement of hydrolysis resistance and was excellent in deflection temperature under load, notched impact value and tensile distortion at break. The resin compositions of Examples 3-19 to 3-24 were materials which saw the improvement of notched impact value and tensile distortion at break as they contained the component F, ensured a good work environment, produced no isocyanate gas and were excellent in deflection temperature under load and hydrolysis resistance. The resin compositions of Examples 3-25 to 3-34 were materials which further provided flame retardancy, ensured a good work environment, produced no isocyanate gas and were excellent in deflection temperature under load, notched impact value, tensile distortion at break and hydrolysis resistance.

Example 4-1

The poly-L-lactic acid (A-α-1) produced in Production Example 1-1 was used as the polylactic acid and premixed with components shown in Table 4-2 uniformly by dry blending, and the premixture was supplied from a first feed port and melt extruded into a pellet. The first feed port is a feed port at the base. Melt extrusion was carried out by using a 30 mmφ vented double-screw extruder having a side screw [TEX30XSST of The Japan Steel Works, Ltd.]. The extrusion temperatures of C1/C2/C3 to C11/D were 10° C./230° C./250° C./250° C., respectively, the revolution of the main screw was 200 rpm, the revolution of the side screw was 50 rpm, the delivery rate was 20 kg/h, and the vent vacuum degree was 3 kPa.

The obtained pellet was dried at 80° C. for 5 hours by means of a hot air circulating drier and molded by means of an injection molding machine (IS-150EN of Toshiba Machine Co., Ltd.) to make evaluations. The results are shown in Table 4-2.

Example 4-2

A pellet was obtained in the same manner as in Example 4-1 except that the poly-D-lactic acid (A-α-2) produced in Production Example 1-2 was used as the polylactic acid and evaluated. The results are shown in Table 4-2.

Examples 4-3 to 4-35

Pellets were obtained in the same manner as in Example 4-1 except that the stereocomplex polylactic acid (A-α-3) produced in Production Example 1-3 was used as the polylactic acid and evaluated. In the composition comprising the component I-1, components excluding the component I-1 were premixed together uniformly by dry blending, and the premixture was supplied from the first feed port and the component I-1 was supplied from a second feed port. The second feed port is provided in a side screw. The results are shown in Tables 4-2 to 4-5. The word "collapse" for hydrolysis resistance in these tables means that a molded article lost its original shape after a moist heat treatment and a tensile test could not be made.

TABLE 4-1

|  |  | Unit | Ex. 4-1 | Ex. 4-2 | Ex. 4-3 | Ex. 4-4 | Ex. 4-5 | Ex. 4-6 | Ex. 4-7 |
|---|---|---|---|---|---|---|---|---|---|
| Component A | A-α-1 | pbw | 75 |  |  |  |  |  |  |
|  | A-α-2 |  |  | 75 |  |  |  |  |  |
|  | A-α-3 |  |  |  | 75 | 50 | 25 | 75 | 75 |
|  | A-β-3-1 |  | 25 | 25 | 25 | 50 | 75 | 25 | 25 |
| Component B | B-2 |  | 1 | 1 | 1 | 1 | 1 | 0.05 | 8 |
| Component B' | B'-1 |  |  |  |  |  |  |  |  |
|  | B'-2 |  |  |  |  |  |  |  |  |
| Component C | C-1 |  | 0.1 | 0.1 | 0.1 | 0.1 | 0.1 | 0.1 | 0.1 |
|  | C-2 |  |  |  |  |  |  |  |  |
|  | C-3 |  |  |  |  |  |  |  |  |
|  | C-4 |  |  |  |  |  |  |  |  |
| Work environment |  | — | ○ | ○ | ○ | ○ | ○ | ○ | ○ |
| Quantitative determination of isocyanate gas |  | ppm | Not detected | Not detected | Not detected | Not detected | Not detected | Not detected | Not detected |
| Hydrolysis resistance |  | % | 84 | 83 | 91 | 96 | 100 | 82 | 82 |
| Melt heat stability |  | — | ○ | ○ | ○ | ○ | ○ | ○ | ○ |

|  |  | Unit | Ex. 4-8 | Ex. 4-9 | Ex. 4-10 | Ex. 4-11 | Ex. 4-12 | Ex. 4-13 | Ex. 4-14 | Ex. 4-15 |
|---|---|---|---|---|---|---|---|---|---|---|
| Component A | A-α-1 | pbw |  |  |  |  |  |  |  |  |
|  | A-α-2 |  |  |  |  |  |  |  |  |  |
|  | A-α-3 |  | 75 | 75 | 75 | 75 | 75 | 75 | 75 | 75 |
|  | A-β-3-1 |  | 25 | 25 | 25 | 25 | 25 | 25 | 25 | 25 |
| Component B | B-2 |  | 1 | 1 | 1 | 1 | 1 | 1 | 1 | 1 |
| Component B' | B'-1 |  |  |  |  |  |  |  |  |  |
|  | B'-2 |  |  |  |  |  |  |  |  |  |
| Component C | C-1 |  |  |  |  | 0.1 | 0.1 | 0.1 | 0.003 | 2 |
|  | C-2 |  | 0.1 |  |  | 0.1 |  |  |  |  |
|  | C-3 |  |  | 0.1 |  |  | 0.1 |  |  |  |
|  | C-4 |  |  |  | 0.1 |  |  | 0.1 |  |  |
| Work environment |  | — | ○ | ○ | ○ | ○ | ○ | ○ | ○ | ○ |
| Quantitative determination of isocyanate gas |  | ppm | Not detected | Not detected | Not detected | Not detected | Not detected | Not detected | Not detected | Not detected |
| Hydrolysis resistance |  | % | 88 | 89 | 87 | 95 | 94 | 95 | 85 | 85 |
| Melt heat stability |  | — | ○ | ○ | ○ | ○ | ○ | ○ | ○ | ○ |

Ex.: Example

TABLE 4-2

|  |  | Unit | Ex. 4-8 | Ex. 4-9 | Ex. 4-10 | Ex. 4-11 | Ex. 4-12 | Ex. 4-13 | Ex. 4-14 | Ex. 4-15 |
|---|---|---|---|---|---|---|---|---|---|---|
| Component A | A-α-1 | pbw |  |  |  |  |  |  |  |  |
|  | A-α-2 |  |  |  |  |  |  |  |  |  |
|  | A-α-3 |  | 75 | 75 | 75 | 75 | 75 | 75 | 75 | 75 |
|  | A-β-3-1 |  | 25 | 25 | 25 | 25 | 25 | 25 | 25 | 25 |
| Component B | B-2 |  | 1 | 1 | 1 | 1 | 1 | 1 | 1 | 1 |
| Component B' | B'-1 |  |  |  |  |  |  |  |  |  |
|  | B'-2 |  |  |  |  |  |  |  |  |  |
| Component C | C-1 |  |  |  |  | 0.1 | 0.1 | 0.1 | 0.003 | 2 |
|  | C-2 |  | 0.1 |  |  | 0.1 |  |  |  |  |
|  | C-3 |  |  | 0.1 |  |  | 0.1 |  |  |  |
|  | C-4 |  |  |  | 0.1 |  |  | 0.1 |  |  |
| Work environment |  | — | ○ | ○ | ○ | ○ | ○ | ○ | ○ | ○ |
| Quantitative determination of isocyanate gas |  | ppm | Not detected | Not detected | Not detected | Not detected | Not detected | Not detected | Not detected | Not detected |
| Hydrolysis resistance |  | % | 88 | 89 | 87 | 95 | 94 | 95 | 85 | 85 |
| Melt heat stability |  | — | ○ | ○ | ○ | ○ | ○ | ○ | ○ | ○ |

Ex.: Example

TABLE 4-3

|  |  | Unit | Ex. 4-16 | Ex. 4-17 | Ex. 4-18 | Ex. 4-19 | Ex. 4-20 |
|---|---|---|---|---|---|---|---|
| Component A | A-α-1 | pbw |  |  |  |  |  |
|  | A-α-2 |  |  |  |  |  |  |
|  | A-α-3 |  | 75 | 75 | 75 | 75 | 75 |
|  | A-β-3-1 |  | 25 | 25 | 25 | 25 | 25 |
| Component B | B-2 |  | 1 | 1 | 1 | 1 | 1 |
| Component B' | B'-1 |  |  |  |  |  |  |
|  | B'-2 |  |  |  |  |  |  |
| Component C | C-1 |  | 0.1 | 0.1 | 0.1 | 0.1 | 0.1 |
|  | C-2 |  |  |  |  |  |  |
|  | C-3 |  |  |  |  |  |  |
|  | C-4 |  |  |  |  |  |  |
| Component D | D-1 |  | 1 |  | 1 | 1 | 1 |
|  | D-2 |  |  | 1 |  |  |  |
| Component E | E-1 |  |  |  | 0.1 |  |  |
| Component F | F-1 |  |  |  |  | 5 |  |
|  | F-2 |  |  |  |  |  | 5 |
|  | F-3 |  |  |  |  |  |  |
|  | F-4 |  |  |  |  |  |  |
|  | F-5 |  |  |  |  |  |  |
| Work environment |  | — | ○ | ○ | ○ | ○ | ○ |
| Quantitative determination of isocyanate gas |  | ppm | Not detected | Not detected | Not detected | Not detected | Not detected |
| Hydrolysis resistance |  | % | 95 | 95 | 100 | 100 | 100 |
| Melt heat stability |  | — | ○ | ○ | ○ | ○ | ○ |

|  |  | Unit | Ex. 4-21 | Ex. 4-22 | Ex. 4-23 | Ex. 4-24 |
|---|---|---|---|---|---|---|
| Component A | A-α-1 | pbw |  |  |  |  |
|  | A-α-2 |  |  |  |  |  |
|  | A-α-3 |  | 75 | 75 | 75 | 75 |
|  | A-β-3-1 |  | 25 | 25 | 25 | 25 |
| Component B | B-2 |  | 1 | 1 | 1 | 1 |
| Component B' | B'-1 |  |  |  |  |  |
|  | B'-2 |  |  |  |  |  |
| Component C | C-1 |  | 0.1 | 0.1 | 0.1 | 0.1 |
|  | C-2 |  |  |  |  |  |
|  | C-3 |  |  |  |  |  |
|  | C-4 |  |  |  |  |  |
| Component D | D-1 |  | 1 | 1 | 1 | 1 |
|  | D-2 |  |  |  |  |  |
| Component E | E-1 |  |  |  |  |  |
| Component F | F-1 |  |  |  |  |  |
|  | F-2 |  |  |  |  |  |
|  | F-3 |  | 5 |  |  |  |
|  | F-4 |  |  | 5 |  | 2 |
|  | F-5 |  |  |  | 5 | 5 |
| Work environment |  | — | ○ | ○ | ○ | ○ |
| Quantitative determination of isocyanate gas |  | ppm | Not detected | Not detected | Not detected | Not detected |
| Hydrolysis resistance |  | % | 100 | 100 | 100 | 100 |
| Melt heat stability |  | — | ○ | ○ | ○ | ○ |

Ex.: Example

TABLE 4-4

|  |  | Unit | Ex. 4-25 | Ex. 4-26 | Ex. 4-27 | Ex. 4-28 | Ex. 4-29 | Ex. 4-30 |
|---|---|---|---|---|---|---|---|---|
| Component A | A-α-1 | pbw |  |  |  |  |  |  |
|  | A-α-2 |  |  |  |  |  |  |  |
|  | A-α-3 |  | 75 | 75 | 75 | 75 | 75 | 75 |
|  | A-β-3-1 |  | 25 | 25 | 25 | 25 | 25 | 25 |
| Component B | B-2 |  | 1 | 1 | 1 | 1 | 1 | 1 |
| Component B' | B'-1 |  |  |  |  |  |  |  |
|  | B'-2 |  |  |  |  |  |  |  |
| Component C | C-1 |  | 0.1 | 0.1 | 0.1 | 0.1 | 0.1 | 0.1 |
|  | C-2 |  |  |  |  |  |  |  |
|  | C-3 |  |  |  |  |  |  |  |
|  | C-4 |  |  |  |  |  |  |  |
| Component D | D-1 |  | 1 | 1 | 1 | 1 | 1 | 1 |
|  | D-2 |  |  |  |  |  |  |  |
|  | D-3 |  |  |  |  |  |  |  |
| Component E | E-1 |  | 0.1 | 0.1 | 0.1 | 0.1 | 0.1 | 0.1 |
| Component F | F-1 |  |  | 5 | 5 | 5 | 5 | 5 |
|  | F-2 |  |  |  |  |  |  |  |
|  | F-3 |  |  |  |  |  |  |  |
|  | F-4 |  |  |  |  |  |  |  |
|  | F-5 |  |  |  |  |  |  |  |

TABLE 4-4-continued

| Component G | G-1-1 | | 10 | 10 | | | | |
|---|---|---|---|---|---|---|---|---|
| | G-1-2 | | | | 10 | 10 | 10 | |
| | G-1-3 | | | | | 10 | | 10 |
| | G-2-1 | | | | | | 5 | 5 |
| | G-2-2 | | | | | | | |
| | G-3 | | | | | | | |
| | G-4 | | | | | | | |
| | G-5 | | | | | | | |
| | G-6 | | | | | | | |
| | G-7 | | | | | | | |
| Component H | H-1 | | | | | | | |
| Component I | I-1 | | | | | | 5 | 5 |
| | I-2 | | | | | | 0.5 | 0.5 |
| Work environment | | — | ○ | ○ | ○ | ○ | ○ | ○ |
| Quantitative determination of isocyanate gas | | ppm | Not detected | Not detected | Not detected | Not detected | Not detected | Not detected |
| Hydrolysis resistance | | % | 98 | 99 | 89 | 97 | 87 | 94 |
| Work environment | | — | ○ | ○ | ○ | ○ | ○ | ○ |
| Flame retardance | | — | V-2 | V-2 | V-2 | V-2 | V-0 | V-0 |

| | | Unit | Ex. 4-31 | Ex. 4-32 | Ex. 4-33 | Ex. 4-34 | Ex. 4-35 |
|---|---|---|---|---|---|---|---|
| Component A | A-α-1 | pbw | | | | | |
| | A-α-2 | | | | | | |
| | A-α-3 | | 75 | 75 | 75 | 75 | 75 |
| | A-β-3-1 | | 25 | 25 | 25 | 25 | 25 |
| Component B | B-2 | | 1 | 1 | 1 | 1 | 1 |
| Component B' | B'-1 | | | | | | |
| | B'-2 | | | | | | |
| Component C | C-1 | | 0.1 | 0.1 | 0.1 | 0.1 | 0.1 |
| | C-2 | | | | | | |
| | C-3 | | | | | | |
| | C-4 | | | | | | |
| Component D | D-1 | | 1 | 1 | 1 | 1 | 1 |
| | D-2 | | | | | | |
| | D-3 | | | | | | |
| Component E | E-1 | | 0.1 | 0.1 | 0.1 | 0.1 | 0.1 |
| Component F | F-1 | | 5 | 5 | 5 | | 5 |
| | F-2 | | | | | | |
| | F-3 | | | | | | |
| | F-4 | | | | | | |
| | F-5 | | | | | | |
| Component G | G-1-1 | | | | | | |
| | G-1-2 | | | | | | |
| | G-1-3 | | 10 | | | | |
| | G-2-1 | | | | | | |
| | G-2-2 | | 5 | | | | |
| | G-3 | | | 40 | | | |
| | G-4 | | | | | 3 | 3 |
| | G-5 | | | | | | 5 |
| | G-6 | | | | | | 0.1 |
| | G-7 | | | | 10 | 10 | |
| Component H | H-1 | | | | | 40 | |
| Component I | I-1 | | 5 | 5 | | | |
| | I-2 | | 0.5 | | 0.5 | 0.5 | 0.5 |
| Work environment | | — | ○ | ○ | ○ | ○ | ○ |
| Quantitative determination of isocyanate gas | | ppm | Not detected | Not detected | Not detected | Not detected | Not detected |
| Hydrolysis resistance | | % | 89 | 86 | 98 | 85 | 97 |
| Work environment | | — | ○ | ○ | ○ | ○ | ○ |
| Flame retardance | | — | V-0 | V-0 | V-0 | V-0 | V-0 |

Ex.: Example

The resin compositions of Example 4-1 to 4-15 were materials which ensured a good work environment, produced no isocyanate gas and were excellent in hydrolysis resistance and melt heat stability. In Examples 4-16 and 4-17 in which the component D was further added, the further improvement of hydrolysis resistance was seen. In Example 4-18 in which the component E-1 was further added, the further improvement of hydrolysis resistance was seen. The resin compositions of Examples 4-19 to 4-24 saw the further improvement of hydrolysis resistance as they contained the component F. The resin compositions of Examples 4-25 to 4-35 were materials which provided flame retardancy, ensured a good work environment, produced no isocyanate gas and were excellent in hydrolysis resistance and melt heat stability.

EFFECT OF THE INVENTION

The resin composition of the present invention has excellent hydrolysis resistance and a low environmental burden. According to the production process of the resin composition of the present invention, when a cyclic carbodiimide compound (component B) and an antioxidant (component C) are added, the release of a compound having an isocyanate group is prevented, thereby making it possible to

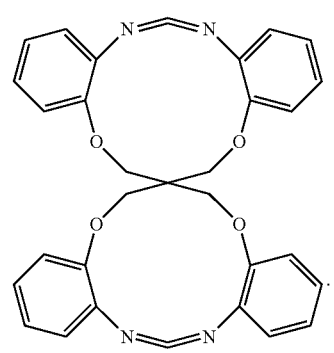 [SMILES: C1=Nc2ccccc2OCC2(COc3ccccc3N=1)COc1ccccc1N=C=Nc1ccccc1OC2]

The invention claimed is:

1. A resin composition comprising:
   (A) 100 parts by weight of a resin component (component A) containing polylactic acid (component A-α);
   (B) 0.001 to 10 parts by weight of a cyclic carbodiimide compound (component B) having a cyclic structure represented by the following formula (5) in which first nitrogen and second nitrogen are bonded to each other via a bonding group, wherein the cyclic structure consisting only one carbodiimide group in one cyclic structure, and wherein the total number of atoms of (i) carbodiimide group and (ii) minimum number of atoms in the bonding group which directly connects the first nitrogen and second nitrogen of the carbodiimide group is 8 to 50 ; and
   (C) 0.001 to 2 parts by weight of at least one antioxidant (component C) selected from the group consisting of a hindered phenol-based compound, a phosphite-based compound, a phosphonite-based compound and a thioether-based compound.

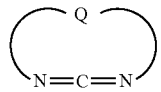

(5)

where in the above formula, Q is a divalent to tetravalent bonding group represented by the following formula (5-1) or (5-2):

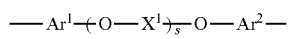

(5-1)

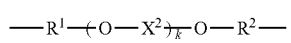

(5-2)

where the above formulas, $Ar^1$ and $Ar^2$ are each independently a divalent to tetravalent aromatic group having 5 to 15 carbon atoms; $R^1$ and $R^2$ are each independently a divalent to tetravalent aliphatic group having 1 to 20 carbon atoms, a divalent to tetravalent alicyclic group having 3 to 20 carbon atoms or a combination thereof; s is an integer of 0 to 10; k is an integer of 0 to 10; $X^1$ and $X^2$ are each independently a divalent to tetravalent aliphatic group having 1 to 20 carbon atoms, a divalent to tetravalent alicyclic group having 3 to 20 carbon atoms, a divalent to tetravalent aromatic group having 5 to 15 carbon atoms, or a combination thereof; Q when Q is a divalent bonding group, $Ar^1$, $Ar^2$, $R^1$, $R^2$, $X^1$ and $X^2$ are all divalent groups; when Q is a trivalent bonding group, one of $A^1$, $Ar^2$, $R^1$, $R^2$, $X^1$ and $X^2$ is a trivalent group; and when Q is a tetravalent bonding group, one of $Ar^1$, $Ar^2$, $R^1$, $R^2$, $X^1$ and $X^2$ is a tetravalent group, or two of them are trivalent groups.

2. The resin composition according to claim 1, wherein the cyclic carbodiimide compound (component B) is a compound represented by the following formula (6):

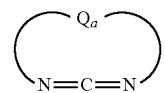

(6)

where in the above formula, $Q_a$ is a divalent bonding group represented by the following formula (6-1) or (6-2)

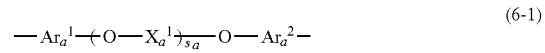

(6-1)

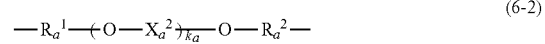

(6-2)

where in the above formulas, $Ar_a^1$, $Ar_a^2$, $R_a^1$, $R_a^2$, $X_a^1$, $X_a^2$, $s_a$ and $k_a$ are identical to $Ar^1$, $Ar^2$, $R^1$, $R^2$, $X^1$, $X^2$, s and k in the above formulas (5-1) and (5-2), respectively; and they are divalent groups.

3. The resin composition according to claim 1, wherein the cyclic carbodiimide compound (component B) is a compound represented by the following formula (7):

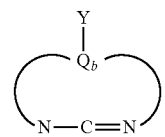

(7)

where in the above formula, $Q_b$ is a trivalent bonding group represented by the following formula (7-1) or (7-2) and Y is a carrier supporting a cyclic structure:

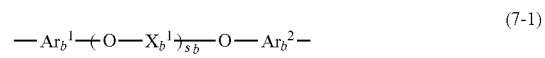

(7-1)

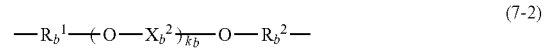

(7-2)

where in the above formulas, $Ar_b^1$, $Ar_b^2$, $R_b^1$, $R_b^2$, $X_b^1$, $X_b^2$, $s_b$ and $k_b$ are identical to $Ar^1$, $Ar^2$, $R^1$, $R^2$, $X^1$, $X^2$, s and k in the above formulas (5-1) and (5-2), respectively, and one of them is a trivalent group.

4. The resin composition according to claim 1, wherein the cyclic carbodiimide compound (component B) is a compound represented by the following formula (8):

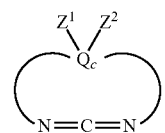

(8)

where in the above formula, $Q_c$ is a tetravalent bonding group represented by the following formula (8-1) or (8-2), and $Z^1$ and $Z^2$ are carriers supporting a cyclic structure; $Z^1$ and $Z^2$ may be bonded together to form a cyclic structure:

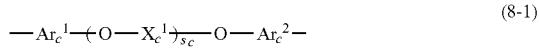

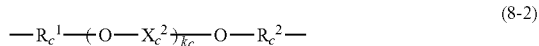

wherein $Ar_c^1$, $Ar_c^2$, $R_c^1$, $R_c^2$, $X_c^1$, $X_c^2$, $s_c$ and $k_c$ are identical to $Ar^1$, $Ar^2$, $R^1$, $R^2$, $X^1$, $X^2$, s and k in the above formulas (5-1) to (5-2), respectively, and one of $Ar_c^1$, $Ar_c^2$, $R_c^1$, $R_c^2$, $X_c^1$, $X_c^2$ is a tetravalent group, or two of them are trivalent groups.

5. The resin composition according to claim 1, wherein the resin component (component A) comprises 5 to 95 wt % of polylactic acid (component A-α) and 95 to 5 wt % of at least one thermoplastic resin (component A-β) selected from the group consisting of an aromatic polyester (component A-β-1), a polyolefin (component A-β-2) and an aromatic polycarbonate (component A-β-3).

6. The resin composition according to claim 1, wherein the polylactic acid (component A-α) contains poly-L-lactic acid (component A-α-1) essentially composed of an L-lactic acid unit and poly-D-lactic acid (component A-α-2) essentially composed of a D-lactic acid unit, and the weight ratio of the component A-α-1 to the component A-α-2 is 10:90 to 90:10.

7. The resin composition according to claim 6, wherein the poly-L-lactic acid (component A-α-1) contains 90 mol % or more of an L-lactic acid unit and the poly-D-lactic acid (component A-α-2) contains 90 mol % or more of a D-lactic acid unit.

8. The resin composition according to claim 6, wherein the polylactic acid (component A) has a stereocomplex crystal rate represented by the following equation using melting enthalpy in the temperature elevation step of differential scanning calorimeter (DSC) measurement of 80% or more:

Stereocomplex crystal rate=ΔHms/(ΔHms+ΔHmh)×100 wherein in the above equation, ΔHmh and ΔHms represent the melting enthalpy (ΔHmh) of a crystal melting point which appears at a temperature lower than 190° C. and the melting enthalpy (ΔHms) of a crystal melting point which appears at a temperature of 190° C. or higher to lower than 250° C. in the temperature elevation step of a differential scanning calorimeter (DSC), respectively.

9. The resin composition according to claim 1 which comprises 0.001 to 10 parts by weight of at least one end-sealing agent (component D) selected from the group consisting of an epoxy compound, an oxazoline compound and an oxazine compound based on 100 parts by weight of the resin component (component A).

10. The resin composition according to claim 1 which comprises 0.01 to 0.3 part by weight of hydrotalcite (component E) based on 100 parts by weight of the resin component (component A).

11. The resin composition according to claim 1 which comprises 2 to 100 parts by weight of an impact modifier (component F) based on 100 parts by weight of the resin component (component A).

12. The resin composition according to claim 1 which comprises 1 to 100 parts by weight of at least one flame retardant (component G) selected from the group consisting of a phosphorus-based flame retardant (component G-1), a nitrogen-based flame retardant (component G-2), a metal hydroxide-based flame retardant (component G-3), a metal oxide-based flame retardant (component G-4) and a bromine-based flame retardant (component G-5) based on 100 parts by weight of the resin component (component A).

13. A molded article which is made of the resin composition of claim 1.

14. The molded article according to claim 13 which is formed by injection molding, extrusion molding, thermomolding, blow molding or foam molding.

15. The molded article according to claim 13 which is an auto part, an electric/electronic part, an exterior part for electric equipment or an exterior part for OA equipment.

16. A process for producing the resin composition of claim 1, comprising the steps of:
(i) Preparing a stereocomplex polylactic acid by melt kneading together poly-L-lactic acid (component A-α-1) and poly-D-lactic acid (component A-α-2) in a weight ratio of 10:90 to 90:10; and
(ii) melt kneading together (A) 100 parts by weight of a resin component (component A) containing the stereocomplex polylactic acid, (B) 0.001 to 10 parts by weight of a cyclic carbodiimide compound (component B) having one carbodiimide group and a cyclic structure represented by the formula (5) in which first nitrogen and second nitrogen are bonded to each other via a bonding group, wherein the number of atoms directly constituting the cyclic structure consisting of 8 to 50 atoms, and (C) 0.001 to 2 parts by weight of at least one antioxidant (component C) selected from the group consisting of a hindered phenol-based compound, a phosphite-based compound, a phosphonite-based compound and a thioether-based compound.

17. The production process according to claim 16, wherein the resin component (component A) contains 5 to 95 wt % of the stereocomplex polylactic acid (component A-α-3) and 95 to 5 wt % of at least one thermoplastic resin (component A-β) selected from the group consisting of an aromatic polyester (component A-β-1), a polyolefin (component A-β-2) and an aromatic polycarbonate (component A-β-3).

18. The resin composition according to claim 1, wherein the total numbers of atoms of (i) carbodiimide group and (ii) minimum number of atoms in the bonding group which directly connects the first nitrogen and the second nitrogen of the carbodiimide group is 12 to 50.

19. The resin composition according to claim 1, wherein the total number of atoms of (i) carbodiimide group and (ii) minimum number of atoms in the bonding group which directly connects the first nitrogen and the second nitrogen of the carbodiimide group is 14 to 50.

20. The resin composition according to claim 1, wherein the cyclic carbodiimide compound is the compound set forth below: